(12) United States Patent
McAlister

(10) Patent No.: US 8,911,703 B2
(45) Date of Patent: Dec. 16, 2014

(54) REDUCING AND/OR HARVESTING DRAG ENERGY FROM TRANSPORT VEHICLES, INCLUDING FOR CHEMICAL REACTORS, AND ASSOCIATED SYSTEMS AND METHODS

(71) Applicant: McAlister Technologies, LLC, Phoenix, AZ (US)

(72) Inventor: Roy Edward McAlister, Phoenix, AZ (US)

(73) Assignee: McAlister Technologies, LLC, Phoenix, AZ (US)

( * ) Notice: Subject to any disclaimer, the term of this patent is extended or adjusted under 35 U.S.C. 154(b) by 4 days.

(21) Appl. No.: 13/764,493

(22) Filed: Feb. 11, 2013

(65) Prior Publication Data

US 2013/0158828 A1    Jun. 20, 2013

Related U.S. Application Data

(63) Continuation-in-part of application No. 13/584,786, filed on Aug. 13, 2012.

(60) Provisional application No. 61/522,909, filed on Aug. 12, 2011.

(51) Int. Cl.
*B60W 10/196* (2012.01)
(Continued)

(52) U.S. Cl.
CPC .............. *B60W 10/196* (2013.01); *B01J 19/20* (2013.01); *B60L 8/006* (2013.01);
(Continued)

(58) Field of Classification Search
None
See application file for complete search history.

(56) References Cited

U.S. PATENT DOCUMENTS 2,013,652 A * 9/1935 Hall .............................. 252/374
2,131,134 A * 9/1938 Collins et al. .................. 422/31
(Continued)

FOREIGN PATENT DOCUMENTS

| CA | 2521698 A1 | 8/2005 |
| CH | 692927 A5 | 12/2002 |

(Continued)

OTHER PUBLICATIONS

U.S. Appl. No. 13/685,075, filed Nov. 26, 2012, McAlister.
(Continued)

*Primary Examiner* — Melvin C Mayes
*Assistant Examiner* — Douglas Call
(74) *Attorney, Agent, or Firm* — Perkins Coie LLP

(57) ABSTRACT

The present disclosure is directed to systems and methods for reducing and/or harvesting drag energy from transport vehicles. A system in accordance with a particular embodiment includes a mobile transport platform, a donor substance source carried by the platform, and a thermochemical reactor carried by the platform and coupled to the donor substance. The reactor is configured to carry out a non-combustion dissociation process that dissociates the donor substance into a first constituent and a second constituent. An energy extraction system carried by the transport platform and positioned to extract energy from an airstream passing the transport platform is coupled to the reactor to provide energy for the dissociation process.

13 Claims, 41 Drawing Sheets

(51) Int. Cl.
*A61L 2/16* (2006.01)
*A61L 2/20* (2006.01)
*B60W 10/06* (2006.01)
*B01J 19/20* (2006.01)
*B60L 8/00* (2006.01)
*F03D 9/00* (2006.01)
*B60L 7/08* (2006.01)
*B60T 1/00* (2006.01)
*C01B 3/34* (2006.01)
*F03D 11/04* (2006.01)
*C01B 3/24* (2006.01)
*H02P 9/04* (2006.01)
*C01B 3/22* (2006.01)
*B01J 4/00* (2006.01)
*B60L 11/18* (2006.01)
*B01J 19/24* (2006.01)
*B60L 11/00* (2006.01)
*B60T 1/10* (2006.01)
*B60L 11/16* (2006.01)
*C01B 3/36* (2006.01)
*C01B 3/04* (2006.01)
*F28C 3/00* (2006.01)
*B60T 1/16* (2006.01)

(52) U.S. Cl.
CPC ............ *F03D 9/00* (2013.01); *Y02E 60/364* (2013.01); *B60L 7/08* (2013.01); *B01J 2219/00159* (2013.01); *B60L 2240/12* (2013.01); *A61L 2/20* (2013.01); *B01J 2219/00135* (2013.01); *B60T 1/00* (2013.01); *B60L 2200/36* (2013.01); *C01B 2203/0238* (2013.01); *C01B 3/34* (2013.01); *F05B 2240/941* (2013.01); *A61L 2/16* (2013.01); *F03D 11/04* (2013.01); *C01B 2203/025* (2013.01); *C01B 3/24* (2013.01); *Y02E 10/728* (2013.01); *C01B 2203/0233* (2013.01); *H02P 9/04* (2013.01); *C01B 3/22* (2013.01); *B01J 2219/00139* (2013.01); *B60W 10/06* (2013.01); *B01J 4/002* (2013.01); *B60L 11/1875* (2013.01); *B01J 19/24* (2013.01); *B60L 11/005* (2013.01); *C01B 2203/1241* (2013.01); *B60T 1/10* (2013.01); *C01B 2203/0266* (2013.01); *C01B 2203/1235* (2013.01); *C01B 2203/1205* (2013.01); *B60L 2240/36* (2013.01); *B01J 2219/00157* (2013.01); *B60L 11/16* (2013.01); *C01B 3/36* (2013.01); *B01J 2219/00085* (2013.01); *C01B 3/04* (2013.01); *F28C 3/005* (2013.01); *B60T 1/16* (2013.01); *B01J 2219/00155* (2013.01); *B01J 2219/00144* (2013.01)
USPC ............... 423/650; 62/62; 123/320; 422/40; 422/187; 701/70

(56) References Cited

U.S. PATENT DOCUMENTS

| | | | |
|---|---|---|---|
| 3,063,258 A * | 11/1962 | Szachnitowski | ............... 62/309 |
| 3,613,792 A | 10/1971 | Hyde et al. | |
| 3,633,372 A | 1/1972 | Kimmel et al. | |
| 3,662,832 A | 5/1972 | Keeler et al. | |
| 3,757,860 A | 9/1973 | Pritchett | |
| 3,788,389 A | 1/1974 | Waters | |
| 3,807,491 A | 4/1974 | Van Hulsen | |
| 3,830,508 A | 8/1974 | Endicott | |
| 3,840,068 A | 10/1974 | Waters | |
| 3,882,937 A | 5/1975 | Robinson | |
| 3,936,652 A | 2/1976 | Levine | |
| 3,975,912 A | 8/1976 | Greene | |
| 3,986,362 A | 10/1976 | Baciu | |
| 3,990,502 A | 11/1976 | Best | |
| 3,991,817 A | 11/1976 | Clay | |
| 4,019,868 A | 4/1977 | Sebacher et al. | |
| 4,053,576 A | 10/1977 | Fletcher | |
| 4,070,861 A | 1/1978 | Scragg et al. | |
| 4,082,865 A | 4/1978 | Ban et al. | |
| 4,099,489 A | 7/1978 | Bradley | |
| 4,138,993 A | 2/1979 | Conley | |
| 4,158,354 A | 6/1979 | Carden | |
| 4,161,211 A | 7/1979 | Duffy et al. | |
| 4,169,460 A | 10/1979 | Popovich et al. | |
| 4,172,506 A | 10/1979 | Terry | |
| 4,178,987 A | 12/1979 | Bowman et al. | |
| 4,229,184 A | 10/1980 | Gregg | |
| 4,257,239 A | 3/1981 | Partin et al. | |
| 4,343,338 A | 8/1982 | Hart | |
| 4,382,189 A | 5/1983 | Wilson | |
| 4,386,801 A | 6/1983 | Chapman et al. | |
| 4,401,689 A | 8/1983 | Ban | |
| 4,455,045 A | 6/1984 | Wheeler | |
| 4,519,342 A | 5/1985 | Yoon | |
| 4,549,078 A | 10/1985 | Monahan | |
| 4,549,528 A | 10/1985 | Gibson | |
| 4,601,508 A | 7/1986 | Kerian | |
| 4,611,847 A | 9/1986 | Sullivan | |
| 4,620,580 A | 11/1986 | Groezinger et al. | |
| 4,704,267 A | 11/1987 | DiMartino | |
| 4,706,651 A | 11/1987 | Yudow | |
| 4,746,160 A | 5/1988 | Wiesemeyer | |
| 4,848,445 A | 7/1989 | Harper | |
| 4,921,580 A | 5/1990 | Martes et al. | |
| 4,978,162 A | 12/1990 | Labbe | |
| 5,058,945 A | 10/1991 | Elliott, Sr. et al. | |
| 5,119,897 A | 6/1992 | Moriwake | |
| 5,132,090 A | 7/1992 | Volland | |
| 5,222,698 A | 6/1993 | Nelson et al. | |
| 5,253,700 A * | 10/1993 | Early, Jr. | ............... 165/42 |
| 5,280,990 A | 1/1994 | Rinard | |
| 5,315,868 A | 5/1994 | Jacobi et al. | |
| 5,348,774 A | 9/1994 | Golecki et al. | |
| 5,407,245 A | 4/1995 | Geropp | |
| 5,442,934 A | 8/1995 | Wolflick | |
| 5,498,059 A | 3/1996 | Switlik | |
| 5,558,721 A | 9/1996 | Kohmura et al. | |
| 5,560,443 A | 10/1996 | DuBose | |
| 5,618,134 A | 4/1997 | Balch | |
| 5,647,877 A | 7/1997 | Epstein | |
| 5,881,559 A | 3/1999 | Kawamura | |
| 5,882,382 A | 3/1999 | Hachisuka et al. | |
| 5,986,429 A | 11/1999 | Mula, Jr. | |
| 6,012,065 A | 1/2000 | Boucher et al. | |
| 6,068,328 A | 5/2000 | Gazdzinski | |
| 6,074,696 A | 6/2000 | Sato | |
| 6,081,183 A | 6/2000 | Mading et al. | |
| 6,089,224 A | 7/2000 | Poulek | |
| 6,092,861 A | 7/2000 | Whelan | |
| 6,155,212 A | 12/2000 | McAlister | |
| 6,200,069 B1 | 3/2001 | Miller | |
| 6,216,599 B1 | 4/2001 | Cavanagh | |
| 6,220,193 B1 | 4/2001 | Dilks | |
| 6,242,752 B1 | 6/2001 | Soma et al. | |
| 6,309,010 B1 | 10/2001 | Whitten | |
| 6,334,928 B1 | 1/2002 | Sekine et al. | |
| 6,378,932 B1 | 4/2002 | Fasel et al. | |
| 6,409,252 B1 | 6/2002 | Andrus | |
| 6,464,755 B2 | 10/2002 | Nakanishi et al. | |
| 6,502,533 B1 | 1/2003 | Meacham | |
| 6,508,209 B1 | 1/2003 | Collier, Jr. | |
| 6,531,704 B2 | 3/2003 | Yadav et al. | |
| 6,534,210 B2 | 3/2003 | Luken et al. | |
| 6,571,747 B1 | 6/2003 | Gerstweiler | |
| 6,585,785 B1 | 7/2003 | Warren et al. | |
| 6,630,267 B2 | 10/2003 | Badding et al. | |
| 6,749,043 B2 | 6/2004 | Brown et al. | |
| 6,756,140 B1 | 6/2004 | McAlister | |
| 6,756,565 B2 | 6/2004 | Suenaga et al. | |
| 6,838,782 B2 | 1/2005 | Vu | |

(56) References Cited

U.S. PATENT DOCUMENTS

| | | |
|---|---|---|
| 6,854,788 B1 | 2/2005 | Graham |
| 6,881,508 B2 | 4/2005 | Penev |
| 6,886,249 B2 | 5/2005 | Smalc |
| 6,889,755 B2 | 5/2005 | Zuo et al. |
| 6,897,575 B1 | 5/2005 | Yu |
| 6,908,297 B2 | 6/2005 | Dafft et al. |
| 6,919,062 B1 | 7/2005 | Vasileiadis et al. |
| 6,923,004 B2 | 8/2005 | Chandran et al. |
| 6,926,345 B2 | 8/2005 | Ortega et al. |
| 6,979,049 B2 | 12/2005 | Ortega et al. |
| 6,984,305 B2 | 1/2006 | McAlister |
| 7,014,737 B2 | 3/2006 | Harutyunyan et al. |
| 7,033,570 B2 | 4/2006 | Weimer et al. |
| 7,051,794 B2 | 5/2006 | Luo |
| 7,140,181 B1 | 11/2006 | Jensen et al. |
| 7,152,908 B2 | 12/2006 | Shahbazi |
| 7,165,804 B2 | 1/2007 | Shahbazi |
| 7,179,383 B1 | 2/2007 | Porter et al. |
| 7,185,944 B2 | 3/2007 | Shahbazi |
| 7,207,620 B2 | 4/2007 | Cosgrove et al. |
| 7,210,467 B2 | 5/2007 | Kweon et al. |
| 7,211,905 B1 | 5/2007 | McDavid, Jr. |
| 7,237,827 B2 | 7/2007 | Shahbazi |
| 7,243,980 B2 | 7/2007 | Vala |
| 7,250,151 B2 | 7/2007 | Tonkovich et al. |
| 7,285,350 B2 | 10/2007 | Keefer et al. |
| 7,293,533 B2 | 11/2007 | Hemsath |
| 7,337,612 B2 | 3/2008 | Skinnes et al. |
| 7,343,971 B2 | 3/2008 | Pfefferle |
| 7,397,141 B2 | 7/2008 | Gouker |
| 7,420,004 B2 | 9/2008 | Hardy et al. |
| 7,426,959 B2 | 9/2008 | Wang et al. |
| 7,449,158 B2 | 11/2008 | Haueter et al. |
| 7,484,553 B2 | 2/2009 | Lai et al. |
| 7,504,739 B2 | 3/2009 | Enis et al. |
| 7,527,094 B2 | 5/2009 | McKinzie et al. |
| 7,568,479 B2 | 8/2009 | Rabinowitz |
| 7,582,167 B2 | 9/2009 | Kaszuba et al. |
| 7,585,339 B2 | 9/2009 | Dahl et al. |
| 7,587,998 B2 | 9/2009 | Hotta et al. |
| 7,597,068 B2 | 10/2009 | Arai et al. |
| 7,608,120 B2 | 10/2009 | Wunning |
| 7,621,262 B2 | 11/2009 | Zubeck |
| 7,628,137 B1 | 12/2009 | McAlister |
| 7,692,170 B2 | 4/2010 | Gaus et al. |
| 7,713,642 B2 | 5/2010 | Warner et al. |
| 7,714,258 B2 | 5/2010 | Dalton |
| 7,753,122 B2 | 7/2010 | Curlett |
| 7,775,261 B2 | 8/2010 | Valenzuela |
| 7,788,924 B2 | 9/2010 | Hines |
| 7,789,182 B2 | 9/2010 | Bradley et al. |
| 7,799,315 B2 | 9/2010 | Amendola |
| 7,808,121 B1 | 10/2010 | Glynn |
| 7,856,843 B2 | 12/2010 | Enis et al. |
| 7,884,308 B1 | 2/2011 | Mejia |
| 7,943,045 B2 | 5/2011 | Rohrich et al. |
| 7,955,478 B2 | 6/2011 | McClure |
| 7,963,328 B2 | 6/2011 | Khinkis et al. |
| 7,971,861 B2 | 7/2011 | Soininen |
| 7,972,471 B2 | 7/2011 | Sant |
| 8,043,592 B2 | 10/2011 | Krass |
| 8,053,916 B2 | 11/2011 | Edwards et al. |
| 8,083,520 B2 | 12/2011 | Mueller et al. |
| 8,136,740 B2 | 3/2012 | Hagen et al. |
| 8,187,549 B2 | 5/2012 | McAlister |
| 8,187,550 B2 | 5/2012 | McAlister |
| 8,202,817 B2 | 6/2012 | Yuge et al. |
| 8,220,539 B2 | 7/2012 | Vinegar et al. |
| 8,318,100 B2 | 11/2012 | McAlister |
| 8,318,131 B2 | 11/2012 | McAlister |
| 8,318,269 B2 | 11/2012 | McAlister |
| 8,449,634 B2 | 5/2013 | Tamura et al. |
| 2002/0102188 A1 | 8/2002 | Hsu et al. |
| 2003/0008183 A1 | 1/2003 | Hsu |
| 2003/0178195 A1 | 9/2003 | Agee et al. |
| 2004/0084908 A1* | 5/2004 | Vu ................. 290/55 |
| 2004/0200618 A1 | 10/2004 | Piekenbrock |
| 2004/0219737 A1 | 11/2004 | Quon |
| 2004/0247957 A1 | 12/2004 | Hatano et al. |
| 2004/0253168 A1 | 12/2004 | Chu |
| 2004/0265448 A1 | 12/2004 | Shiau et al. |
| 2004/0266615 A1 | 12/2004 | Watson et al. |
| 2005/0029120 A1 | 2/2005 | Bar-Gadda |
| 2005/0061486 A1 | 3/2005 | Yang |
| 2005/0079977 A1 | 4/2005 | Choi et al. |
| 2005/0178125 A1* | 8/2005 | Skinnes et al. ............ 60/655 |
| 2005/0265919 A1 | 12/2005 | Lomax et al. |
| 2005/0272856 A1 | 12/2005 | Cooper et al. |
| 2006/0005738 A1 | 1/2006 | Kumar |
| 2006/0005739 A1 | 1/2006 | Kumar |
| 2006/0048808 A1 | 3/2006 | Ruckman et al. |
| 2006/0151027 A1* | 7/2006 | Pearson ................. 137/113 |
| 2006/0266043 A1* | 11/2006 | Jerome .................. 60/651 |
| 2007/0031718 A1 | 2/2007 | Fujimura et al. |
| 2007/0051118 A1* | 3/2007 | Stitou et al. ............... 62/101 |
| 2007/0065686 A1 | 3/2007 | Fan et al. |
| 2007/0138006 A1 | 6/2007 | Oakes et al. |
| 2007/0191664 A1 | 8/2007 | Hershkowitz et al. |
| 2007/0205298 A1 | 9/2007 | Harrison et al. |
| 2007/0220810 A1 | 9/2007 | Leveson et al. |
| 2007/0295477 A1 | 12/2007 | Mueller et al. |
| 2008/0073066 A1 | 3/2008 | Chang et al. |
| 2008/0086946 A1 | 4/2008 | Weimer et al. |
| 2008/0098654 A1 | 5/2008 | Cherry et al. |
| 2008/0170975 A1 | 7/2008 | Ahn et al. |
| 2008/0175766 A1 | 7/2008 | Mankins et al. |
| 2008/0241033 A1 | 10/2008 | Nazri |
| 2008/0295883 A1 | 12/2008 | Ducellier et al. |
| 2009/0062591 A1 | 3/2009 | Bingue et al. |
| 2009/0206666 A1 | 8/2009 | Sella et al. |
| 2009/0258278 A1 | 10/2009 | Steinberg |
| 2009/0313886 A1 | 12/2009 | Hinman et al. |
| 2010/0000874 A1 | 1/2010 | Hinman et al. |
| 2010/0043404 A1 | 2/2010 | Hebbale et al. |
| 2010/0107994 A1 | 5/2010 | Moriarty et al. |
| 2010/0140950 A1 | 6/2010 | Pitre |
| 2010/0174124 A1 | 7/2010 | Tonkovich et al. |
| 2010/0242352 A1 | 9/2010 | Perkins et al. |
| 2011/0061295 A1 | 3/2011 | McAlister |
| 2011/0061383 A1 | 3/2011 | McAlister |
| 2011/0100731 A1 | 5/2011 | Hassan |
| 2011/0197599 A1 | 8/2011 | Stewart et al. |
| 2011/0200516 A1 | 8/2011 | McAlister |
| 2011/0203776 A1 | 8/2011 | McAlister |
| 2011/0206565 A1 | 8/2011 | McAlister |
| 2011/0214986 A1 | 9/2011 | Brown |
| 2011/0220040 A1 | 9/2011 | McAlister |
| 2011/0239659 A1* | 10/2011 | Lior ................. 60/783 |
| 2011/0284298 A1 | 11/2011 | Ajisaka |
| 2011/0315539 A1 | 12/2011 | Zadik et al. |
| 2012/0118878 A1 | 5/2012 | Kim et al. |
| 2012/0119510 A1 | 5/2012 | Herzen et al. |
| 2013/0094909 A1 | 4/2013 | McAlister |
| 2013/0098035 A1 | 4/2013 | McAlister |
| 2013/0101492 A1 | 4/2013 | McAlister |
| 2013/0101502 A1 | 4/2013 | McAlister |
| 2013/0101908 A1 | 4/2013 | McAlister |
| 2013/0136658 A1 | 5/2013 | McAlister |
| 2013/0145761 A1 | 6/2013 | McAlister |
| 2013/0149208 A1 | 6/2013 | McAlister |
| 2013/0149621 A1 | 6/2013 | McAlister |
| 2013/0153399 A1 | 6/2013 | McAlister |
| 2013/0156504 A1 | 6/2013 | McAlister |
| 2013/0158828 A1 | 6/2013 | McAlister |
| 2013/0174486 A1 | 7/2013 | McAlister |
| 2013/0213256 A1 | 8/2013 | McAlister |

FOREIGN PATENT DOCUMENTS

| | | |
|---|---|---|
| CN | 101042261 A | 9/2007 |
| CN | 101091900 A | 12/2007 |
| CN | 101597025 A | 12/2009 |
| EA | 200702287 A1 | 4/2008 |
| EP | 1394103 A1 | 3/2004 |

(56) References Cited

FOREIGN PATENT DOCUMENTS

| | | |
|---|---|---|
| EP | 1658892 | 5/2006 |
| FR | 2923731 A1 | 5/2009 |
| GB | 24256 | 0/1911 |
| JP | 59046375 | 3/1984 |
| JP | S62203328 A | 9/1987 |
| JP | H02025571 | 1/1990 |
| JP | H04044314 | 2/1992 |
| JP | H0637348 | 5/1994 |
| JP | 0725637 | 3/1995 |
| JP | 0940491 | 2/1997 |
| JP | 09055374 | 2/1997 |
| JP | 10172960 | 6/1998 |
| JP | H11108465 A | 4/1999 |
| JP | 2000271472 A | 10/2000 |
| JP | 2000353690 A | 12/2000 |
| JP | 2001080902 A | 3/2001 |
| JP | 2001181846 A | 7/2001 |
| JP | 2001262353 A | 9/2001 |
| JP | 03215670 B2 | 10/2001 |
| JP | 2002158175 A | 5/2002 |
| JP | 2003040601 A | 2/2003 |
| JP | 2003166059 A | 6/2003 |
| JP | 2005511467 A | 6/2003 |
| JP | 2005021876 A | 1/2005 |
| JP | 2005213069 A | 8/2005 |
| JP | 2007139399 A | 6/2007 |
| JP | 2007150012 A | 6/2007 |
| JP | 2007208076 A | 8/2007 |
| JP | 2007527348 A | 9/2007 |
| JP | 2007254180 A | 10/2007 |
| JP | 2008503709 A | 2/2008 |
| JP | 2009010263 A | 1/2009 |
| JP | 2009500274 A | 1/2009 |
| JP | 2009513466 A | 4/2009 |
| JP | 2010003568 A | 1/2010 |
| JP | 2010006653 A | 1/2010 |
| JP | 2010025031 A | 2/2010 |
| JP | 2011507218 A | 3/2011 |
| KR | 100794943 B1 | 1/2008 |
| KR | 20120077307 A | 7/2012 |
| RU | 1776298 | 11/1992 |
| RU | 2011864 C1 | 4/1994 |
| RU | 2120913 C1 | 10/1998 |
| RU | 2312059 C1 | 12/2007 |
| RU | 2403379 C1 | 11/2010 |
| SU | 1498908 A1 | 8/1989 |
| WO | WO-2007053370 A2 | 5/2007 |
| WO | WO-2007140441 A2 | 12/2007 |
| WO | WO-2008031488 A1 | 3/2008 |
| WO | WO-2008035776 A1 | 3/2008 |
| WO | WO-2008076840 A2 | 6/2008 |
| WO | WO-2008093661 A1 | 8/2008 |
| WO | WO-2009098375 A1 | 8/2009 |
| WO | WO-2010097890 A1 | 9/2010 |
| WO | WO-2011154945 A2 | 12/2011 |

OTHER PUBLICATIONS

U.S. Appl. No. 13/684,743, filed Nov. 26, 2012, McAlister.
U.S. Appl. No. 13/832,740, filed Mar. 15, 2013, McAlister.
"Carnot Thermochemical Cycles." Digital image. Wikipedia, the Free Encyclopedia, Published: Aug. 31, 2010. Accessed: Jan. 4, 2011. Printed: May 20, 2011. <http://en.wikipedia.org/wiki/File:Carnot_thermochemical_cycles.PNG>. p. 1.
"Closed Loop Thermochemical Energy Storage System Using Ammonia." Australian National University College of Engineering & Computer Science—Solar Thermal Group. Accessed: Jan. 4, 2011. Printed: May 20, 2011. <http://solar-thermal.anu.edu.au/high-temperature/thermochemical-energy-storage/>. pp. 1-2.
"SI Cycle." Digital image. Sandia National Laboratories: Energy, Resources and Nonproliferation. Accessed: Jan. 4, 2011. Printed: Jun. 13, 2011. <http://www.sandia.gov/ERN/images/SI-cycle2.jpg>. p. 1.
"Solar Hydrogen." Digital image. Swiss Federal Institute of Technology, Department of Mechanical and Process Engineering, Zurich. Accessed: Jan. 4, 2011. Printed: May 23, 2011. p. 1. <http://www.pre.ethz.ch/research/projects/imgs/solarhydro_1.jpg>.
"The Carbon Cycle : Feature Articles." NASA Earth Observatory : Home. Web. Accessed: Jul. 1, 2010. Printed: Jun. 13, 2011. 12 Pages. <http://earthobservatory.nasa.gov/Features/CarbonCycle>.
"The Solar Zinc Route." Digital image. Swiss Federal Institute of Technology, Department of Mechanical and Process Engineering, Zurich. Accessed: Jan. 4, 2011. Printed: May 20, 2011. <http://www.pre.ethz.ch/research/projects/imgs/solzinc_1.jpg>. p. 1.
"Zinc Zinc-oxide Thermochemical Cycle." Digital image. Wikipedia, the Free Encyclopedia, Published: Dec. 21, 2008. Accessed: Jan. 4, 2011. Printed: May 20, 2011. <http://en.wikipedia.org/wiki/File:Zinc_zinc-oxide_thermochemical_cycle.jpg>. p. 1.
Chen et al. "Parylene-Encapsulated Copolymeric Membranes as Localized and Sustained Drug Delivery Platforms." Annals of Biomedical Engineering, vol. 37, Issue 10 (Oct. 2009): pp. 2003-2017.
Chen et al. "Thermochemistry Concept Map." Teacherknowledge Wikispace, Published: Nov. 20, 2006. <http://teacherknowledge.wikispaces.com/file/view/Thermochemistry+concept+map+-+Extended.pdf>. p. 1.
Food and Agriculture Organization of the United Nations. "Carbon Sequestration Options under the Clean Development Mechanism to Address Land Degradation." World Soil Resources Reports. Rome, 2000. pp. 1-45.
Foust et al. "An Economic and Environmental Comparison of a Biochemical and a Thermochemical Lignocellulosic Ethanol Conversion Processes." Cellulose, vol. 16, Issue 4. Jun. 10, 2009. pp. 547-565.
Funk, James E. "Thermochemical Processes for the Production of Hydrogen from Water." College of Engineering, University of Kentucky, Lexington, Kentucky. 1975. pp. 1-9.
Hackett et al. "Evaluation of Conversion Technoloigy Processes and Products: Appendix A—Discussion of Thermochemical Process Definitions." University of California, Davis. Sep. 2004. pp. 1-7.
Kasting, James F. "The Carbon Cycle, Climate, and the Long-Term Effects of Fossil Fuel Burning." U.S. Global Change Research Information Office. 1998. Web. Accessed: Jul. 1, 2010. Printed: Jun. 13, 2011. <http://www.gcrio.org/CONSEQUENCES/vol4no1/carbcycle.html>.
U.S. Energy Information Administration."Greenhouse Gases—Energy Explained, Your Guide To Understanding Energy." Web. Accessed: Jul. 1, 2010. Printed: Jun. 13, 2011. 1 Pages. <http://www.eia.gov/energyexplained/index.cfm?page=environment_about_ghg>.
US Environmental Protection Agency. "Cap and Trade." Web. Accessed: Jul. 1, 2010. Printed: Jun. 13, 2011. <http://www.epa.gov/captrade/>.
US Environmental Protection Agency. "Carbon Dioxide—Geologic Sequestration | Climate Change—Greenhouse Gas Emissions | U.S. EPA". Web. Accessed: Jul. 1, 2010. Printed: Jun. 13, 2011. <http://www.epa.gov/climatechange/emissions/co2_geosequest.html>.
US Environmental Protection Agency. "Carbon Dioxide | Climate Change—Greenhouse Gas Emissions | U.S. EPA". Web. Accessed: Jul. 1, 2010. Printed: Jun. 13, 2011. 1 Page. <http://www.epa.gov/climatechange/emissions/co2.html>.
US Environmental Protection Agency. "EPA Preliminary Analysis of the Waxman-Markey Discussion Draft". Web. Accessed: Jul. 1, 2010. Printed: Jun. 13, 2011. <http://www.epa.gov/climatechange/economics/pdfs/WM-Analysis.pdf>.
Elias et al., "Control of Graphene's Properties by Reversible Hydrogenation: Evidence for Graphene", Science, vol. 23, 2009, pp. 610-613.
International Search Report and Written Opinion for PCT Application No. PCT/US2012/050671; Date of Mailng: Dec. 27, 2012; 10 pages.
Solar Collectors, Energy Storage, and Materials, pp. 443-444 (DeWinter, Francis, 1991).
Wikipedia > Aerogel > Carbon - "Carbon aerogels are also extremely 'black' in the infrared spectrum, reflecting only 0.3% of radiation between 250 nm and 14.3 μm, making them efficient for solar energy collectors," 1 page, 2013.

(56) References Cited

OTHER PUBLICATIONS

Vegners, Raimonds Maris; "Collodial Carbon and Silica : Their Use in Solar Energy" Table of Contents and Introduction of Thesis, University of Sydney, Feb. 1985, 5 pages.

International Search Report and Written Opinion for PCT Application No. PCT/US2014/015889; Date of Mailing; May 19, 2014; 10 pages.

N. Muradov: "Catalysis of Methane decomposition over elemental carbon", Catalysis Communications, No. 3-4, Jul. 1, 2001, pp. 89-94, p. 89, right-hand column, paragraph 2.

Muradov et al: "Catalytic Dissociation of Hydrocarbons: a Route to $CO_2$-free Hydrogen", 15th Annual Symposium on Catalysis in Petroleum Refining & Petrochemicals, 2005.

\* cited by examiner

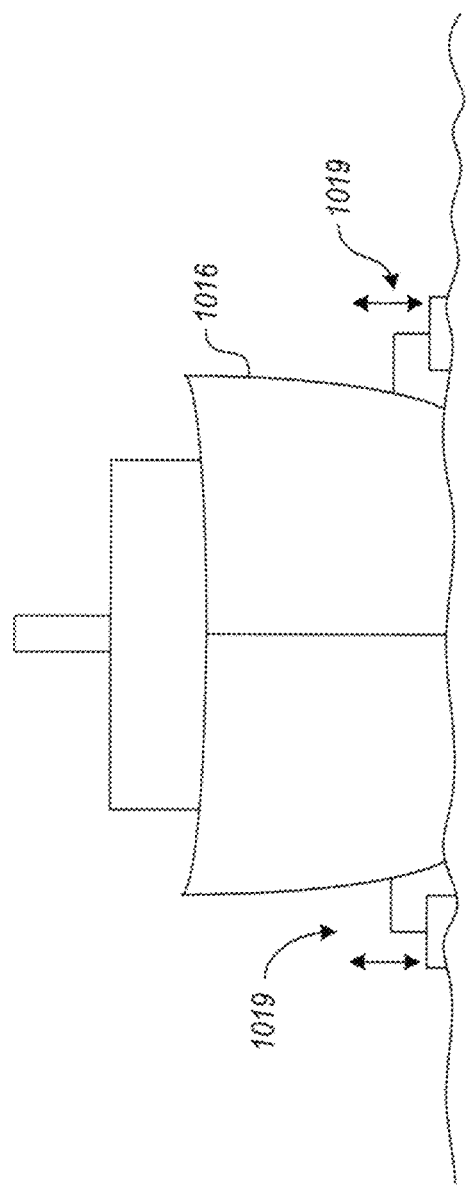

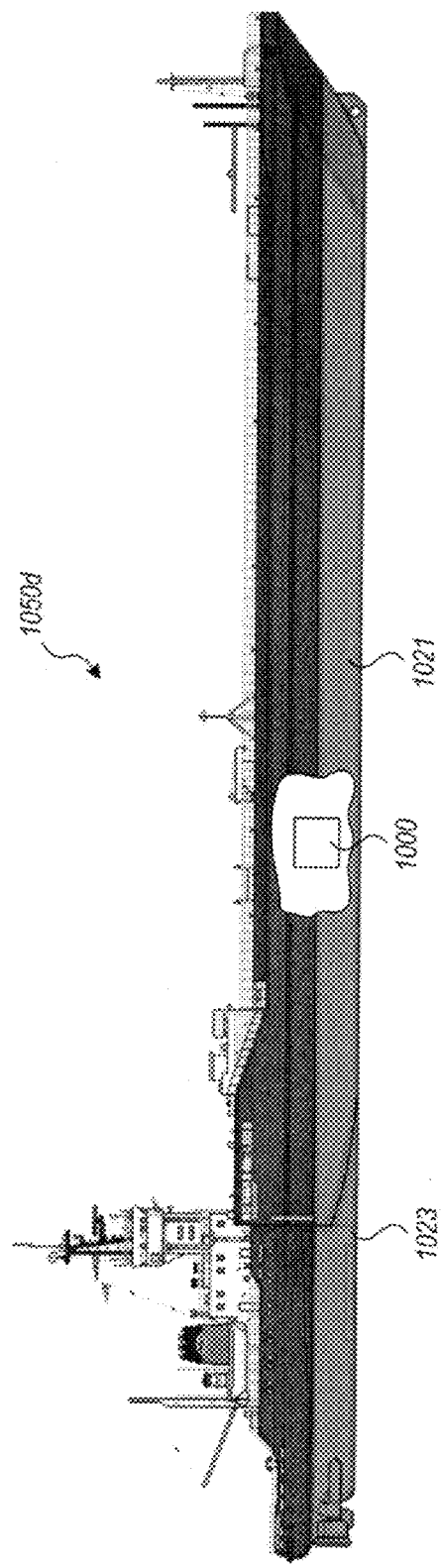

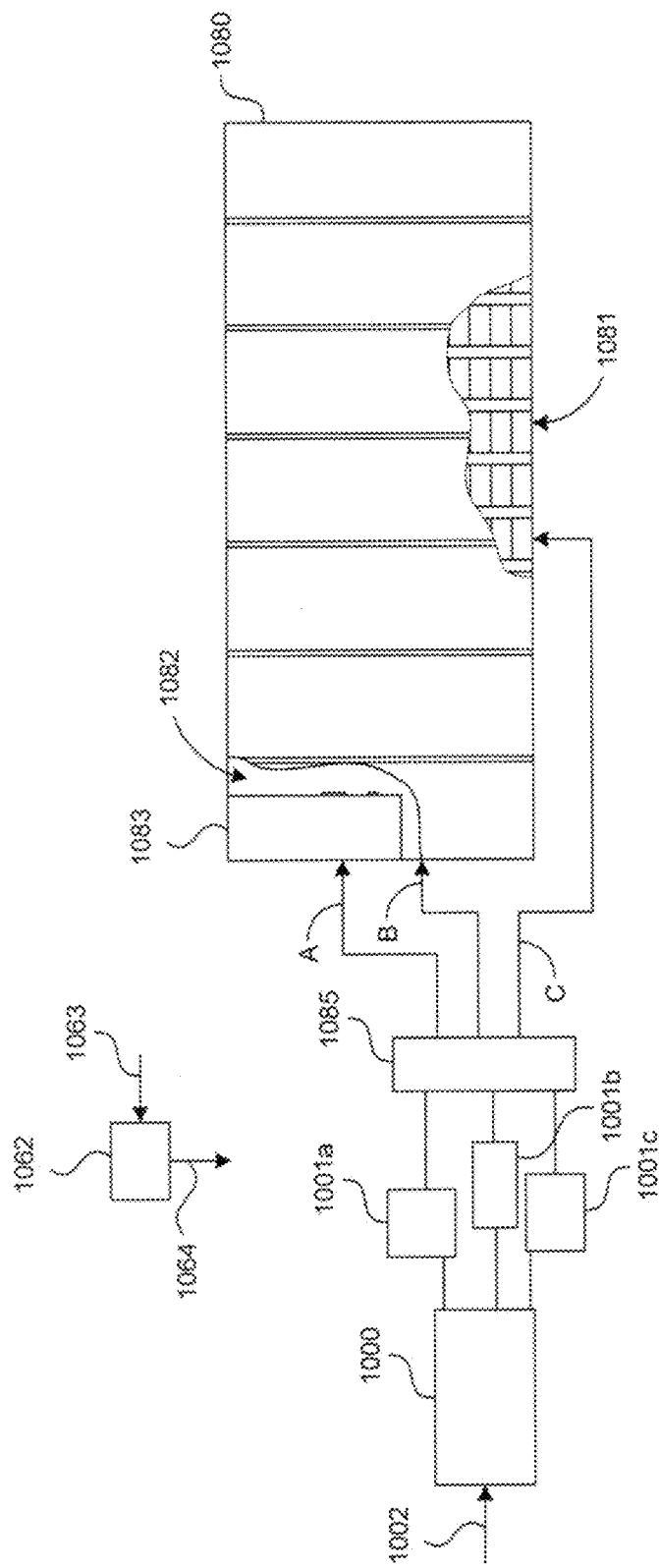

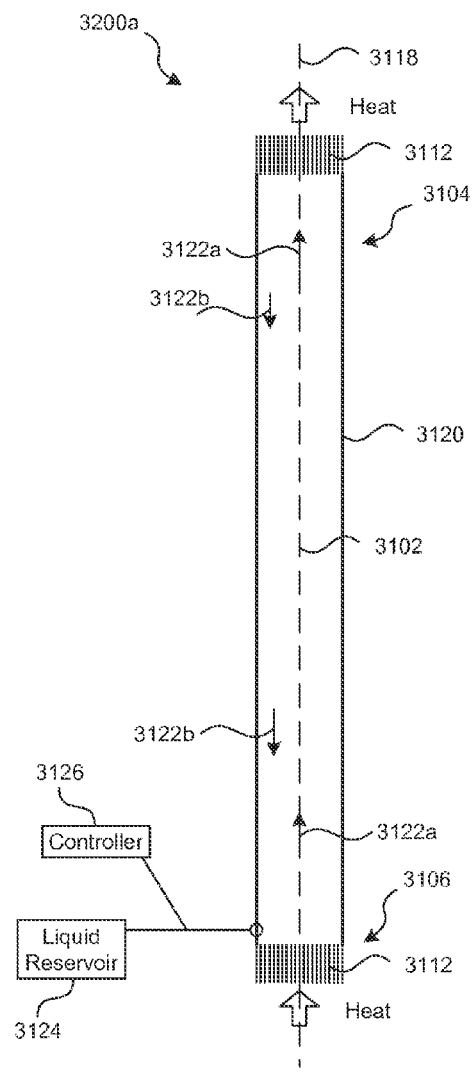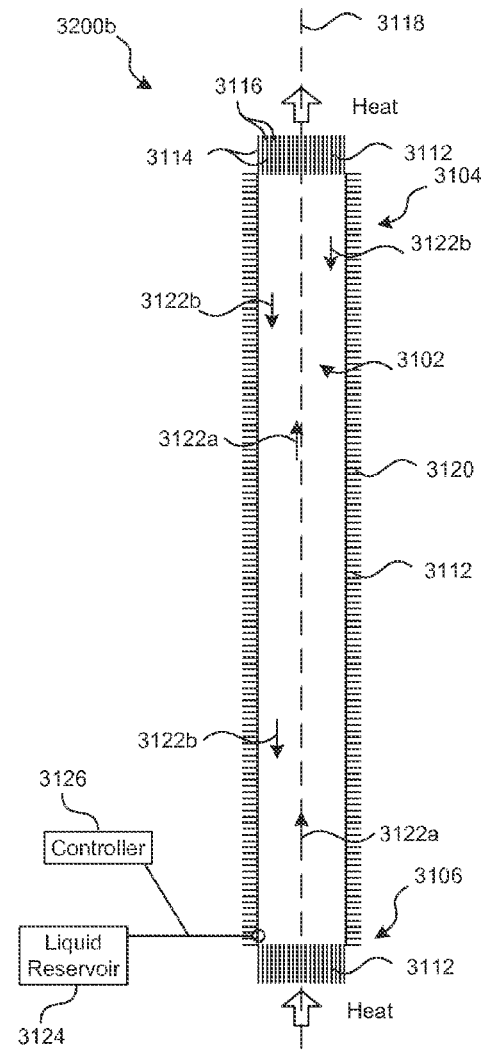
*FIG. 17B*        *FIG. 17C*

US 8,911,703 B2

REDUCING AND/OR HARVESTING DRAG ENERGY FROM TRANSPORT VEHICLES, INCLUDING FOR CHEMICAL REACTORS, AND ASSOCIATED SYSTEMS AND METHODS

CROSS-REFERENCE TO RELATED APPLICATION

The present application is a continuation-in-part of pending U.S. application Ser. No. 13/584,786, filed Aug. 13, 2012, which claims priority to U.S. Provisional Application 61/522,909, filed Aug. 12, 2011 and incorporated herein by reference. To the extent the foregoing provisional application and/or any other materials incorporated herein by reference conflict with the present disclosure, the present disclosure controls.

TECHNICAL FIELD

The present disclosure is directed generally to reducing and/or harvesting drag energy from transport vehicles, and associated systems and methods. In particular embodiments, aerodynamic braking is regeneratively used to provide power to the vehicle, and/or to provide power for on-board chemical reactors.

BACKGROUND

Large vehicles such as freight hauling trucks with eighteen wheels and inflated rubber tires encounter multiple sources of resistance, which reduce the efficiency with which these vehicles operate. One source of resistance is the rolling resistance between the truck tires and the road surface. A second source of energy loss results from the mechanical friction of internal engine and drive train components. A third source is aerodynamic drag or "windage" losses.

Mechanical friction can dominate other losses at low speeds. For example, when a large truck starts up, the main losses are various friction losses due to the relative motion of the mechanical components of the truck. As the truck speed increases, the power required to overcome the mechanical resistance of engine components, transmission and wheel bearings and tires is roughly proportional to the ground speed, and thus the energy expended is nearly constant after the lubricating oils, seals, bearings and tires reach a steady state temperature condition.

The power required to overcome air resistance increases as a function of the cube of the relative air speed, and the energy expended per mile traveled is proportional to the square of the relative speed. Thus, at speeds above about 30 miles per hour (MPH), overcoming air resistance becomes the largest power requirement for freight delivery vehicles.

Box-like trucks without streamlining (e.g., a typical tractor-trailer truck combination) traveling at 45 MPH require about ⅓ as much power and expend about ½ as much energy per mile as is required to travel at 65 MPH. Increasing the relative air speed of the vehicle, such as traveling against a 25 MPH head wind at a 65 MPH ground speed (to produce a 90 MPH relative air speed), requires about 2.6 times greater power and 1.9 times greater energy expenditure.

Hybrid vehicles, e.g., automobiles with regenerative braking systems that substantially rely upon battery-powered electric propulsion, generally provide greater fuel economy in stop-and-go city driving than at higher air-resistance conditions during highway travel. The opposite result of better highway fuel economy at moderate highway speeds as opposed to start-and-stop driving conditions applies to vehicles without such regenerative braking. Wind resistance above relative speeds of about 55 MPH overcomes the constant velocity advantage, and fuel economy at 70 MPH is generally 25 to 30% less than at 55 MPH for stylized passenger cars with various degrees of streamlining to reduce air resistance.

Several vehicles have achieved greater fuel economy at 65 MPH than at lower speeds. For example, conventional internal combustion engine propulsion systems (non-hybrid drive trains) in vehicles such as the 1994 Oldsmobile Cutlass achieved better fuel economy of 25 MPG at 65 MPH as compared to 23 MPG at 45 MPH. In a similar example, the 1997 Toyota Celica achieved 43.5 MPG at 65 MPH as compared to 42.5 MPG at 55 MPH.

Streamlining "large box" delivery vehicles and heavy freight trucks has taken the form of introducing various degrees of surface rounding to reduce the relative-motion wind forces. Manufacturers and operators, however, generally oppose the loss of cargo packing efficiency and space that rounding the corners of the truck "boxes" requires. At least some conventional components for reducing the air pressure and drag in various locations of the truck have been introduced. Such approaches are cumbersome and have been found to actually increase drag, and/or cause vehicle steering uncertainties, and/or contribute to collisions and rollovers at the onset of some travel conditions, particularly crosswinds.

FIG. 1 shows a conventional approach for adding features to round the tractor surfaces, along with added structures that blend the streamlining of the tractor with the surfaces of the cargo trailer. This provides drag reduction by streamlining the flow the air up and over the freight box. Rounding the vertical edges of the freight box can further reduce drag. However, these efforts to reduce energy losses tend to add curb weight. In addition, streamlining can add cross-sectional area (which increases cross-wind forces), and adds to the initial cost of the vehicle. These factors can result in unattractive recovery projections compared to competing opportunities for improving engine efficiency, reducing maintenance and/or eliminating emission control measures.

Braking represents another area of vehicle operation that creates waste energy. Conventional brakes typically convert kinetic energy to heat, which is then dumped. In other conventional arrangements, "jake braking" uses the back pressure available from the vehicle's engine cylinders to provide braking force by restricting the exhaust. In still further conventional arrangements mechanical/electrical regenerative braking is used to slow the vehicle by driving a generator operably coupled to the vehicle wheels during braking. In any of the foregoing arrangements, the braking processes produce waste energy that reduces the efficiency of the vehicle.

For at least the foregoing reasons, there exists a need in the relevant art for more efficient transport systems, and more efficient use of natural resources.

BRIEF DESCRIPTION OF THE DRAWINGS

FIGS. 10A-E illustrate mobile transport platforms having reactors and/or other systems in accordance with embodiments of the present disclosure.

FIG. 11 is a schematic illustration of a system for refrigerating and/or otherwise preserving cargo in accordance with embodiments of the presently disclosed technology.

FIGS. 17B and 17C are schematic cross-sectional views of thermal transfer devices configured in accordance with other embodiments of the present technology.

DETAILED DESCRIPTION

1. Overview

Figure 1:
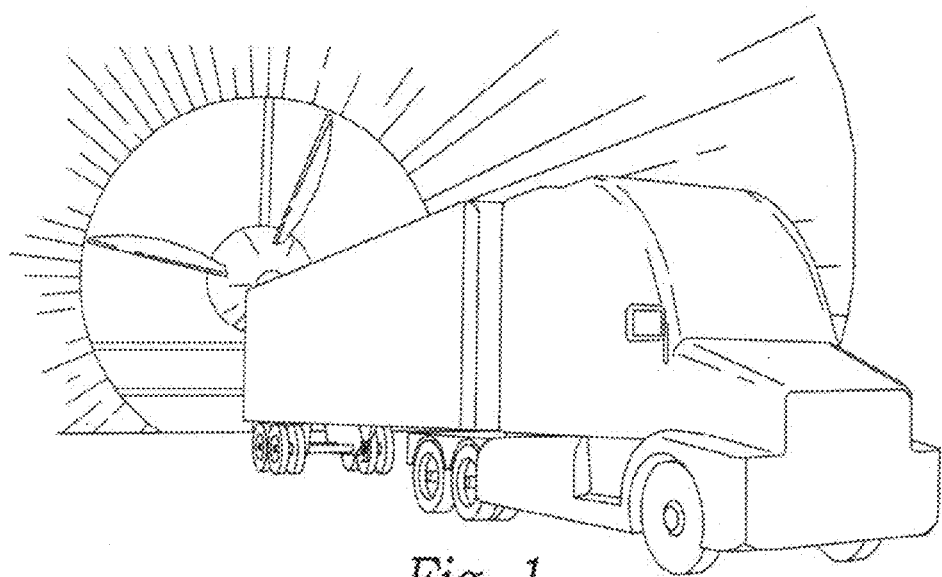
FIG. 1 is an illustration of a streamlined truck assembly configured in accordance with the prior art.

Several examples of devices, systems and methods for capturing otherwise wasted energy on a transport platform (e.g., a vehicle), streamlining the transport platform, and/or using the captured energy to conduct reactions in thermochemical processing (TCP) reactors are described below. The transport platforms can include trucks, trains, marine vessels and/or other transportation systems. The TCP reactors can be used in accordance with multiple operational modes to reform or dissociate a hydrogen donor (e.g., methane) into hydrogen and other donor products. The dissociated products can be used to produce electrical energy, hydrogen fuels, carbon products, and/or other useful end products. Accordingly, the TCP reactors can produce clean-burning fuel and can re-purpose carbon and/or other constituents for use in durable goods, including polymers and carbon composites. In other embodiments, the techniques and devices for controlling extracting, harvesting and/or re-using energy are implemented without a TCP reactor. Although the following description provides many specific details of representative examples in a manner sufficient to enable a person skilled in the relevant art to practice, make and use them, several of the details, processes, and advantages described below may not be necessary to practice certain examples of the technology. Additionally, the technology may include other examples that are within the scope of the claims but are not described here in detail.

References throughout this specification to "one example," "an example," "one embodiment" or "an embodiment" mean that a particular feature, structure, process or characteristic described in connection with the example is included in at least one example of the present technology. Thus, the occurrences of the phrases "in one example," "in an example," "one embodiment" or "an embodiment" in various places throughout this specification are not necessarily all referring to the same example. Furthermore, the particular features, structures, routines, steps or characteristics may be combined in any of a number of suitable manners in one or more examples of the technology. The headings provided herein are for convenience only and are not intended to limit or interpret the scope or meaning of the disclosed technology.

Certain embodiments of the technology described below may take the form of computer-executable instructions, including routines executed by a programmable computer or controller. Those skilled in the relevant art will appreciate that the technology can be practiced on computer or controller systems other than those shown and described below. The technology can be embodied in a special-purpose computer, controller, or data processor that is specifically programmed, configured or constructed to perform one or more of the computer-executable instructions described below. Accordingly, the terms "computer" and "controller" as generally used herein refer to any data processor and can include Internet appliances, hand-held devices, multi-processor systems, programmable consumer electronics, network computers, mini-computers, and the like. The technology can also be practiced in distributed environments where tasks or modules are performed by remote processing devices that are linked through a communications network. Aspects of the technology described below may be stored or distributed on computer-readable media, including magnetic or optically readable or removable computer discs as well as media distributed electronically over networks. In particular embodiments, data structures and transmissions of data particular to aspects of the technology are also encompassed within the scope of the present technology. The present technology encompasses methods of both programming computer-readable media to perform particular steps, and executing the steps.

2. Representative TCP Reactors and TCP Reactor System

Figure 2:
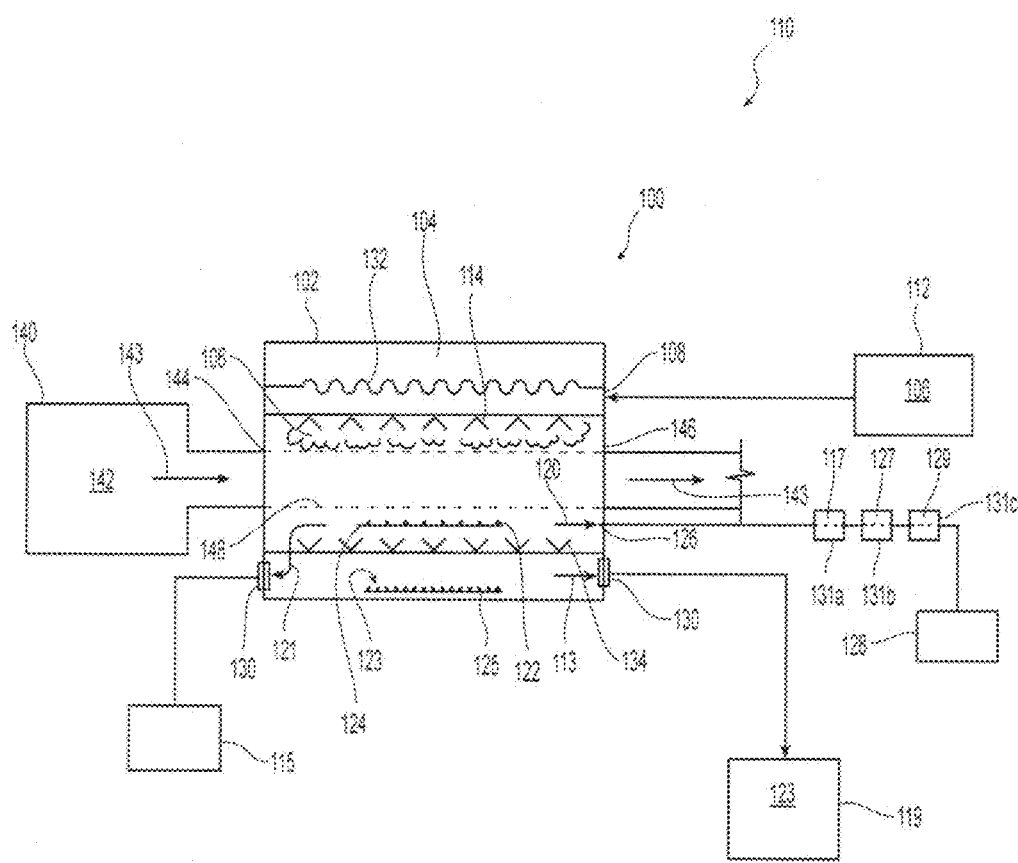
FIG. 2 is a partially schematic, cross-sectional illustration of a thermal chemical processing (TCP) reactor system suitable for a mobile transport platform in accordance with several embodiments of the presently disclosed technology.

FIG. 2 is a partially schematic illustration of a representative TCP reactor 100 and reactor system 110. Further representative TCP reactors and reactor systems are described in detail in U.S. patent application Ser. No. 13/027,208, titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS," filed Feb. 14, 2011, incorporated herein by reference and referred to as the '208 Application. As illustrated, the representative reactor 100 has a reactor vessel 102 configured and insulated to provide control of reaction conditions, including an elevated temperature and/or pressure within the interior of a reactor chamber 104, sufficient to reform or dissociate a donor substance 106 introduced into the reactor 100. The reforming or dissociation processes are non-combustive processes and can be conducted in accordance with the parameters described in the '208 Application previously incorporated herein by reference. The reactor system 110 can include heat exchangers, heaters, piping, valves, sensors, ionizers, and other equipment (not shown in FIG. 2) to facilitate introducing the donor substance 106 into the TCP reactor 100, to facilitate reforming, respeciating and/or dissociating the donor substance 106 within the reactor 100, and to facilitate extracting dissociated and/or reformed components of the donor substance 106 from the reactor 100.

The reactor chamber 104 includes one or more donor inlets 108 for receiving the donor substance 106 from a donor source 112. In particular embodiments, the donor substance 106 is a hydrogen donor and can be a solid, liquid and in further embodiments a gaseous hydrocarbon, e.g., methane gas. The donor substance 106 can include other carbon-based compounds, e.g., ethane, propane or butane, along with cetane and/or octane rated compounds. In still further embodiments, the donor substance 106 can include a lower grade constituent, e.g., off-grade cetane or octane rated hydrocarbons, or wet alcohol. In at least some embodiments, the donor substance can include compounds other than hydrocarbon fuels (e.g., carbohydrates, fats, alcohols, esters, cellulose and/or others). In yet further embodiments, the hydrogen donor 106 can include hydrogen atoms in combination with constituents other than carbon. For example, nitrogenous compounds (e.g., ammonia and/or urea) can serve a similar hydrogen donor function. Examples of other suitable hydrogen donors are described in the '208 Application, previously incorporated herein by reference. In yet further embodiments, the donor substance can donate constituents other than hydrogen. For example, the reactor 100 can dissociate oxygen from $CO_2$ and/or another oxygen donor, or the reactor 100 can dissociate a halogen donor. The donor substance 106 can be in a gaseous or liquid form that is distributed into the reactor chamber 104 through donor inlet nozzles 114. Typically, the donor substance 106 is provided as a vapor or gas. In other embodiments, the donor substance 106 can be a liquid or vapor that undergoes a gas phase transition in the reactor chamber 104.

In the reactor chamber 104, the donor substance 106 undergoes reformation, partial oxidation and/or a non-combustion-based dissociation reaction and dissociates into at least two components, e.g., a gas 120 and a solid 122. In other embodiments, the dissociated components can take the form of a liquid and a gas, or two gases, depending on the donor substance used and the dissociation process parameters. In further embodiments, the donor substance 106 can dissociate into three or more dissociated components in the form of a solid, gas, or liquid, or a mixture of these phases. In a particular embodiment, methane is the donor substance, and the dissociated components are carbon and hydrogen.

When carbon is a dissociated component, it can be disposed as a solid 122 on an internal donor solid (e.g., carbon) collector 124 within the reactor chamber 104, and when hydrogen is a dissociated component, it can be in the form of a gas 120 within the reaction chamber 104. The carbon can be transferred from the internal collector 124 to an industrial manufacturing or packaging plant via a storage tank or other receptacle 115 as shown by arrow 121. The hydrogen gas can react with carbon dioxide from sources such as a combustion chamber 140 and/or the donor source 112 for production of fluids such as selected alcohols and/or water. In other embodiments, the hydrogen and carbon can be removed from the reaction chamber 104 together (e.g., in gaseous forms such as $H_2$ and CO and/or $CO_2$ and/or $CH_3OH$ and/or $C_2H_5OH$, among others) and separated outside the reaction chamber 104. Substances such as hydrogen 117, carbon monoxide 127, and water 129 can be collected by selective filtration, pressure or temperature swing adsorption and/or phase separation processes in separation/collection subsystems (e.g., collectors) 131a, 131b and 131c. Any remaining constituents can be collected at an additional collector 128. Products at elevated temperature can exchange heat with the donor substance (e.g., feed stocks) 106 to cool the outgoing products and heat the incoming reactants. As described above, in many of these embodiments, the donor substance functions as a hydrogen donor, and is dissociated into molecules of hydrogen (or a hydrogen compound) and molecules of the donor (or a donor compound).

In addition to removing the reaction products to access the products for other purposes, the reaction products can be removed in a manner and/or at a rate that facilitates the reaction taking place in the reactor chamber 104. For example, solid products (e.g., carbon) can be removed via a conveyor, and fluids (gases and/or liquids) can be removed via a selective filter or membrane to avoid also removing reactants. As the products are removed, they can exchange heat with the incoming reactants, as discussed above. In addition to pre-heating the reactants, this process can contract and/or change the phase of the products, which can further expedite the removal process and/or control (e.g., reduce) the pressure in the reaction chamber 104. In a particular embodiment, condensing water and/or alcohols from the product stream can achieve this purpose. In any of these embodiments, removing the reactants quickly rather than slowly can increase the rate and/or efficiency of the reaction conducted in the chamber 104.

In at least some embodiments, substances such as energy crops, forest slash, landfill waste and/or other organic wastes can be transferred into the reactor chamber 104, e.g., via the donor inlet 108, and can be anaerobically heated to produce gases such as methane, water vapor, hydrogen, and carbon monoxide. This process and/or other processes can create ash, which, if allowed to accumulate, can interfere with radiative heating and/or other processes within the reactor chamber 104. Accordingly, an ash residue 123 can be collected at an ash collector 125 and transferred to an external ash collector or receptacle 119 (as indicated by arrow 113) for various uses such as returning trace minerals to improve crop productivity from hydroponic operations or soil, or as a constituent in concrete formulas. The ash collector 125 can be cooled and/or positioned to selectively attract ash deposits as opposed to other products and/or reactants. In at least some embodiments, the ash may also contain char, which can also be collected. In general, the amount of ash and/or char introduced to and removed from the reactor 100 depends in part on the composition of the donor 106, with relatively simple and/or pure donors (e.g., pure methane) producing little or no ash and char. In any of these embodiments, an advantage associated with collecting the ash within the reactor chamber 104 rather than from the products exiting the chamber is that the ash is less likely to contaminate, foul and/or otherwise interfere with the efficient operation of the reactor 100. Benefits of the present embodiments include an increased tolerance regarding the rate with which the ash 123 is produced and/or removed from the reactor chamber 104. As a result, the ash may have little or no effect on the reaction rate in the chamber 104, and so may not be controlled as closely as the product removal rate.

The reaction chamber 104 includes one or more reaction chamber exit ports 126 (one is shown schematically in FIG. 2) through which gaseous or liquid dissociated components can be removed and delivered for subsequent processing or containment. The donor inlet nozzle 114, donor solid collector 124, and reaction chamber exit port 126 can be positioned to enhance (e.g., maximize) the movement of the donor substance 106 and dissociated components 120 and 122 through the reaction chamber 104, so as to facilitate accumulating and removing the dissociated components from the TCP reactor 100. The TCP reactor 100 can also include one or more solid collector exit ports 130 (two are shown in FIG. 2) through which the solid dissociated component 122 and/or ash 123 can be removed from the reactor 100. Representative carbon-based products from the reactor 100 include carbon, silicon carbide, halogenated hydrocarbons, graphite, and graphene. These products can be further processed, e.g., to form carbon films, ceramics, semiconductor devices, polymers and/or other structures. Accordingly, the products of the reaction conducted in the reactor 100 can be architectural constructs or structural building blocks that can be used as is or after further processing. Other suitable products are described in the '208 Application.

As described above, the TCP reactor 100 can be configured to facilitate the ingress of the donor substance 106 into the reactor chamber 104, and to permit the egress of materials, including the dissociated components 120 and 122 from the reactor chamber, e.g., as summarized in Equation 1 below. The TCP reactor 100 can also receive additional thermal energy provided by a heater 132 via concentrated solar energy or regenerative electric heating or by circulating heat transfer fluids. At times when solar, wind, hydroelectric, geothermal or another off-peak energy is available in excess of the demand for operating the system 110, energy (e.g., heat energy) can be stored in an insulated heat battery or transferred into a heated water storage medium. In particular embodiments, the TCP reactor 100, and the TCP reactor system 110 as a whole, can be configured to permit the ingress or egress of additional substances and/or energy into or out of the reaction chamber 104. These additional substances and/or energies can be applied to modify the operation of the TCP reactor 100 so as to accept different donor substances, to provide different dissociated and/or reformed components, to provide greater control over the dissociation reaction, and/or to provide greater efficiency in the operation of the TCP reactor system.

In the representative system of FIG. 2, a reactant distributor 134 for additional reactants e.g., water (steam), is disposed in the reaction chamber 104 to provide supplemental heat and/or constituents. Water in the reaction chamber 104 can also participate in reactions such as reforming steam and methane into the products shown in Equation 2 below. Accordingly, Equations 1 and 2 illustrate representative dissociation and reformation processes without water (or another oxygen donor) as a reactant and with water (or another oxygen donor, e.g., air) as a reactant:

$$CH_4 + HEAT_1 \rightarrow C + 2H_2 \tag{1}$$

$$CH_4 + H_2O + HEAT_2 \rightarrow CO + 3H_2 \tag{2}$$

In a particular embodiment shown in FIG. 2, the combustion chamber 140 directs combustion products 142 into the reaction chamber 100 through a combustion product inlet 144 as indicated by arrow 143. The heat-emitting combustion products 142 pass through the reactor 100 so as to provide additional heat to the reactor chamber 104 and exit via an outlet 146. The combustion products inlet 144 and outlet 146 can be joined by a pipe or conduit 148 that facilitates transferring heat from the combustion products 142 into the reaction chamber 104 and that, in particular embodiments, allows some or all of the combustion products 142 to enter the reaction chamber 104 through a permeable or transmissive surface of the conduit 148. Such products can include steam and/or oxides of carbon, nitrogen, and/or oxygen, and such surfaces are described further in U.S. application Ser. No. 13/026,996, titled "REACTOR VESSELS WITH TRANSMISSIVE SURFACES FOR PRODUCING HYDROGEN-BASED FUELS AND STRUCTURAL ELEMENTS, AND ASSOCIATED SYSTEMS AND METHODS," filed Feb. 14, 2011 and incorporated herein by reference. Accordingly, the combustion products 142 can supplement the donor substance 106 as a source of hydrogen and/or donor molecules. In further embodiments, the reactor 100 can also include one or more heat exchangers (e.g., counterflow heat exchangers) as described in the '208 Application. In any of these embodiments, sufficient heat is transmitted to the reactor 100 to enable the non-combustion dissociation reaction that separates the donor substance 106 into the donor-based component and hydrogen or hydrogen-based component.

Reactors having any of the foregoing configurations can be used to process substances obtained from a number of liquid, vapor, and/or gas producing sites. Representative sites include a landfill where organic action has produced recoverably valuable quantities of methane and/or carbon dioxide, the sea floor (holding frozen methane hydrates subject to mobilization such as via thawing), permafrost, deposits of degrading limestone that release carbon dioxide, anaerobically digested paper and/or paper products, and stranded well gas. Reactors processing the gases provided from such sites, and/or other sites, require heat to facilitate the non-combustion reaction, dissociation, and/or hydrolytic reactions. The necessary heat may be obtained in whole or in part from solar, wind, geothermal and/or other sources. Representative techniques for providing energy to a mobile TCP reactor and/or harnessing and/or controlling energy in the adjacent airflow are described below with reference to FIGS. 3-10E.

3. Representative Transport Platforms with Streamlining and/or TCP Features

FIGS. 3-10E, described below, illustrate mobile transport platforms that can include reactors having some or all of the features described above with reference to FIG. 2. At least some of the mobile transport platforms can include systems that extract energy and/or improve the efficiency of the mobile transport platform, with or without an on-board reactor. Accordingly, depending upon the particular embodiment, representative transport platforms in accordance with the present technology can include any of a wide variety of suitable combinations of reactors in combination with any of a variety of energy extraction and/or efficiency-enhancing subsystems. In other embodiments, the mobile transport platform can include such subsystems without a thermochemical reactor of the type described above with reference to FIG. 2. Whether or not a particular embodiment is selected for implementation depends at least in part upon the particular mobile transport platform and/or the manner in which the mobile transport platform is to be used. Accordingly, the present disclosure is suitable for one of ordinary skill in the art to make and use a variety of such combinations, even if such combinations are not expressly illustrated together in the following Figures.

Figure 3:
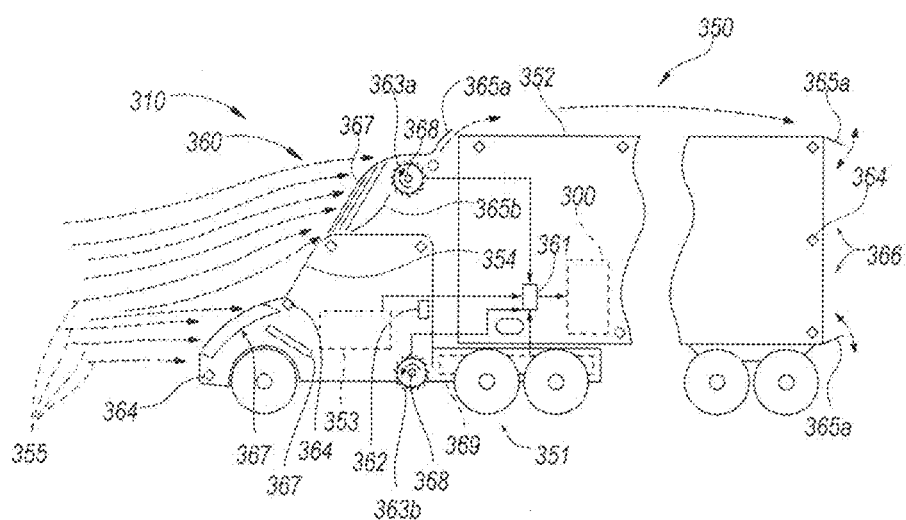
FIG. 3 is a schematic side view of a mobile transport platform that includes a tractor-trailer combination having an energy extraction system in accordance with an embodiment of the present disclosure.

FIG. 3 is a schematic side view of an overall system 310 that includes a mobile transport platform 350. The mobile transport platform 350 further includes an energy extraction system 360 configured in accordance with a particular embodiment of the present disclosure. In one aspect of this embodiment, the mobile transport platform 350 includes a tractor-trailer combination, e.g., a tractor 351 releasably coupled to a trailer 352. For purposes of illustration, several features of the system 310 are shown as being carried by the tractor 351 or the trailer 352. In other embodiments, the features carried by the tractor 351 can instead be carried by the trailer 352, and/or vice versa. In still further embodiments, only the tractor 351 or only the trailer 352 carries such features. In yet further embodiments, one or more features of the system 310 are carried by a container (e.g., a 40-foot or other size multi-modal container) that is in turn carried by the trailer 352. Accordingly, the container, with the system 310 on board can be transported by the tractor 351 and/or other propulsion units. Suitable propulsion units include ships, tugs and trains, as are described in greater detail later. Accordingly, the disclosed features can be combined in any of a wide variety of suitable configurations.

As shown in FIG. 3, the mobile transport platform 350 includes a thermochemical processing reactor 300, e.g., of the type described above with reference to FIG. 2. The energy extraction system 360 can provide energy to the reactor 300 and/or other subsystems of the platform 350.

In a particular embodiment, the energy extraction system 360 includes one or more turbines 363, illustrated as a first turbine 363a positioned above a windshield 354 of the tractor 351, and a second turbine 363b positioned below the windshield 354. Further embodiments of representative turbines and associated components are described in co-pending U.S. patent application Ser. No. 12/857,433, filed Aug. 16, 2010 and incorporated herein by reference. Each of the turbines 363 can rotate about a rotation axis 368 that can be at any suitable orientation, for example, generally transverse to the tractor's direction of travel. The turbines 363 can include fixed blades or variable pitch blades for additional control capability. Each of the turbines 363 is positioned to extract energy from the airstream 355 through which the transport platform 350 passes, and provide the energy for use by the reactor 300 and/or other vehicle subsystems.

In a particular embodiment, the energy extracted by the energy extraction system 360 is first provided to an energy storage unit 361, which in turn directs the energy to the reactor 300 and/or other vehicle subsystems. For example, the energy storage unit 361 can include a battery that receives power not only from the energy extraction system 360, but also from the main propulsion engine 353 of the mobile transport platform 350, and/or from a regenerative braking system 369 that extracts energy from the wheels of the tractor 351 and/or the trailer 352 during braking. In other embodiments, any of these systems can provide energy directly to the reactor 300 and/or to other vehicle subsystems, thus bypassing or eliminating the need for the energy storage unit 361. In still further embodiments, the energy storage unit 361 can include devices in addition to or in lieu of the battery described above. For example, the energy storage unit 361 can include a heat battery, a flywheel, a pressurized fluid system (e.g., air or liquid), a hydraulic system, a capacitor, and/or other suitable energy storage devices or combinations of any of the foregoing devices. The heat battery can be heated to store energy that is exchanged, as needed, with a suitable fluid, e.g., water, fuel or air.

The transport platform 350 can also include multiple sensors 364 positioned at suitable locations of the platform 350, including external surfaces, internal surfaces, and/or with system components. The sensors 364 are positioned to detect any of a wide variety of suitable vehicle parameter values, for example, external wind velocity and direction, external and/or internal temperatures, humidities, fluid flow rates, velocities and/or loads, among other values. The sensors 364 can be coupled to a controller 362 (shown schematically in FIG. 3) which directs the operation of the energy extraction system 360, the reactor 300, the energy storage unit 361, and/or other subsystems and components of the platform 350, based at least in part on information received from the sensors 364.

The energy extraction system 360 can include a variety of actuatable elements 366 for controlling and/or directing airflow and/or for other functions. For example, the energy extraction system 360 can include one or more airflow directors 365, illustrated as external airflow directors 365a and internal airflow directors 365b. The airflow directors 365 can direct flow around the mobile platform 350, toward other energy extraction features, and/or in other manners, depending upon the particular mode of operation in which the transport platform and/or the energy extraction system 360 are placed. For example, the external flow directors 365a at the rear of the trailer 352 can be adjusted to reduce the base or boattail drag of the trailer 352. An external flow director 365a toward the top of the tractor 351 can direct flow exiting the upper turbine 363a, and an internal flow director 365b can direct airflow to the lower turbine 363a.

The energy extraction system 360 can also include louvers 367 or other devices that can, in addition to directing the airflow, open or close flow avenues, again depending upon the mode of operation. For example, the energy extraction system 360 can include louvers 367 positioned upstream of the turbines 363a, 363b to selectively direct air toward or away from the turbines 363 and/or to regulate the amount of air directed to each of the turbines 363. When the louvers 367 are open, they operate to re-direct air in front of the tractor 351 to reduce air pressure build-up. Whether the air is then directed to a turbine 363 (or other energy extraction device) or not, the louvers 367 can be operated and controlled to enhance stability and control of the mobile transport platform 350. For example, louvers 367 on one side of the transport platform 350 can be activated while louvers on the opposite side of the transport platform 350 are not activated, or are activated in a different manner. This mode of operation can be used to aid in stabilizing the vehicle (e.g., in a cross-wind) and/or aid in steering the vehicle. Louvers 367 toward the top of the transport platform 350 can be operated differently than those toward the bottom, e.g., to increase airflow under the platform 350. Further details of representative operations are described later with reference to FIGS. 4A-C.

In addition to or in lieu of using the turbines 363 to generate power for the reactor 300 and/or other vehicle systems, the turbines 363 can be used as an aerodynamic regenerative brake. In this arrangement, the turbines 363 can be used in addition to or in lieu of conventional brakes and/or the regenerative braking system 369 that operates on the vehicle wheels. Rather than operating on the vehicle wheels, the turbines 363 can extract energy from the adjacent airstream in a manner that regeneratively slows the transport platform 350. In particular, the forces imparted to the turbines 363 when extracting energy from the airstream (and particularly when the turbines 363 are driving a load, such as an electric generator) are directed at least in part opposite the platform direction of travel. Accordingly, the turbines 363 can be actively adjusted to provide a braking function or an increased braking function on demand. For example, in response to a brake request (e.g., the operator's foot on a brake pedal), the pitch of the turbine blades and/or the positions of the louvers 367 can be adjusted to increase the rearward load placed on the transport platform 350.

In general, the foregoing form of aerodynamic braking is most effective at higher vehicle speeds. Accordingly, such embodiments of the energy extraction system 360 used for aerodynamic braking can be supplemented with the (mechanical) regenerative braking system 369 and/or conventional friction brakes. The regenerative brakes 369 can convert rotational energy of the wheels to electrical energy (e.g., via a generator) and/or can capture heat produced during braking. Either form of energy can be directed to the energy storage unit 361 (as shown in FIG. 3) or directly to the reactor 300 and/or other vehicle systems.

In particular embodiments, aerodynamic braking can be used to slow the transport platform as it travels downhill, thus recapturing kinetic energy from the adjacent airstream and at least a portion of the potential energy resulting from the vehicle's previous position at a higher elevation. Conversely, if the vehicle is traveling uphill with energy available in the energy storage unit 361, the controller 362 can direct energy from the energy storage unit 361, and/or from the reactor 300 and/or an electrolysis unit (not shown in FIG. 3), either of which can provide energy to power the locomotion of the vehicle. In other embodiments, the power can be used for lighting, air conditioning, cargo refrigeration, or other purposes. In any of these embodiments, the controller 362 can adaptively harvest and store energy and then direct the energy to one or more applications in an efficient manner.

Figures 4A, 4B:
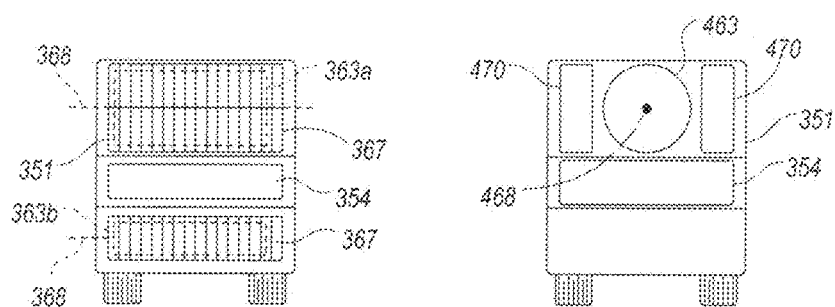
FIG. 4A is a schematic front view of a tractor having multiple wind-driven turbines with transverse rotation axes in accordance with an embodiment of the present disclosure.
FIG. 4B is a schematic front view of a tractor having a wind-driven turbine with a longitudinally-aligned rotation axis in accordance with an embodiment of the present disclosure.

FIG. 4A is a schematic front view of the tractor 351, illustrating the turbines 363a, 363b. As discussed above, each of the turbines 363a, 363b can rotate about a rotation axis 368 having a suitable orientation, e.g., generally transverse to the tractor's direction of travel. The louvers 367 can be positioned upstream (e.g. in front) of each of the turbines 363. In particular embodiments, for example, when the tractor 351 is stopped or travels at low speed, the louvers 367 can be closed. When the tractor 351 achieves a sufficient forward speed (e.g., as detected by the sensors 364 described above with reference to FIG. 3) relative to the local airstream, the louvers 367 can be opened to direct the airflow to the turbines 363. As the turbines 363 operate, they transmit shaft power to a generator (not visible in FIG. 4A) to produce electrical power, and/or can be coupled directly to a mechanical system (e.g., a hydraulic system, a turbo-compressor, a super charger for the tractor engine) to provide the shaft power to that system.

FIG. 4B is a schematic front view of the tractor 351, illustrating a turbine 463 having an orientation different than that shown in FIG. 4A. In particular, the turbine 463 can have a rotation axis 468 generally aligned parallel to the direction of travel of the tractor 351. The turbine 463 can be coupled to one or more generators 470 (two are shown in FIG. 4B) and/or other energy conversion and/or receiving devices.

Figure 4C:
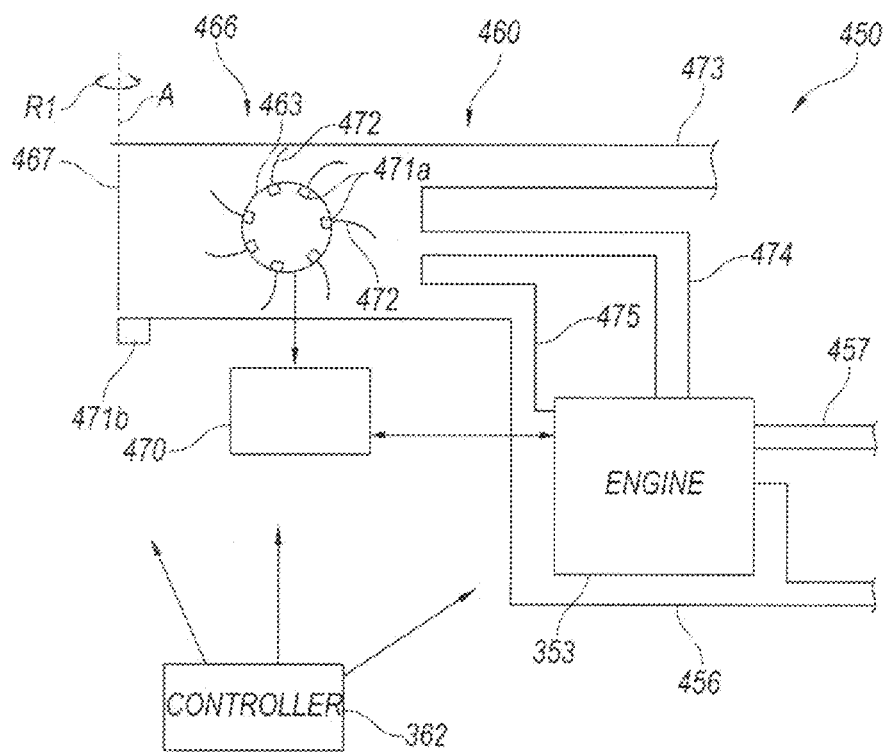
FIG. 4C is a schematic block diagram illustrating actuatable features of an energy extraction system in accordance with embodiments of the present disclosure.

FIG. 4C is a schematic illustration of an embodiment of an energy extraction system 460 that includes one or more actuatable elements 466. The energy extraction system 460 can include a turbine 463 having multiple vanes or blades 472 coupled to corresponding vane or blade actuators 471a. The blade actuators 471a can adjust the pitch angle of the turbine blades 472. This arrangement can accordingly be used to adjust the amount of energy extracted by the turbine 463 from the passing airflow. For example, if in one mode of operation it is preferred not to extract a significant amount of energy using the turbine 463, the turbine blades 472 can be feathered, and/or the turbine 463 can be disconnected from the corresponding generator 470. In another mode, the turbine blades 472 can be pitched to extract power (e.g., a maximum amount of power) and/or to apply a regenerative braking force to the associated transport platform 450, as is described further below.

The energy extraction system 460 can also include multiple louvers 467 (one of which is visible in FIG. 4C) coupled to corresponding louver actuators 471b. The louvers 467 can be rotated about an axis A (as indicated by arrow R1) to adjust the airflow provided to the turbine 463. Accordingly, the louvers 467 and/or the turbine blades 472 can be used alone or in combination to control the amount of air directed to the turbine 463 and the amount of energy extracted by the turbine 463. The actuators 471a, 471b can include air-powered cylinders, hydraulic fluid-powered cylinders, stepper motors, piezoelectric actuators, electromagnetic articulators and/or other suitable devices. Suitable connecting linkages include rack-and-pinion, clevis, cable, and universal joint and rod connections.

In a particular embodiment, the air exiting the turbine 463 can be directed to other portions of the mobile transport platform 450, or can be dumped overboard. In an embodiment shown in FIG. 4C, at least some of the air can be directed through an air cooling duct 475 to a cooling jacket 456 that at least partially surrounds the engine 353. The air can accordingly cool the engine 353 and/or subsystems including the engine exhaust. After performing these functions, the air can be directed to the reactor 300 (FIG. 3) or other vehicle system that utilizes heat. At least some of the air may also be directed through an air intake duct 474 that provides air for combustion to the engine 353. Accordingly, the turbine 463 can, alone or in combination with an additional supercharger, pressurize the combustion intake air provided to the engine 353. The exhaust produced by the engine 353 is carried away by an engine exhaust duct 457. Additional air may be bypassed around the engine 353 via a bypass duct 473 and can be directed overboard the transport platform 450, and/or used for other purposes. Such purposes can include vehicle heating and/or cooling, among others.

The manners by which air is directed among the various systems, subsystems and/or components, and the operation of the turbine 363 and associated actuatable elements 466 can be controlled by the controller 362. As discussed above, the controller 362 can receive relevant inputs from one or more sensors (not shown in FIG. 4C) and base the control signals delivered to the actuatable elements 466 (and/or other system components) on the inputs. The inputs can include, in addition to information received automatically from sensors, instructions from an operator.

Figure 5:
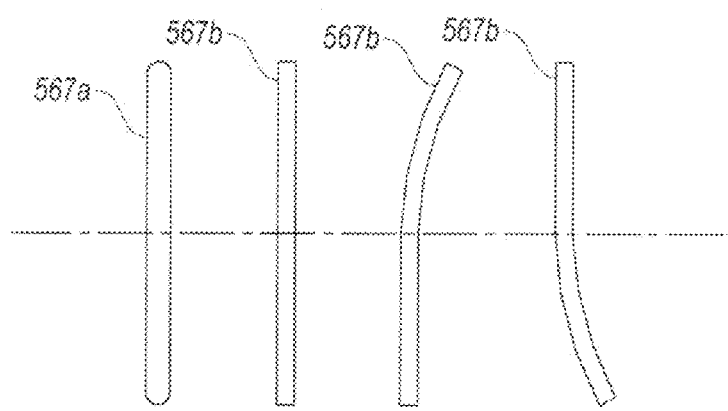
FIG. 5 is a partially schematic illustration of louvers configured and actuated in accordance with embodiments of the present disclosure.

FIG. 5 is a partially schematic illustration of a representative first louver 567a. The first louver 567a can be generally rigid, and can be actuated (e.g., bodily rotated and/or translated) via an actuator, generally as described above with reference to FIG. 4C. FIG. 5 also illustrates a second louver 567b that can have a flexible composition (e.g., can be formed from a composite or other flexible material). In a particular embodiment, the second louver 567b and/or the first louver 567a can be formed from materials produced by the reactor 300 described above, which can provide weight savings, and/or enhanced fatigue endurance, strength and/or corrosion resistance. As shown in FIG. 5, the shape of the second louver 567b can be adjusted in a manner depending upon the nature of composite or other composition of the second louver 567b to control the flow of air in which it is positioned. The second louver 567b can be elastically tensioned to one or more suitable positions/shapes, e.g., by bending and/or warping the structure with respect to a selected neutral axis. Particular orientations, shapes and placements for the louvers, louvers can be selected by wind tunnel testing and/or dimensional analysis techniques. Accordingly, the louvers 567a, 567b and/or other flow control elements may have regular or irregular shapes and/or orientations. The second louver 567b can be moved bodily (as was discussed with reference to the first louver 567a), in addition to changing shape, depending upon the particular embodiment.

Figure 6A:
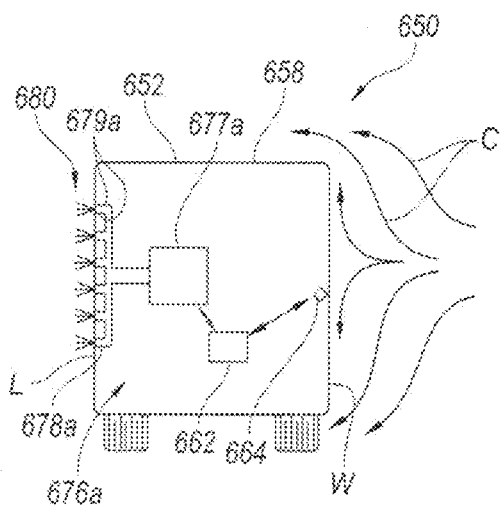
FIGS. 6A-C illustrate cross-wind control systems configured in accordance with embodiments of the present disclosure.
Figure 6B:
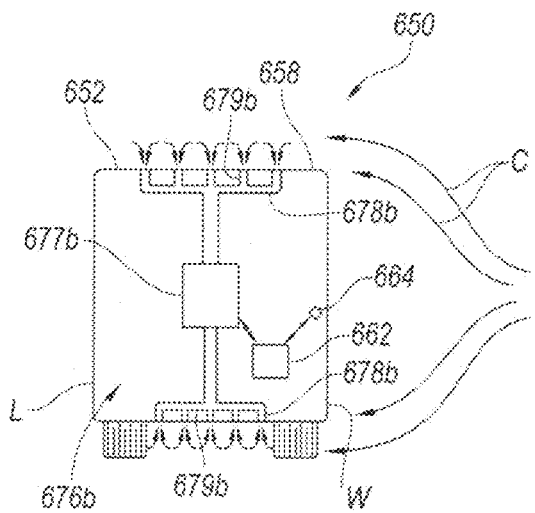
Figure 6C:
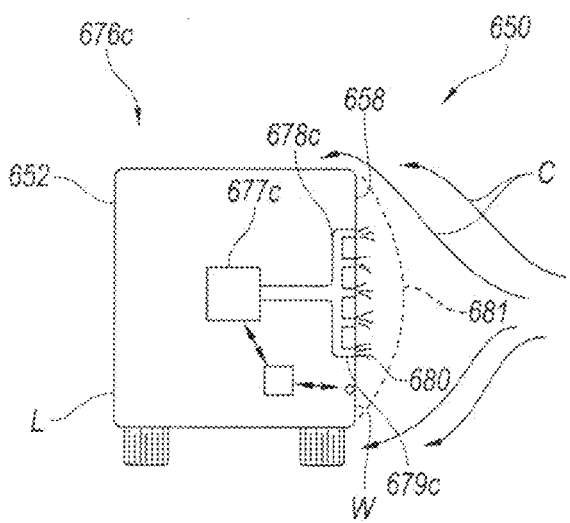

FIGS. 6A-C illustrate a transport platform 650 that includes a cross-wind control system 676a that can be used in addition to or in lieu of the energy extraction systems described above. Referring first to FIG. 6A, the transport platform 650 can include a trailer 652 having an external surface 658. During travel, the external surface 658 is exposed to cross-winds C, indicated schematically by arrows. The cross-winds C impart a greater force on a windward side W of the trailer 652 than on a lee side L of the trailer 652, which can tend to tip the trailer 652. Accordingly, the cross-wind control system 676a counters the load placed on the trailer 652 by the cross-winds C. In a particular embodiment, the cross-wind control system 676a includes a gas flow system 677a that provides a compressed gas (e.g., air) to a manifold 678a. The manifold 678a is coupled to multiple blowing ports 679a. For purposes of illustration, the blowing ports 679a are illustrated only on the lee side L of the trailer 652, opposite from the windward side W. As will be recognized by those of ordinary skill in the relevant art, the transport platform 650 will typically include blowing ports 679a on other surfaces of the vehicle (e.g., the windward side W of the trailer 652 shown in FIG. 6A) to address cross-winds from other directions. The gas flow system 677a is coupled to a controller 662, which is also coupled to one or more sensors 664.

In operation, the sensor(s) 664 detect the cross-wind condition and transmit a corresponding signal to a controller 662. In response, the controller 662 directs the gas flow system 677a to provide a high pressure gas (e.g., air) to the appropriate blowing ports 679a. The blowing ports 679a direct jets 680 that counteract the force of the cross-wind C on the platform 650. Accordingly, the system 676a can reduce or eliminate the tendency for the platform 650 to tip and/or otherwise improve overall vehicle control. It is expected that during normal use, the cross-wind control system 676a will be activated only under cross-wind conditions severe enough to warrant it, so as to avoid unnecessarily energizing the gas flow system 677a. The controller 662 can adaptively vary the response of the system 676a to cross-wind conditions. For example, the controller 662 can direct more air and/or higher pressure air to counteract more severe cross-winds C. The controller 662 can also direct air to only particular blowing ports 679a, depending on the cross-wind conditions.

FIG. 6B schematically illustrates a mobile transport platform 650 having a cross-wind control system 676b configured in accordance with another embodiment of the present technology. In one aspect of this embodiment, the cross-wind control system 676b includes a gas flow system 677b coupled to one or more manifolds 678b to allow or draw air in through corresponding suction ports 679b. Accordingly, the gas flow system 677b can include a vacuum source (e.g., a vent that produces a low-pressure region, or an active vacuum pump) that is selectively activatable to draw air in through the external surfaces 658 of the trailer 652. By drawing air inwardly through the upper and lower surfaces of the trailer 652, the load placed on the windward side W of the trailer 652 can be reduced, e.g., by forcing more air to flow above and/or below the trailer 652. The cross-wind control system 676b can be selectively activated under the direction of the controller 662, which can also operate to direct the air removed through the external surfaces 658 to other systems or subsystems to provide useful functions. For example, the removed air can be used for cooling any of the systems that generate heat, and the removed heat can be directed to the reactor 300 (FIG. 3) and/or other systems that require or benefit from heat. In particular embodiments, the controller 662 can activate the gas flow system 677b to perform other functions, for example, boundary layer control functions. Accordingly, the gas flow system 677b can be activated to provide just enough suction to control the local flow over the surface through which the air is drawn, and/or can be activated to provide blowing air to the surface. The temperature of the air provided to the surface 658 can be temperature controlled to produce additional aerodynamic flow control.

FIG. 6C illustrates a cross-wind control system 676c configured in accordance with still another embodiment of the present technology. In one aspect of this embodiment, the gas control system 677c provides pressurized air (or another gas) to a manifold 678c, which directs jets 680 through corresponding blowing ports 679c located on the windward side W of the transport platform 650. The jets 680 can be selectively controlled and operated to produce an effective aerodynamic shape 681 (indicated in dashed lines) as different than the physical shape of the windward side W. The effective aerodynamic shape 681 can more effectively divert the cross-winds C above and/or below the transport platform 650. As was discussed above with reference to FIG. 6A, a similar arrangement can be installed on the lee side L of the transport platform 650 to counteract cross-winds C from the opposite direction.

In particular embodiments, any of the foregoing systems described individually above with reference to FIGS. 6A-6C may be combined with any other system disclosed in these Figures. In other embodiments, such systems or combinations of systems are combined with any of a variety of systems disclosed herein, e.g., on the same transport platform.

Figure 7:
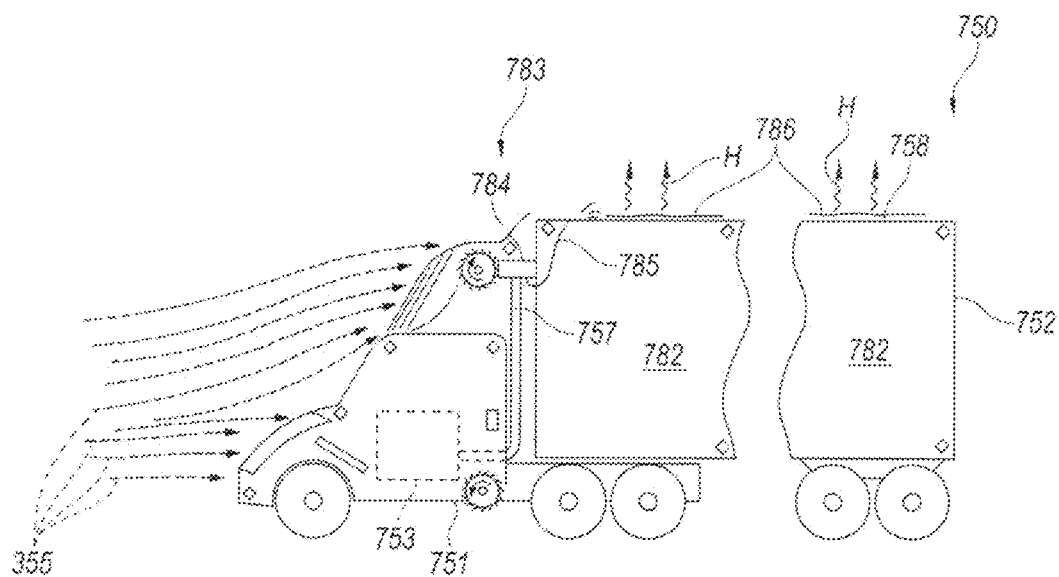
FIG. 7 is a schematic side view of a mobile transport platform having an evaporation-based refrigeration system configured in accordance with an embodiment of the present disclosure.

FIG. 7 is a schematic illustration of a mobile transport 750 having a refrigeration system 783 configured in accordance with an embodiment of the present disclosure. The refrigeration system 783 may be employed in addition to or in lieu of any of the other systems disclosed herein. In a particular embodiment, the mobile transport platform 750 includes a tractor 751 and a trailer 752 having a refrigerated volume 782. The refrigeration system 783 can include features that use compression, expansion and/or evaporation to provide refrigeration. For example, the tractor 751 can include an exhaust duct 757 that directs exhaust products away from the corresponding engine 753. The refrigeration system 783 can include a water trap 784 that collects water from the exhaust flow and directs the water to an external surface 758 of the trailer 752, via a conduit 785. The resulting water film 786 can flow along the external surface 758. As the water film 786 evaporates due to convective and/or conductive interactions with the adjacent airstream, it transfers heat (indicated by arrows H) away from the external surface 758 to cool the refrigerated volume 782 within the trailer 752. This arrangement can increase the overall efficiency of the refrigeration process by making use of energy sources that are typically wasted. Such sources include moisture that can be condensed from the engine exhaust and the convective effect of the airstream adjacent to the mobile platform 750. In at least some embodiments, the transport platform 750 can include a conventional electrically or gas-powered refrigerator in addition to the system 783, e.g. to provide refrigeration when the transport platform 750 is stopped and/or at other times when cooling in addition to evaporative cooling is requested.

Figure 8:
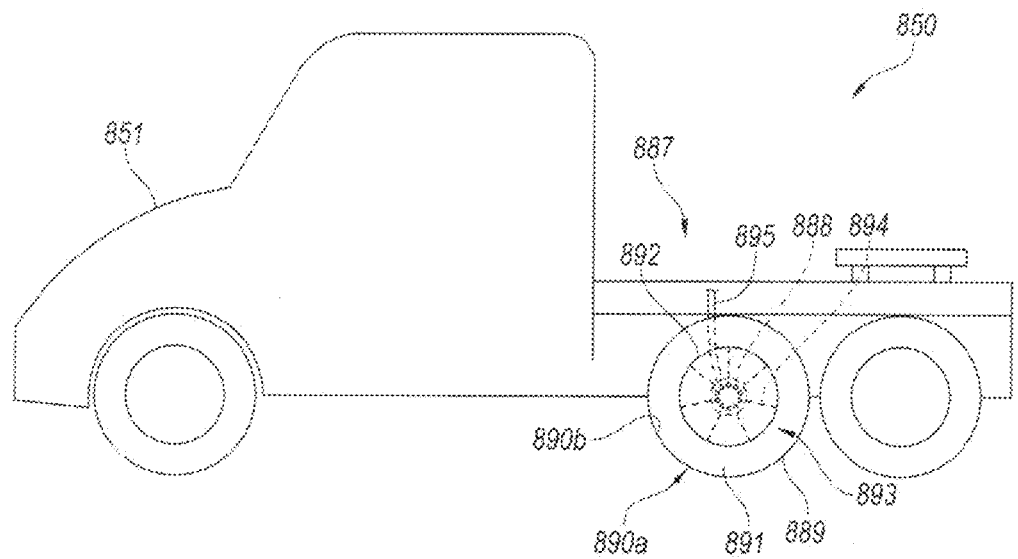
FIG. 8 is a schematic illustration of a mobile transport platform having a tire system with heat transfer features in accordance with an embodiment of the present disclosure.

FIG. 8 is a schematic illustration of a mobile transport platform 850 that includes a tractor 851 having a tire system 887 configured in accordance with still another embodiment of the present disclosure. The tire system 887 can be used in addition to or in lieu of any of the other systems described herein. In a particular embodiment, the tire system 887 includes a wheel 888 that carries a tire 889 mounted on a rim 892. The tire 889 is formed from a solid, elastomeric tire material, e.g., a rubber compound with suitable reinforcement. The tire 889 has an outer surface 890a that contacts the road (or other surface over which the tractor 851 travels), and an inner surface 890b. The inner surface 890b can define a sealed internal volume 891 of the tire 889.

In a conventional tire, the internal volume 891 is filled with air or nitrogen. By contrast, in an embodiment of the present technology, the internal volume 891 is filled or at least partially filled with a non-air, non-nitrogen heat transfer fluid 893. The heat transfer fluid 893 can include helium, hydrogen or another suitable gas having a relatively high thermal conductivity, and/or a liquid, also having a relatively high thermal conductivity. Representative liquids include glycol and glycerin. In any of these embodiments, the fluid 893 receives heat from the inner surface 890b of the tire 889 generated by motion, including internal frictional forces and external frictional forces between the outer surface 890a and the road surface. The fluid 893 conveys the heat to one or more thermal conduction paths 894 (e.g., elements of the rim 892) and from the rim 892 to the wheel 888. The heat conveyed to the wheel 888 can then be rejected or captured and used onboard the transport platform 850, or the heat can be directed into the stream of air flowing past the transport platform 850. In a particular embodiment, the heat generated by the tires 889 can supplement heat generated by the regenerative braking system 393 (shown in FIG. 3) e.g., to provide sufficient heat for other vehicle systems (e.g., the thermochemical reactor 300 described above with reference to FIG. 3). The reactor 300 can generate hydrogen and/or another suitable heat transfer fluid to replenish the fluid 893 in the tire 889, and/or control the pressure of the fluid in the tire 889, via a replenishment line 895. In other embodiments, the transport platform 850 can include a regenerative braking system 393 that directs braking energy to an electrical generator or directly back to the engine.

FIG. 9 illustrates a block diagram of a mobile transport platform 950 having multiple systems configured in accordance with embodiments of the present disclosure. The transport platform 950 can include an energy extraction system 960 (e.g., an arrangement of turbines as described above with reference to FIG. 3) and can further include an energy storage unit 961. As discussed above, the energy storage unit 961 can include a battery, charged capacitor, flywheel, pressure vessel, or other arrangement for storing energy.

The mobile transport platform 950 can also include multiple sensors 964 and one or more controllers 962. The sensors 964 can measure air pressure, humidity, velocity, temperature and/or other values, and can also detect vehicle parameters, including the vehicle velocity, engine status, fuel consumption rate, steering function, and/or braking function, among others. The controller 962 is operably coupled to the sensors 964 to receive information from the sensors 964 and direct the operation of the energy storage unit 961 and one or more systems 996 also carried by the mobile transport platform 950. Individual features of the systems 996 are described in further detail below.

The vehicle systems 996 can include a thermochemical reactor 900 that can receive reactants and produce products in the manner described above with reference to the reactor 300 shown in FIG. 2. The reactor 900 can receive energy from the energy extraction system 960. In another embodiment, the mobile transport platform 950 can include an electrolysis or hydrolysis unit 996a that carries out a hydrolysis reaction (e.g., on condensed water extracted from the exhaust system) to produce hydrogen for fuel and/or other purposes including for use in a tire system 987. The tire system 987 can be generally similar to the tire system 887 described above with reference to FIG. 8. Other systems include the engine intake 996b (e.g. fuel and/or air), the vehicle's HVAC system 996c, a gas flow system 977 (e.g., similar to the systems described above with reference to FIGS. 4A-4C) and/or other auxiliary vehicle systems 996d including a refrigeration system (e.g., similar to the refrigeration system 783 described above with reference to FIG. 7). Other systems can also include electrical systems (e.g., lights, electronics, communication systems), steering systems, additional braking systems, among others. By providing energy to the foregoing subsystems from the energy extraction system 960 rather than from the propulsion engine driving the transport platform 950, more energy from the propulsion engine is available to provide motive power, which is typically its primary function.

Figure 9A:
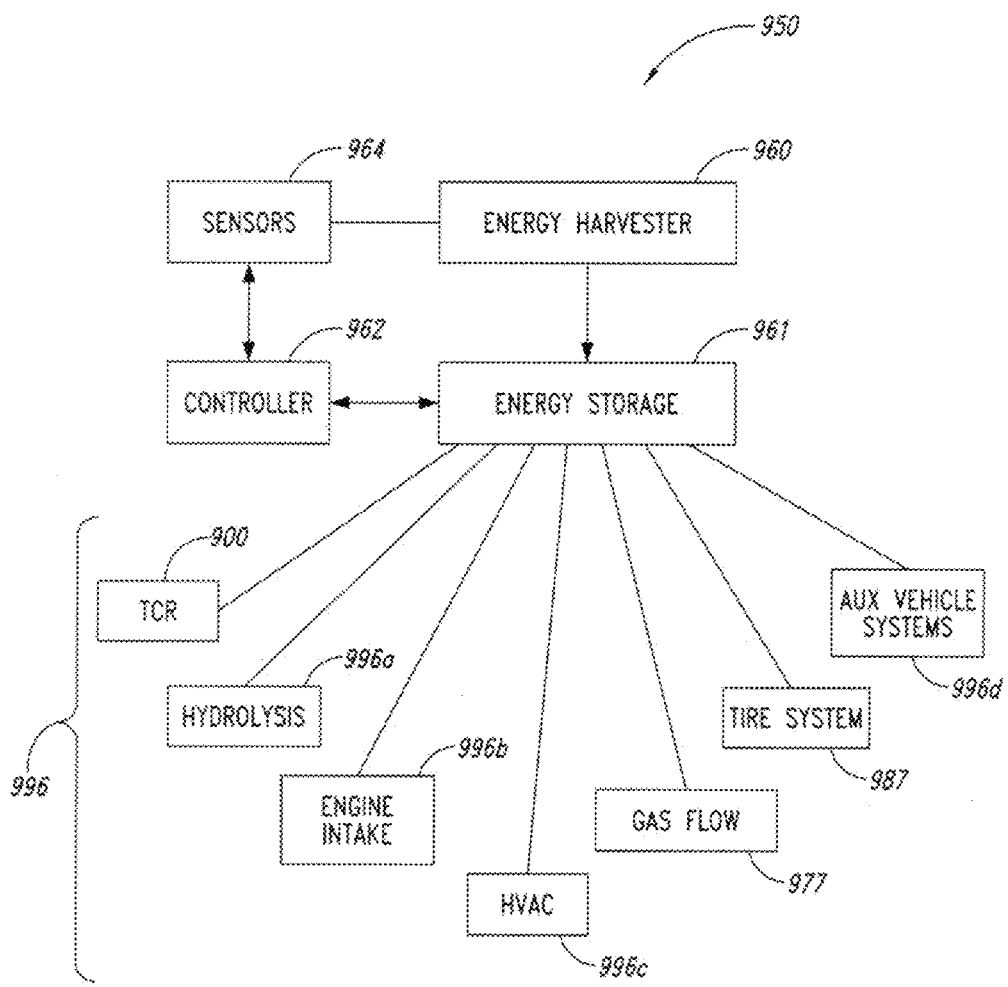
FIG. 9A is a block diagram schematically illustrating interconnections between an energy extraction system and other mobile transport platform subsystems in accordance with embodiments of the present disclosure.
Figure 9B:
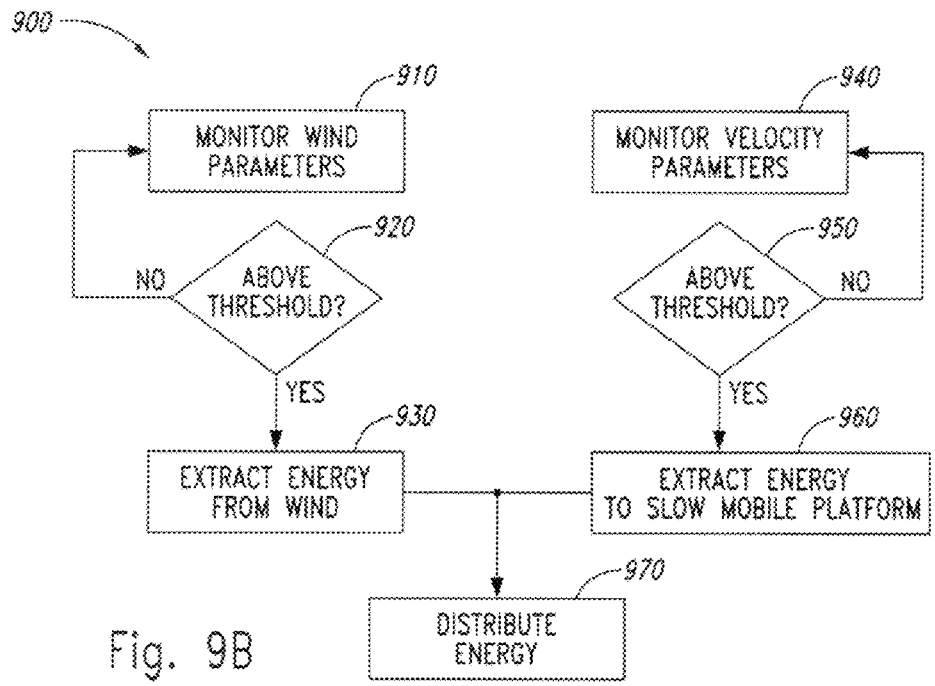
FIGS. 9B and 9C illustrate flow diagrams of processes in accordance with embodiments of the present disclosure.

FIG. 9B illustrates a process 900 for operating a mobile transport platform in accordance with a particular embodiment of the present technology. The process 900 can include monitoring wind parameters (process portion 910) and determining whether the wind parameters are above a threshold value (process portion 920). Suitable target parameters can be based on a combination of measured wind parameters e.g., velocity and humidity. For example, wind with higher humidity has less mass and therefore less momentum than dry air at the same velocity, which can affect the manner in which the system extracts energy. Other combinations of wind parameters can be used in other embodiments. If the wind parameters exceed the threshold value (e.g., if the wind velocity exceeds a predetermined value), then the process includes extracting energy from the wind (process portion 930) in any of the manners described above. If not, the process returns to monitoring the wind parameters.

The process 900 can also include monitoring the velocity and/or other parameters of the mobile transport platform (process portion 940). If the target parameter(s) are above a threshold value (as determined in process portion 950) and the system receives an input requesting braking, then the process further includes extracting energy in a manner that slows the mobile transport platform (process portion 960). For example, process portion 960 can include opening louvers and/or changing turbine pitch angles and/or activating a regenerative brake, all of which extract energy and slow the mobile transport platform at the same time. In process portion 970, the energy received by the energy extraction techniques, whether or not used to slow the mobile platform down, are distributed to corresponding systems, as discussed above with reference to FIG. 9A.

Figure 9C:
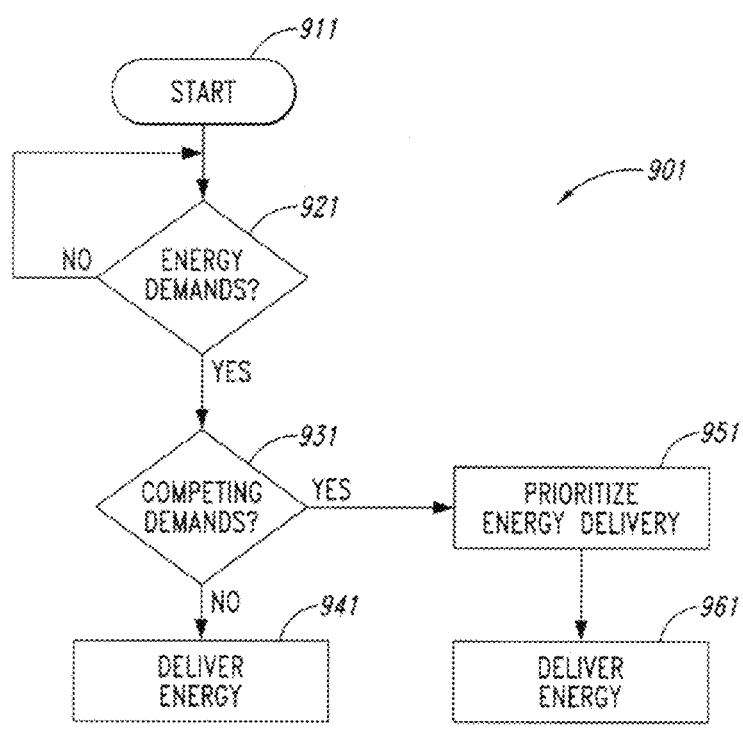

FIG. 9C illustrates another process 901 for operating the mobile transport platform. After initiating the process (process portion 911), the process includes determining whether one or more energy demands exists (process portion 921). The demands can come from several vehicle systems, including the main engine of the vehicle. At times, the main engine requires all of the available power to climb a hill or accelerate. At other times, such as when coasting downhill, the main engine may not have such high energy demands. If such demands exist, the process 901 includes determining whether multiple demands are competing (process portion 931). If not, energy is delivered in response to the demand (process portion 941) and if so, process portion 951 includes prioritizing the energy delivery. In process portion 961, the energy is the delivered in accordance with the prioritization established in process portion 951.

Figure 10A:
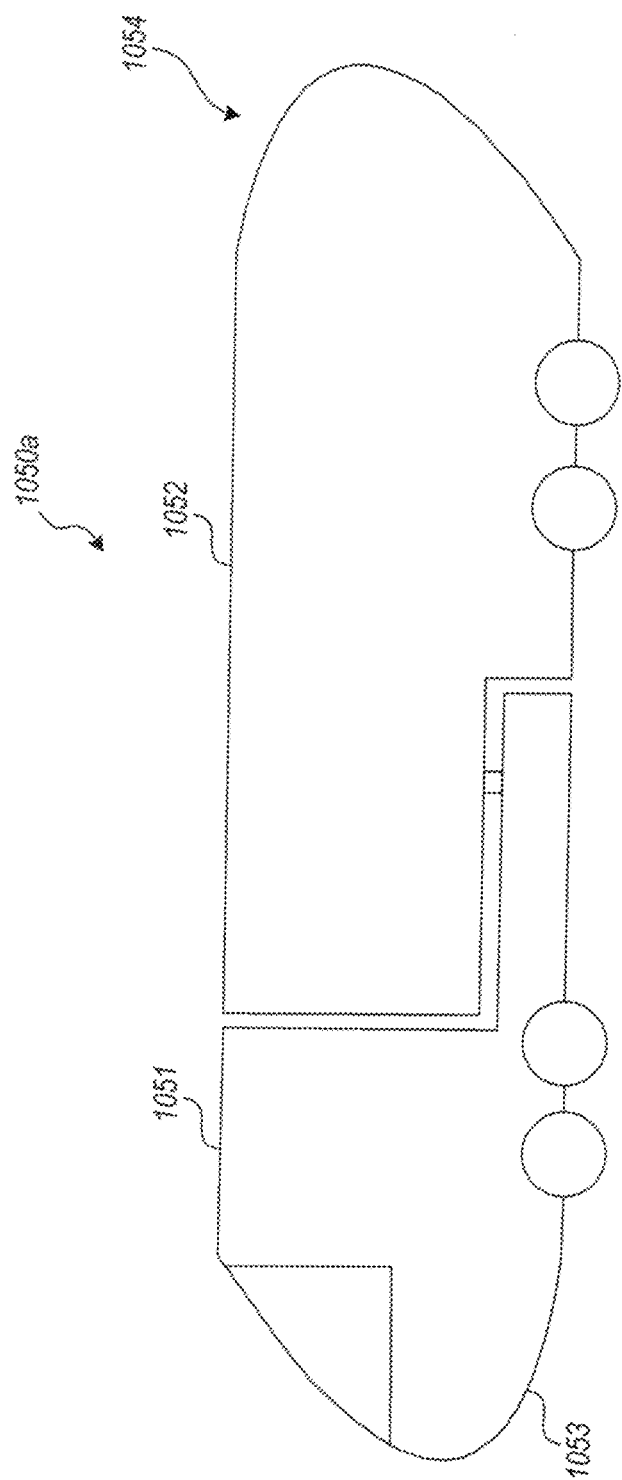

Several embodiments of the systems and methods described above were described in the context of mobile transport platforms that include a tractor-trailer combination. In other embodiments, the tractor-trailer combination can include features in addition to or in lieu of those described above. For example, FIG. 10A illustrates a mobile transport platform 1050a that includes a tractor 1051 having a nose 1053 that includes significantly more aerodynamic shaping than a conventional tractor. In addition to, or in lieu of, the foregoing feature, the trailer 1052 can include a tail 1054 that is also aerodynamically tailored to reduce base drag. These features can be included in the mobile transport platform 1050a, for example, when the overall economic and/or environmental benefits obtained by these features outweigh the potential loss in cargo space resulting from these features.

Figure 10B:
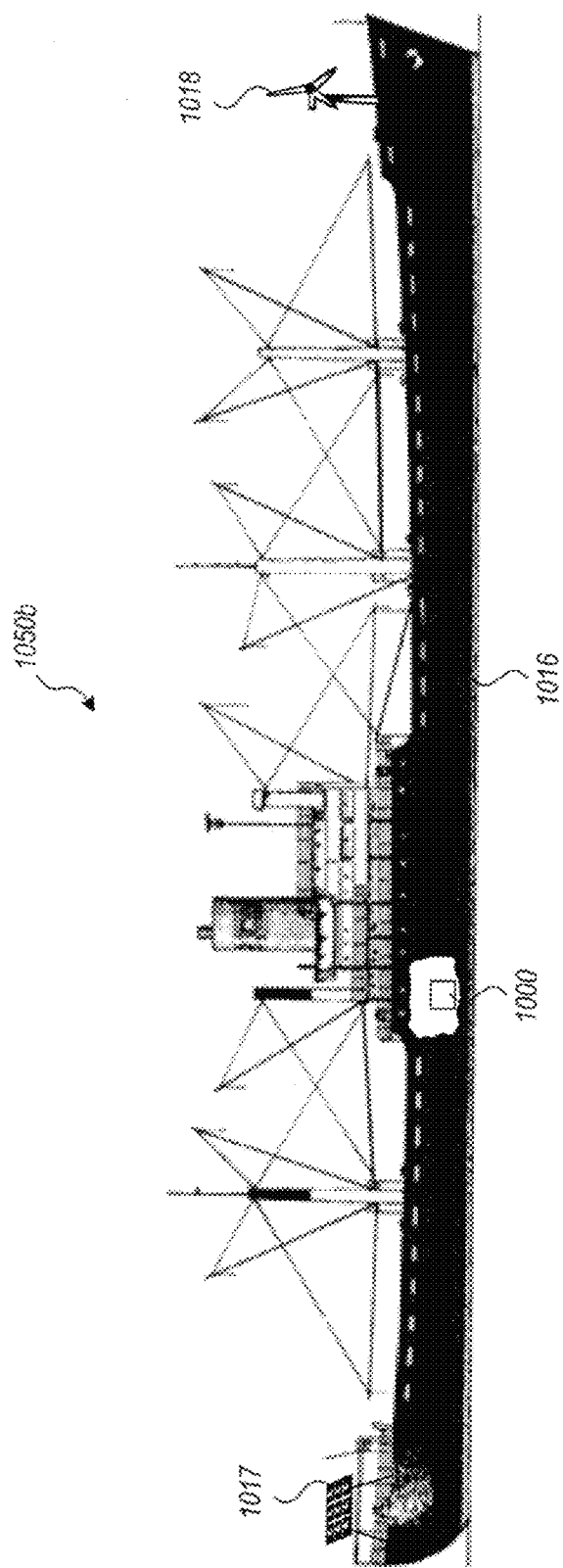

In other embodiments, any of the forgoing systems may be applied to vehicles other than a tractor-trailer combination. For example, the systems may be applied to a single-unit truck, or to other over-the-road vehicles. In still further embodiments, the systems may be applied to marine vessels. For example, FIG. 10B illustrates a mobile transport platform 1050b that includes a ship 1016 carrying a reactor 1000. The reactor 1000 can be powered by energy extracted from the ship's engine, by a solar collector 1017, and/or by a wind turbine 1018. The wind turbine 1018 can have a configuration more akin to a conventional wind turbine than those specifically adapted for implementation on a truck in the manners described above. Regardless of the configuration of the wind turbine 1018, the operation of the ship 1016 and in particular embodiments, the operation of the reactor 1000, can benefit from the energy extracted by the wind turbine 1018.

In another embodiment shown in FIG. 10C, the ship 1016 can include one or more wave energy capture devices 1019 that extract energy from the relative motion of the ship 1016 and the water in which it travels. For example, the wave energy capture devices 1019 can respond to relative motion created by the ship's rolling action and/or pitching action, or simply the motion of waves through which the ship 1016 passes. The wave energy capture devices 1019 can accordingly provide energy in addition to or in lieu of the energy described above with reference to FIG. 10B.

FIG. 10D illustrates a mobile transport platform 1050d that includes a tug 1023 that provides motive power for a barge 1021. The barge 1021 can include a thermochemical reactor 1000, and/or such a reactor 1000 can be carried by the tug 1023. In either embodiment, the tug 1023 and/or the barge 1021 can include energy extraction features generally similar to those described above.

Figure 10E:
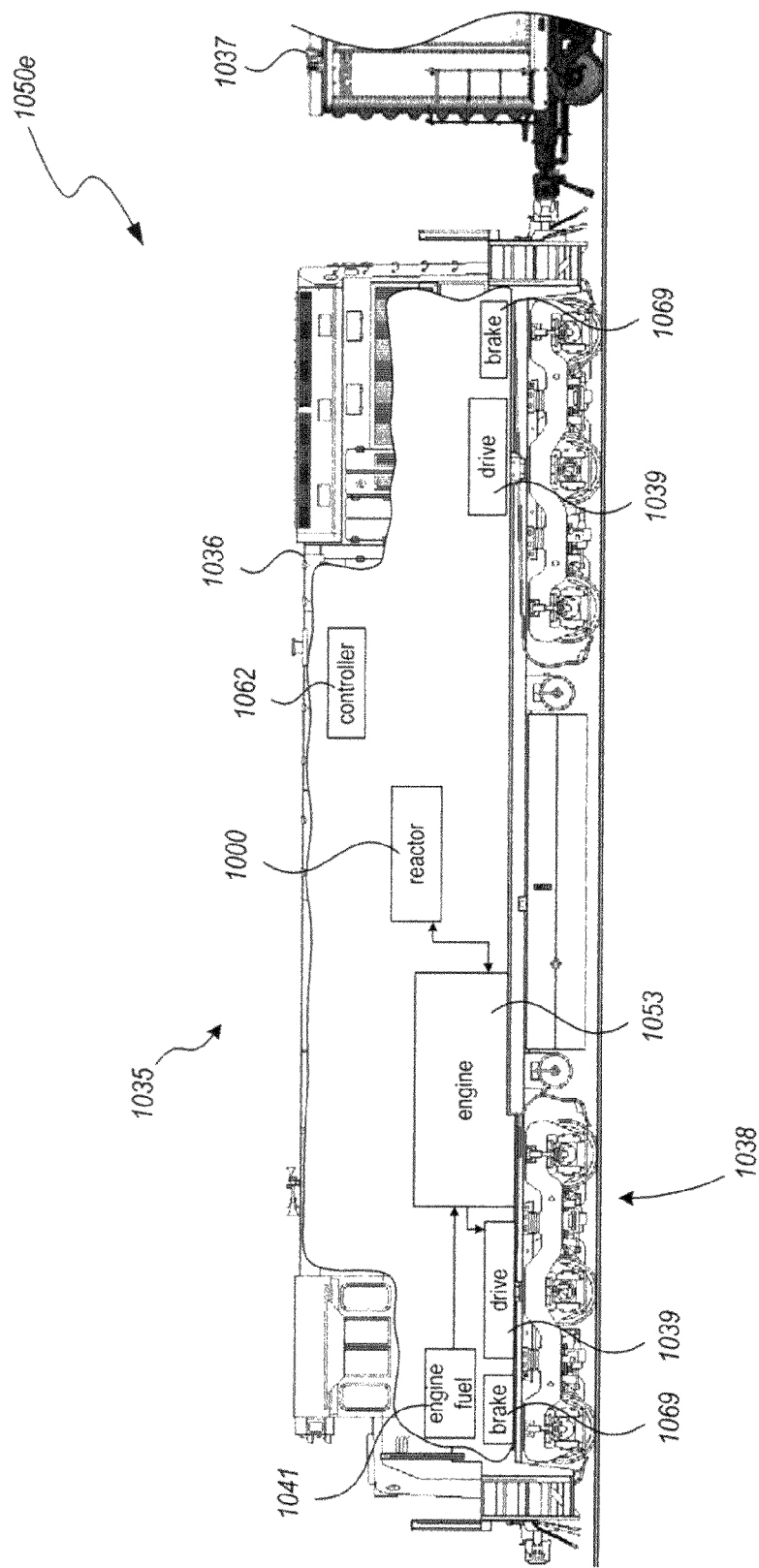

FIG. 10E illustrates yet another mobile transport platform 1050e that includes a train 1035. The train 1035 can include a locomotive 1036 and, optionally, one or more pieces of rolling stock 1037. The locomotive 1036 can include an engine 1053 that receives fuel from a fuel tank 1041 and provides motive power to a propulsion device 1038. In particular embodiments, the propulsion device 1038 includes one or more drive mechanisms 1039 that drive the locomotive wheels. The wheels can be braked with a regenerative braking system 1069. Power from the engine 1053 and/or the regenerative brakes 1069 can be provided to a reactor 1000 to facilitate a thermochemical dissociation process, as was described above with reference to FIG. 2. The operation of the systems carried by the locomotive 1036 and/or the rolling stock 1037 can be controlled by a suitable controller 1062.

FIG. 11 illustrates an embodiment of the present technology in which the products from a thermochemical reactor 1000 are used to refrigerate, preserve, and/or discourage destruction of a cargo 1081. In particular embodiments, the cargo 1081 includes food or other perishables, and in other embodiments, the cargo 1081 can include other materials. The cargo 1081 can be carried in a container 1080, for example, a multi-modal container, or it can be carried in a trailer or other suitable device. In any of these embodiments, the container 1080 can enclose or partially enclose an internal volume 1082 (e.g., a payload volume). A refrigerator 1083 is located within or outside the internal volume 1082 and is coupled in thermal communication with the internal volume 1082 to cool the internal volume 1082 and the cargo 1081.

The reactor 1000 can receive reactants 1002 and direct the products of the reaction performed at the reactor 1000 in one or more storage vessels 1001, three of which are illustrated in FIG. 11 as vessels 1001a, 1001b, and 1001c. Depending upon the nature of the reactants 1002 and the process conducted in the reactor 1000, the products can include carbon monoxide, carbon dioxide, nitrogen, and/or other elements or compounds that have been dissociated from the reactants 1002. As these constituents may be used in any of a number of manners to facilitate handling the cargo 1081, in a particular embodiment, the system includes a manifold 1085 that can direct products from any of the storage vessels to perform any of a number of functions. For example, the refrigerator 1083 can include a refrigerant that may become depleted over the course of time. The refrigerant may include carbon dioxide, nitrogen, or another constituent that is produced as a product by the reactor 1000. Accordingly, the manifold 1085 can direct one or more suitable products from any of the storage vessels 1001 to the refrigerator 1083 to recharge the working fluid at the refrigerator 1083.

In another embodiment, the products produced by the reactor 1000 can be used to discourage pests from entering or remaining in the container 1080. For example, the manifold 1085 can direct carbon dioxide, carbon monoxide, or nitrogen into the internal volume 1082 of the container 1080 to discourage and/or kill such pests. In still further embodiments, the products from the reactor 1000 can be supplied directly to the cargo 1081. For example, carbon monoxide is frequently used to preserve the color and/or freshness of meat, fish, and/or other perishables. In at least some cases, the carbon monoxide used to perform this function can be replenished en route by directing carbon monoxide produced by the reactor 1000 to the cargo 1081 via the manifold 1085, as indicated by arrow C. For example, if the cargo 1081 includes boxed products, the manifold 1085 can direct the gas into the box. If the cargo 1081 includes unboxed or otherwise unpackaged products (e.g., hanger meat), the gas directed into the internal volume 1082 can perform the foregoing functions.

In yet further embodiments, the manifold 1085 can direct the constituent directly to the internal volume 1082 to cool the internal volume, in addition to or in lieu of cooling provided by the refrigerator 1083. For example, the constituent can be cooled to a liquid or solid form (e.g, to cryogenic temperatures), and can then be directed into the internal volume 1082. As the liquid or solid transitions back to a gas, it absorbs heat from the internal volume 1082 and is then vented.

In particular embodiments, any of the foregoing functions provided by the products produced by the reactor 1000 can be used in any of a variety of suitable combinations. In further embodiments, reaction products other than those specifically described above can be used to perform the same or similar functions. Carbon-based products (e.g., carbon monoxide and carbon dioxide) can be produced from hydrocarbons or other carbon-bearing reactants, and nitrogen products (e.g., $N_2$) can be produced from ammonia, urea, and/or other nitrogen-bearing reactants.

Transportation systems including trains, trucks and cars dissipate enormous amounts of energy during deceleration and braking operations in which friction brakes are applied to convert the vehicle's kinetic energy into heat. Jake brakes are also utilized with heat engines such as diesel engines to convert the vehicle's kinetic energy into work against the atmosphere and heat. In particular embodiments of the present technology, slowing or braking is performed using any one or combination of the following techniques:

(1) adaptively provide fuel-injection and ignition at one or more times during the compression stroke of one or more combustion chambers to produce sufficient back work to cause substantial deceleration, and/or (2) supply increased flow of air into the combustion chambers of the drive engine, and/or (3) cut off the direct injection of fuel to each combustion chamber, and/or (4) harvest energy from engine- and/or vehicle-driven electricity generators such as reversible motor-generators and alternators, and/or (5) apply or direct exhaust gases to a variable torque turbo-generator that is operated to overcome drawbacks of Jake brakes, and/or (6) utilize the engine as a compressor to supply compressed gases to drive work production by various sub-systems and/or to pressurize a suitable storage container with compressed air.

Any one or combination of the foregoing embodiments can provide enormous stopping power and drive subsystems that greatly improve overall fuel economy, performance, and operational safety. Safety improvements can include:

(a) reduction or elimination of overheated and/or failed friction brakes, and/or (b) reduction or elimination of skidding and braking or acceleration because of traction loss due to snow impedance, water film and snow-ice produced by tire compression and compaction, and/or (c) reduction or elimination of snow, ice, and/or mud accumulations on the surfaces of vehicles Air that is compressed and/or stored as a result of such regenerative braking operations may be utilized in applications that include increasing the air flow to an engine at times that improved torque and/or power is demanded, to assist in the operation of mechanical or hydraulic brakes, and/or to operate power assisted pneumatic devices that are deployed or otherwise operated to adaptively reduce vehicle drag, and/or to blow snow away from roadway areas in front of rotating tires to prevent compaction and/or ice formation or in other ways improve traction for propulsion, steering, or stopping along with reduced rolling resistance between deceleration events, and/or to inflate tires and/or actuate jacks to lift a vehicle on occasions that tires are to be fitted with traction devices such as snow chains or to remove and replace worn or punctured tires.

FIGS. 12A-14B illustrate embodiments of transportation systems that use compressed air and/or other gases to carry out vehicle functions. As discussed above, compressed air provided to a vehicle can be used for a number of purposes to improve the energy efficiency of the vehicle. The compressed air can be generated by any of a variety of suitable methods, including by harvesting energy from the adjacent flow stream, as described above. Several representative embodiments of mechanisms that may be actuated with compressed air are described below in the context of tractor-trailer combinations. In other embodiments, similar methodologies may be applied to other vehicles.

Figure 12A:
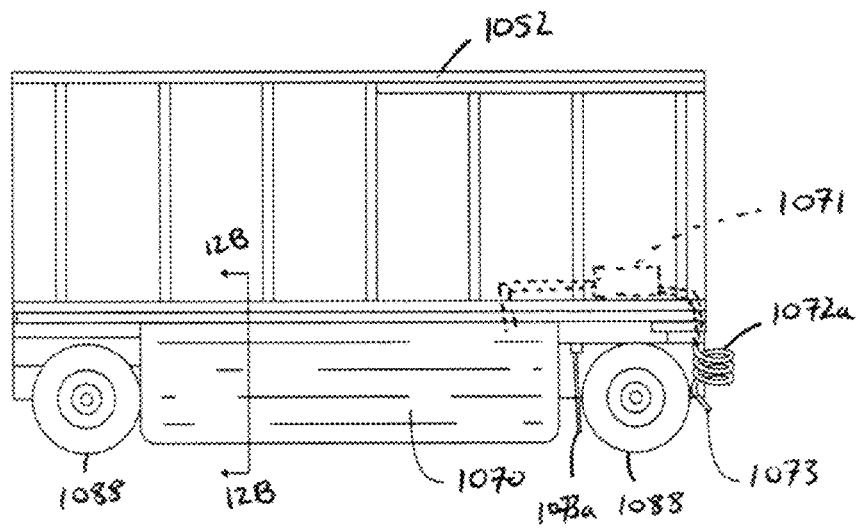
FIGS. 12A-12M illustrate streamlining fairings and associated methods for deploying and stowing fairings, in accordance with embodiments of the present technology.

FIG. 12A illustrates a trailer 1052 that is operatively coupled to a compressed air storage tank 1071 in accordance with an embodiment of the present technology. In a particular embodiment, the compressed air storage tank 1071 is carried by the trailer 1052 itself, and in other embodiments, the compressed air storage tank 1071 may be carried by a tractor or other component of an overall transport system. In any of these embodiments, the compressed air storage tank 1071 can supply air to a first compressed air conduit 1072a that is in turn coupled to a nozzle 1073. The nozzle 1073 can be positioned proximate to one or more of the wheels 1088 of the trailer 1052 and can be activated to blow or otherwise remove obstructions from the region around the wheel 1088. For example, during snowy conditions, the nozzle 1073 can be used to blow snow away from the region in front of the wheel 1088. In an icy environment, the nozzle 1073 can blow heated air ahead of the wheel 1088 to melt the ice. In rainy conditions, the nozzle 1073 can blow compressed air ahead of the wheel 1088 to reduce or eliminate the likelihood for hydroplaning. Accordingly, the foregoing measures can improve overall vehicle efficiency and/or vehicle safety. As shown in FIG. 12A, one or more additional nozzles 1073a can be positioned behind the wheel 1088, and/or at other locations relative to the wheel 1088.

The compressed air storage tank 1071 can also provide air to deploy components or activate components that improve the aerodynamic efficiency of the trailer 1052. For example, the compressed air storage tank 1071 can be coupled to a second compressed air conduit 1072b that is in turn coupled to a deflector or fairing 1070. The fairing 1070 can be operated to move between a deployed position (shown in FIG. 12A) and a stowed position (described further below with reference to FIGS. 12C and 12D). In the deployed position, the fairing 1070 reduces turbulence caused by airflow beneath the trailer 1052 by deflecting air around the undercarriage of the vehicle, which typically includes tanks, struts, stands, and other equipment that forms drag-producing flow obstructions.

Figure 12B:
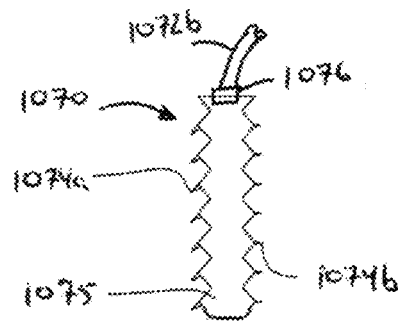
Figure 12C:
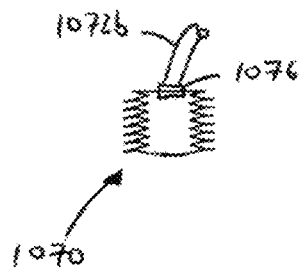

FIG. 12B is a cross-sectional illustration of the fairing 1070, taken substantially along line 12B-12B of FIG. 12A. As shown in FIG. 12B, the fairing 1070 can have an accordion-type arrangement, with an internal volume 1075 in fluid communication with the second compressed air conduit 1072b via a compressed air fitting 1076. When compressed air is provided to the internal volume 1075 via the compressed air fitting 1076, the fairing 1070 expands as shown in FIG. 12B, and when the air pressure is released, and/or when a vacuum or other restoring force (e.g., a spring) is applied to the fairing 1070, the fairing 1070 can collapse, as shown in FIG. 12C. In particular embodiments, the fairing 1070 can include outwardly extending ribs 1074 (shown as first ribs 1074a and second ribs 1074b) that can further enhance the aerodynamic efficiency of the trailer 1052 or other vehicle on which the fairing 1070 is installed. In particular, the ribs 1074 can be oriented (e.g., upwards, downwards, or horizontally) to control the flow passing by the fairing 1070 and reduce or eliminate the amount of turbulent flow along the fairing 1070. In particular, the ribs can delay the transition of the adjacent air flow from laminar to turbulent flow and therefore reduce frictional forces on the fairing 1070.

Figure 12D:
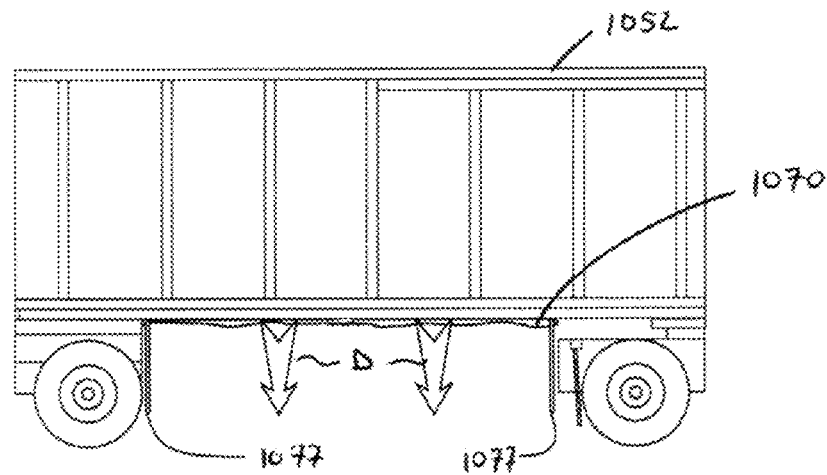

FIG. 12D illustrates the trailer 1052 with the fairing 1070 in the stowed position. The fairing 1070 can be deployed as indicated by arrows D by filling the internal volume 1075 with compressed air, as described above with reference to FIG. 12B. In a particular aspect of the embodiment shown in FIG. 12D, the trailer 1052 can include guide rails 1077 that guide the fairing 1070 as it deploys. The guide rails 1077 can be fixed in some embodiments, and can be deployable (e.g., via a telescoping arrangement) in other embodiments. In still further embodiments, the guide rails can include rods, struts, or other elements that provide a guiding function. In any of these embodiments, the fairings can be deployed and retracted quickly so as to respond to changes in road conditions and/or wind conditions in real time or near real time.

Figure 12E:
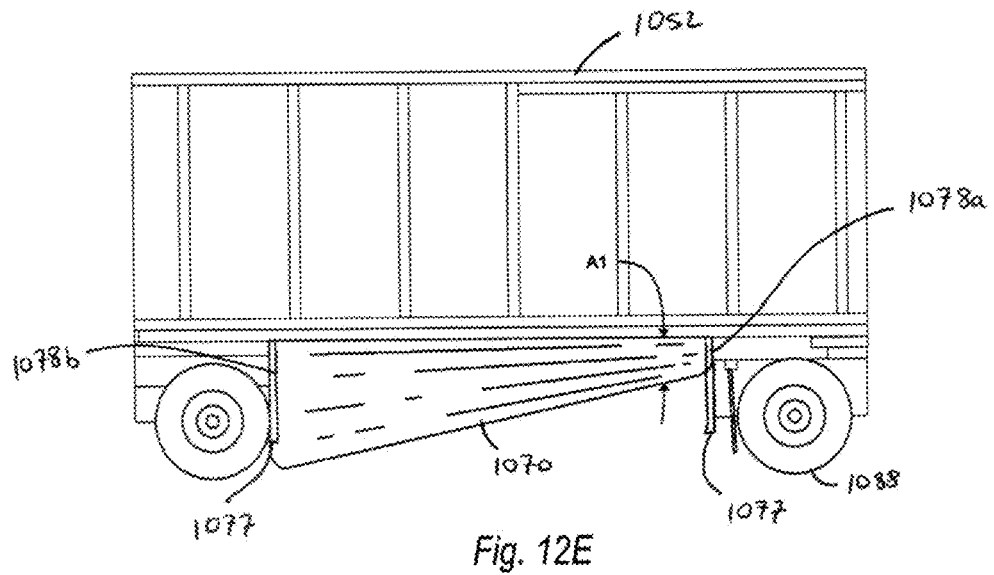
Figure 12F:
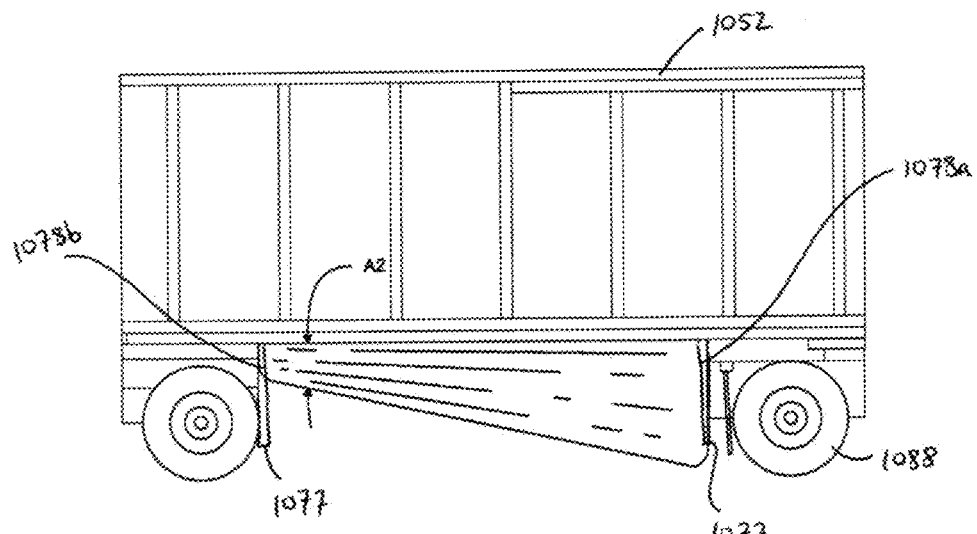

FIGS. 12E and 12F illustrate the fairing 1070 deployed in differential manners in accordance with further embodiments of the present technology. For example, FIG. 12E illustrates the fairing 1070 having a leading edge 1078a that is undeployed or partially deployed, and a trailing edge 1078b that is fully deployed, so that a lower edge of the deflector 1070 forms an acute angle A1 with the longitudinal axis of the trailer 1052. In FIG. 12F, the relative deployments of the leading edge 1078a and the trailing edge 1078b are reversed, forming an oppositely-facing acute angle A2 between the lower edge of the deflector and the longitudinal axis of the trailer 1052. In other embodiments, the fairing 1070 can be deployed differentially in other manners, depending generally upon the local conditions, so as to improve the aerodynamic efficiency of the trailer 1052. For example, the fairings may be differentially deployed based on cross-winds, partial cross-winds, headwinds, tailwinds and/or other conditions.

Figure 12G:
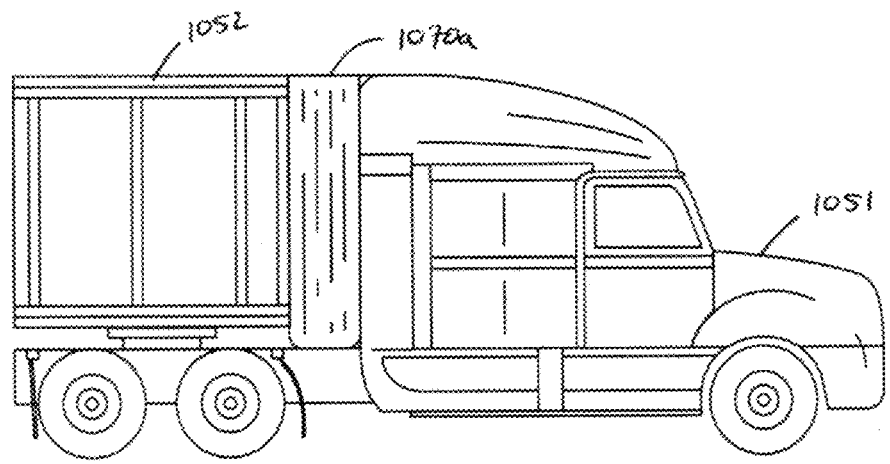
Figure 12H:
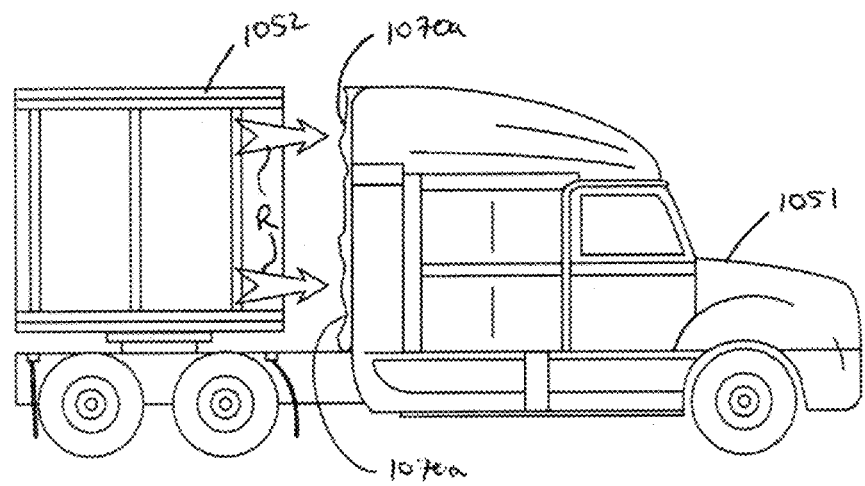

Techniques similar to those described above with reference to FIGS. 12A-12F can be employed on other portions of the trailer 1052 and/or the tractor to which the trailer is attached. For example, as shown in FIG. 12G, a first fairing 1070a is positioned between the trailer 1052 and a tractor 1051 that propels the trailer 1052. The first fairing 1070a is shown in its deployed position in FIG. 12G, and is shown retracted, as indicated by arrows R, in FIG. 12H. The first fairing 1070a can be activated using compressed air, in a manner generally similar to that described above.

Figure 12I:
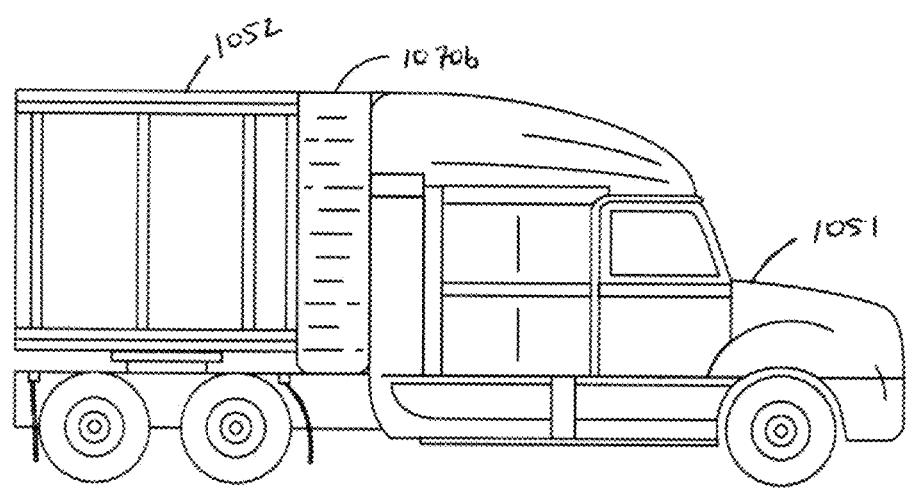
Figure 12J:
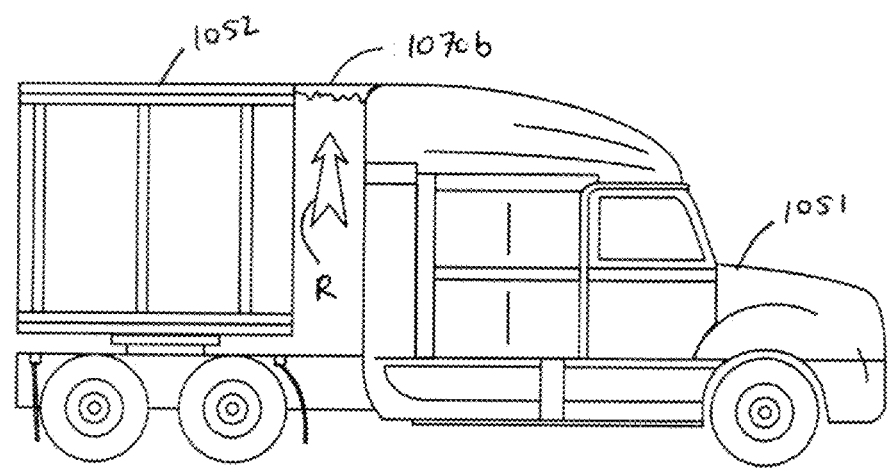

FIGS. 12I and 12J illustrate a second fairing 1070b, also positioned between the tractor 1051 and the trailer 1052, but configured to deploy and retract vertically, rather than horizontally. FIG. 12I illustrates the second fairing 1070b in its deployed position, in which it at least partially seals the interface between the tractor 1051 and the trailer 1052. In FIG. 12J, the second fairing 1070b has been retracted, as indicated by arrow R to open or at least partially open the gap between the tractor 1051 and the trailer 1052. The second fairing 1070b can be selectively retracted during particular maneuvers, for example, if the tractor-trailer combination makes a sharp turn. Of course, the second fairing 1070b can also be retracted to access connections between the tractor 1051 and the trailer 1052, and to allow the tractor and trailer to be disconnected from each other.

Figure 12K:
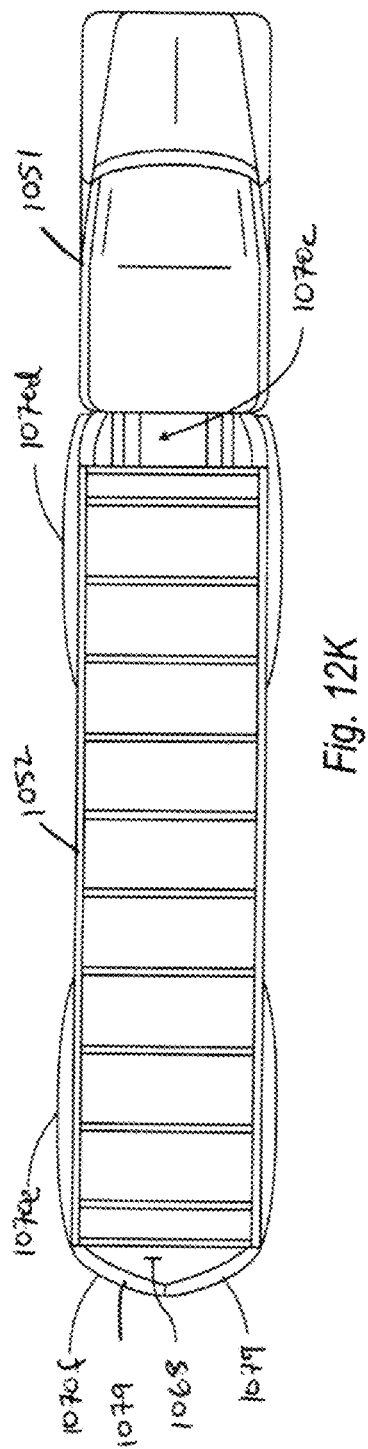
Figure 12L:
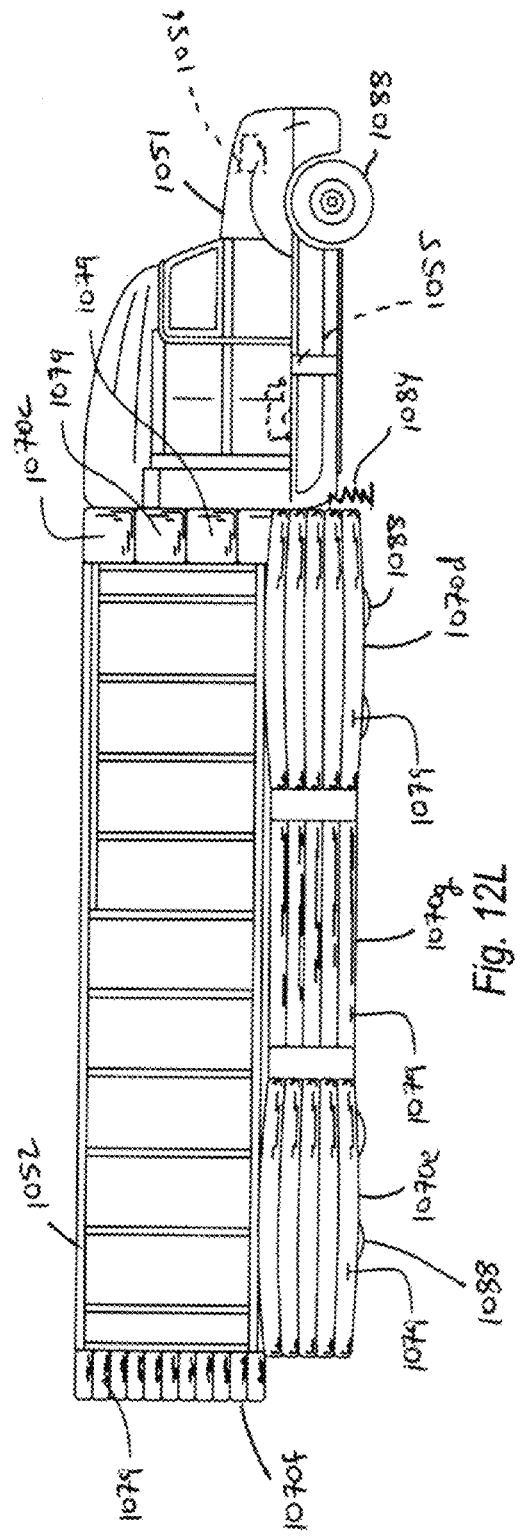

FIGS. 12K and 12L illustrate a top plan view and a side view, respectively, of a tractor 1051 and a trailer 1052 having deployable fairings configured in accordance with still further embodiments of the present technology. Referring first to FIG. 12K, the fairings can include a tractor-trailer fairing 1070c between the tractor 1051 and the trailer 1052, a pair of forward fairings 1070d, a pair of aft fairings 1070e, and a rear fairing 1070f. The tractor-trailer fairing 1070c can at least partially seal the gap between the tractor 1051 and the trailer 1052 in a manner generally similar to that described above with reference to FIGS. 12G-12J. The forward fairings 1070d and aft fairings 1070e can provide for streamlining over the rear wheels of the tractor 1051 and the wheels of the trailer 1052, respectively. The rear fairing 1070f can provide a tapered surface at the rear of the trailer 1052 to reduce boattail drag. Accordingly, the rear fairing 1070f can enclose a tapered space 1068 around the rearward facing surface of the trailer 1052. Any of the foregoing fairings can have a curved profile, as shown in FIG. 12K, or a flat profile.

As shown in FIG. 12L, an intermediate fairing 1070g can be located between the forward and aft fairings 1070d, 1070e. Any or all of the fairings can be formed from multiple segments 1079, each of which can be individually inflatable and/or deflatable. Accordingly, if one segment 1079 of the fairing is punctured, neighboring segments 1079 can maintain the overall shape of the fairing and accordingly maintain at least a significant portion of the efficiency benefit provided by the fairing. The fairings described above can be formed from a puncture-resistant material, for example, coated nylon, mylar, rubber, and/or plastics.

The compressed air (and/or other gas) described above as providing the force to deploy the fairings can also be used to drive other vehicle devices. For example, as shown in FIG. 12L, the tractor 1051 can include a deployable jack 1084 positioned to raise one or more of the wheels above the ground. In a particular embodiment, the jack 1084 can be positioned to raise the rear wheels of the tractor 1051 above the ground for service, or to add chains to the wheels. The jack 1084 can include a pneumatic piston-cylinder arrangement that is actuated by compressed air. In other embodiments, the jack 1084 can have a scissor-type arrangement as shown in FIG. 12L, or other arrangements suitable for elevating at least a portion of the tractor 1051.

In other embodiments, the compressed air can be used to provide still further functions for the vehicle. For example, compressed air can be used to activate pneumatic boots that shed ice, packed snow, and/or mud that would otherwise increase drag, rolling resistance, and may interfere with operation of the fairings and associated hardware. In still further embodiments, such compressed air-driven systems can be supplemented with or replaced by coatings that reduce or inhibit the ability for snow, ice, mud, and/or other debris from adhering to the surfaces of the vehicle. One suitable coating includes Ultra-Ever Dry available from UltraTech of Jacksonville, Fla.

Figure 12M:
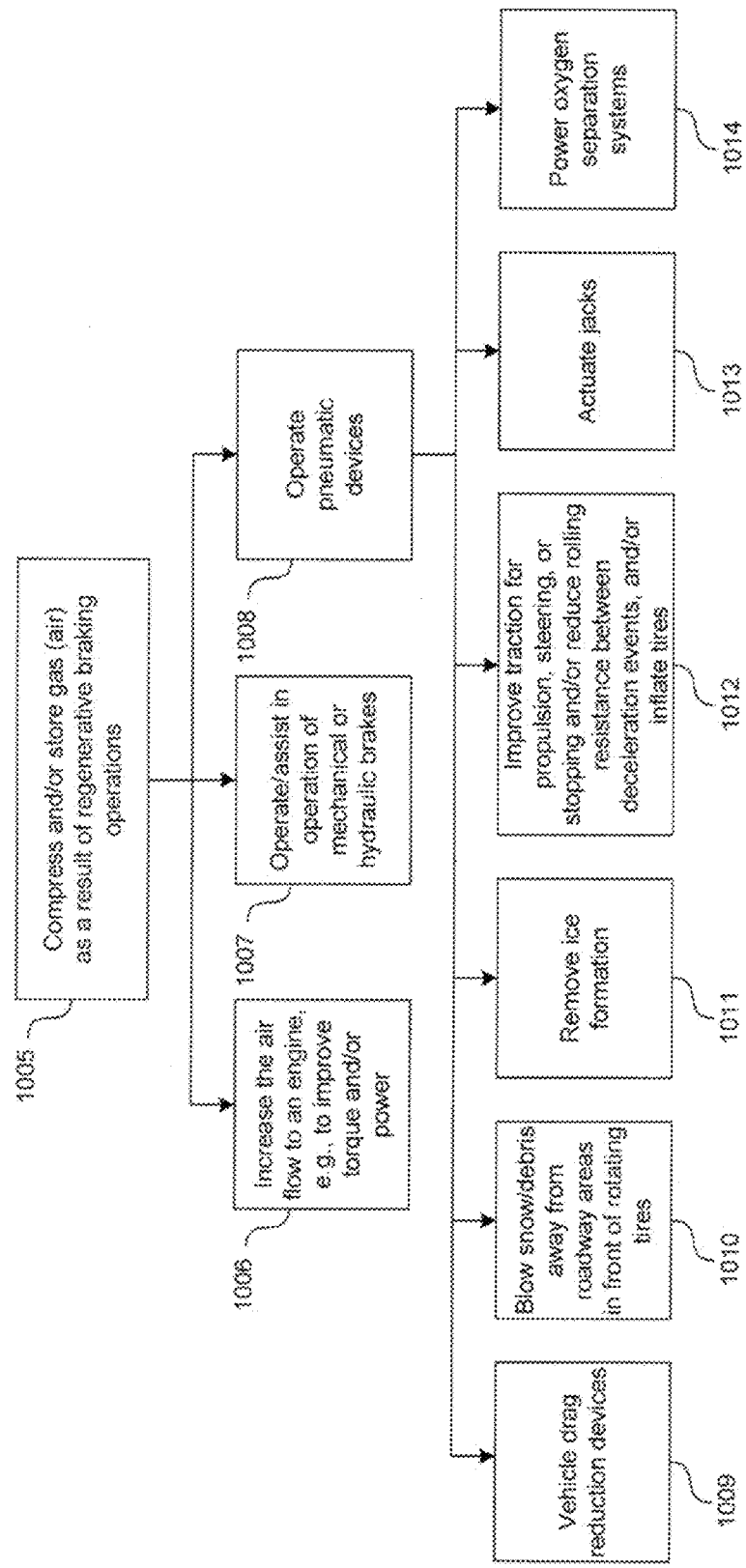

FIG. 12M illustrates a summary of representative processes that may be conducted in accordance with the foregoing discussion. Process portion 1005 includes compressing and/or storing a gas (e.g., air) as a result of regenerative braking operations. In process portion 1006, the compressed gas is used to increase the air flow to an engine, e.g., to improve torque and/or power delivered by the engine. In process portion 1007, the compressed gas is used to operate or assist in the operation of mechanical or hydraulic brakes. In process portion 1008, the compressed gas is used to operate other pneumatic devices. Such devices can include those that carry out the processes identified by blocks 1009-1014. Accordingly, such processes can be carried out by vehicle drag reduction devices, devices that blow snow and/or other debris away from roadway areas in front or rotating tires, devices that remove ice formations, improve traction for propulsion or steering, reduce stopping and/or rolling resistance, jacks that can be used to elevate the vehicle, and/or oxygen separation systems.

In yet further embodiments, the compressed air can be used to provide oxygen by molecular filtration for exothermic partial oxidation of fuels, including hydrocarbons, e.g., to produce hydrogen and carbon monoxide and/or carbon dioxide. The heat produced by this process can be used to elevate the temperature in an endothermic hydrocarbon reforming reaction, e.g., of the type carried out by the chemical reactors described above.

In particular embodiments, the compressed air stored in the storage tank 1071 (FIG. 12A) is generated by the pistons of the internal combustion engine used to power the tractor 1051. In still further particular embodiments, the compressed air is provided during a regenerative braking maneuver. Accordingly, compressing the air not only provides an actuation force for the fairings, jacks, and/or other pneumatically operated components of the vehicle, but also produces a braking effect as the air is compressed. FIGS. 13A-14B illustrate representative embodiments for compressing air and/or other constituents, including as part of a braking process.

Figure 13A:
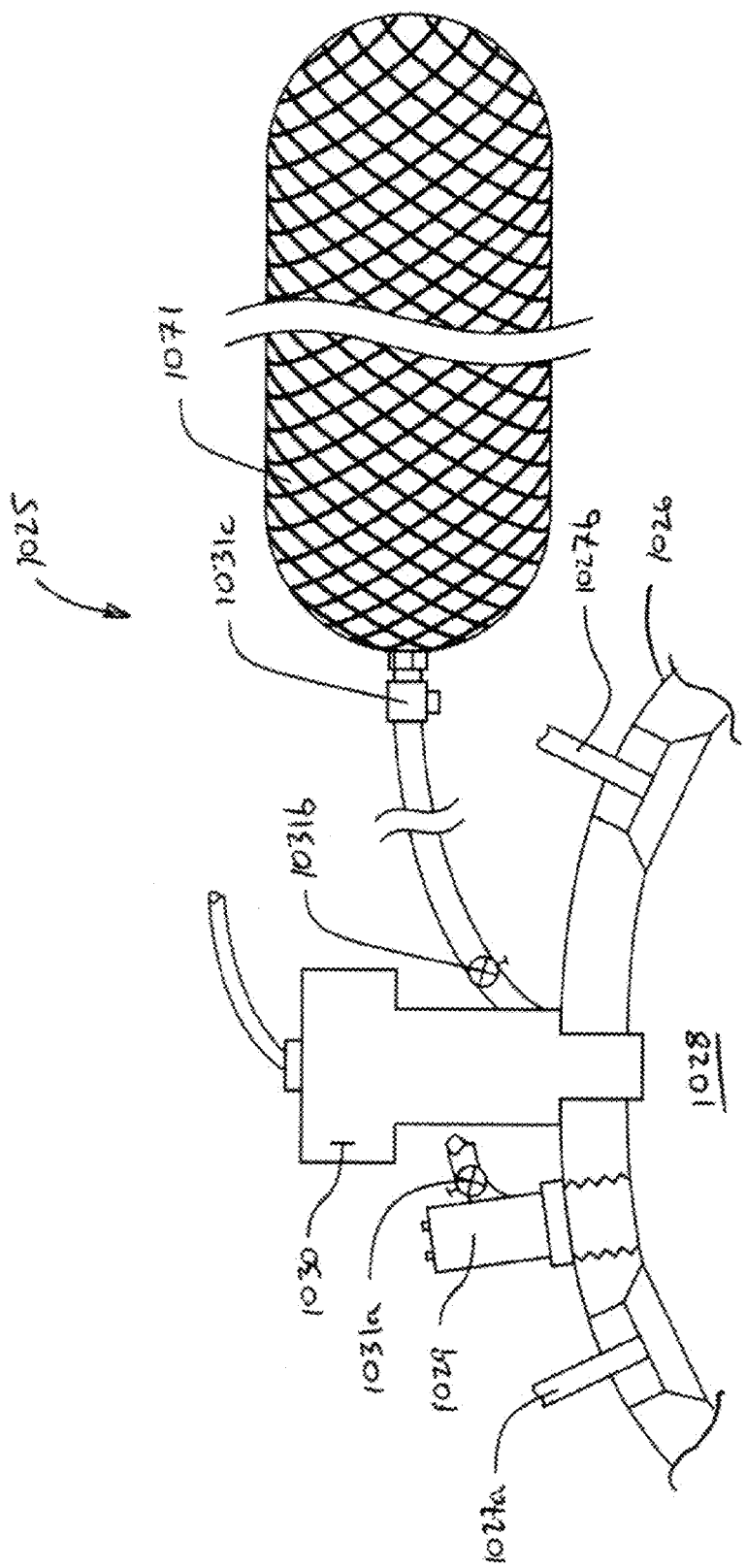
FIGS. 13A-13B illustrate systems and methods for obtaining compressed air from vehicle cylinders in accordance with embodiments of the present technology.

FIG. 13A is a schematic illustration of a compressed air system 1025 that includes a combustion chamber 1028 (a portion of which is shown in FIG. 13A) coupled to the compressed air storage tank 1071 in accordance with a particular embodiment of the present technology. The combustion chamber 1028 is positioned within a cylinder 1026 (a portion of which is shown in FIG. 13A) which includes an intake valve 1027a and an exhaust valve 1027b. The cylinder 1026 can also include a fuel injector and/or igniter 1030 (coupled to a fuel supply line 1034) and a glow plug 1029. The fuel injector/igniter 1030 and/or the glow plug 1029 can provide access to the interior of the cylinder, via which compressed air can be withdrawn and directed into the compressed air storage tank 1071. For example, the glow plug 1029 can include a first flow director valve 1031a and the fuel injector/igniter 1030 can include a second flow director valve 1031b, each of which is positioned to selectively allow compressed air from the combustion chamber 1028 into the compressed air storage tank 1071 via a storage tank valve 1031c. In other embodiments, a single flow director valve directs the compressed air exiting the cylinder 1026. In particular embodiments, air alone is compressed in the combustion chamber during a braking maneuver, and released into the storage tank 1071. In other embodiments, the air in the combustion chamber can be ignited prior to the piston (not visible in FIG. 13A) reaching top dead center, to provide a back force on the piston and crankshaft, which slows the vehicle in which the piston operates.

In particular embodiments, the compressed air or oxygen extracted from such compressed air is used to support partial oxidation of fuels (e.g., hydrocarbons) to produce hydrogen that is added to the combustion chamber 1028. In this way, the engine can be operated without throttling the inlet air supplied to the combustion chamber. By adaptively controlling the addition of hydrogen to the combustion chamber, embodiments of the system enable alternative fuels such as natural gas, methanol, ethanol, propane, ethane, methane and various other fuels to produce much higher fuel economy and engine performance, without throttling of the inlet air. Operation of the combustion chamber includes such benefits with homogeneous and stratified charge fuel-air mixtures, as described further below with reference to FIG. 13B.

Figure 13B:
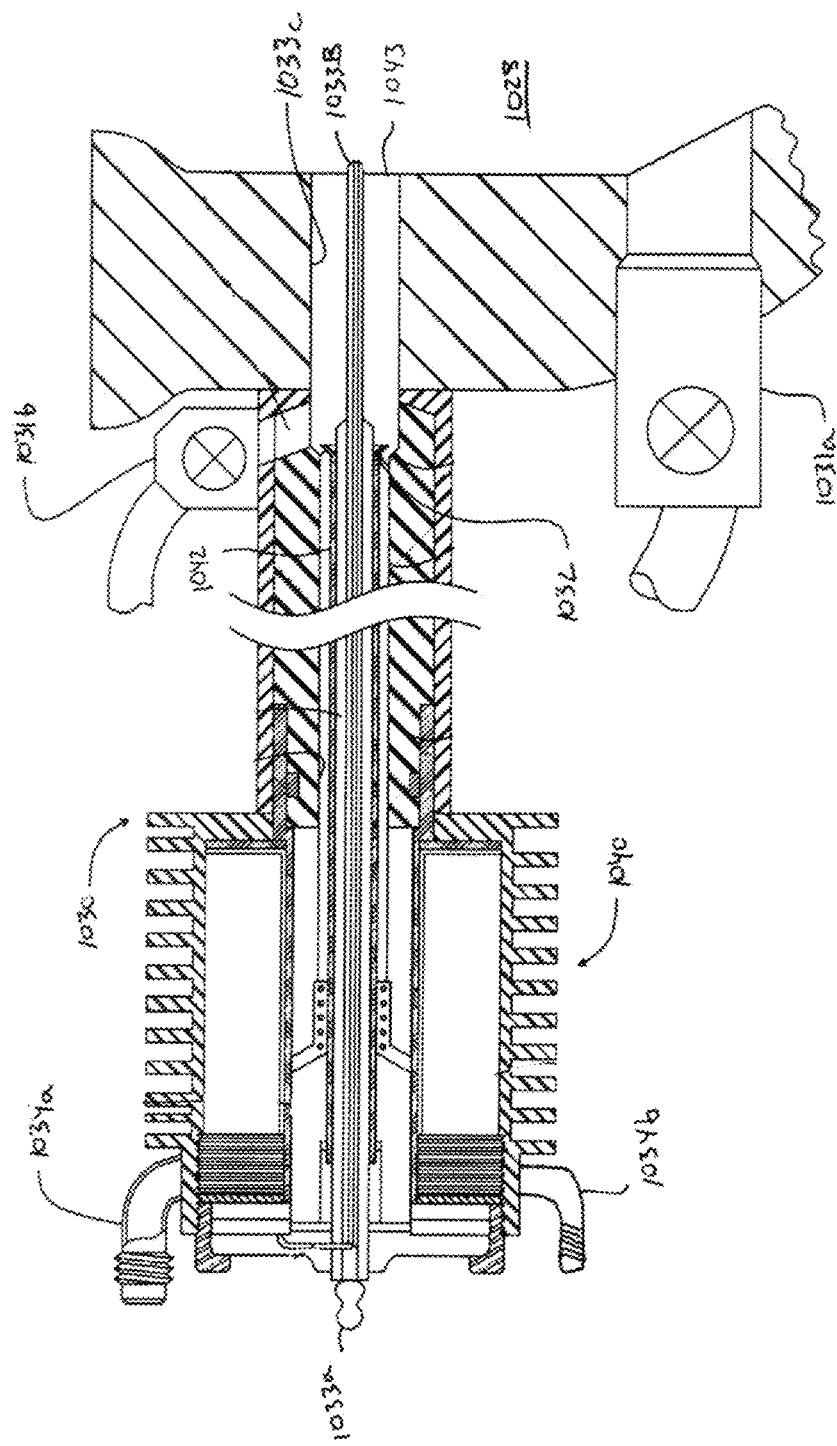

FIG. 13B is a partially schematic, cross-sectional illustration of a representative cylinder 1026 having several features generally similar to those described above with reference to FIG. 13A. As shown in FIG. 13B, the fuel injector/igniter includes the second flow director valve 1031b. The glow plug 1029 shown in FIG. 13A has been replaced with a dedicated first flow director valve 1031a. The fuel injector/igniter 1030 is coupled to a first fuel supply conduit 1034a which in turn directs fuel into the combustion chamber 1028 via a port 1043. An actuator assembly 1040 controls the injection process.

In operation, hydrogen (e.g., produced by the dissociation process described above with reference to FIG. 1) may be mixed with another fuel and supplied as a pressurized fluid through conduit the first fuel supply conduit 1034a or separately through a second fuel supply conduit 1034b. This arrangement can provide for numerous combinations that adaptively optimize or at least improve engine performance and efficiency including utilizing a suitable high voltage circuit to supply ignition through a conductor 1033a and electrodes 1033b and 1033c. The ignition can be by spark, ion acceleration, corona discharge and/or other suitable techniques, so as to combust the fuel admitted through a fuel control valve 1042 at an adaptively controlled/optimized time. Combinations of fuel mixture production include one or more injections of hydrogen and fuel during the intake and/or compression strokes to produce a homogeneous charge mixture. With the oxidant in the combustion chamber, one or more injections of fuel supplied from the first fuel conduit 1034a can produce a homogeneous charge, and subsequent injection of hydrogen supplied from the second fuel conduit 1034b can provide stratified charge ignition. In particular embodiments, one or more injections of suitable mixtures of hydrogen and other fuel selections can produce and ignite stratified charge fuel-air mixtures, and one or more injections of alternative fuel can produce stratified charge into which hydrogen is injected to combust the resulting stratified charge mixture with the oxidant in the combustion chamber. Further details of representative integrated fuel injector and igniter assemblies are described in co-pending U.S. Pat. No. 8,225,768, incorporated herein by reference. Further details of suitable oxygenated fuels, hydrogen-characterized fuels, and associated systems and methods are included in the following documents, each of which is incorporated herein by reference: U.S. Patent Publication No. US2011/0207062, filed Feb. 14, 2011, U.S. Pat. No. 8,070,835 and U.S. Pat. No. 8,365,700.

An advantage of particular embodiments described above is that hydrogen can be combusted with a hydrocarbon fuel in a manner that avoids the need for throttling the intake air. This can significantly reduce system complexity and/or significantly increase system efficiency, for systems that use fuels that require air throttling to produce satisfactory fuel-air ratios. In particular, due to its low molecular weight, hydrogen has a much higher velocity and mobility in a reaction environment and can accordingly oxidize and promote oxidation much more rapidly than other participants in the reaction. In particular embodiments, hydrogen can be the only fuel so as to further increase efficiency, but even in cases for which hydrogen supplements heavier fuels, the efficiency increases are expected to be significant. In any of these embodiments, the hydrogen can be obtained in a dissociation process) with a hydrocarbon, ammonia, urea, or another hydrogen donor as a reactant), or the hydrogen can obtained via another suitable process.

Figure 14A:
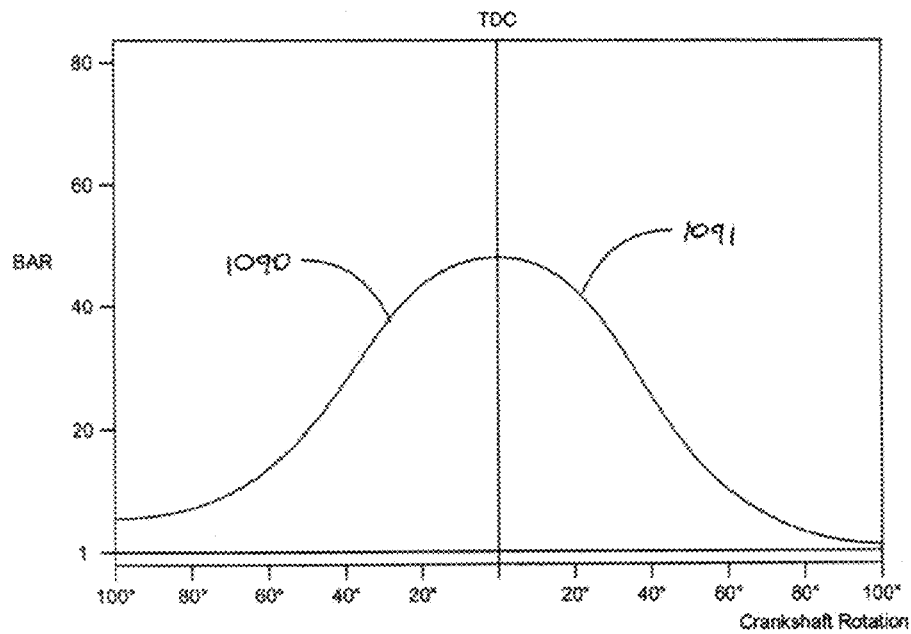
FIGS. 14A-14B are graphs illustrating cylinder pressure as a function of crankshaft angle during compression and expansion processes in accordance with embodiments of the present technology.

In either of the embodiments described above with reference to FIGS. 13A and 13B, the cylinder 1026 and associated piston and crankshaft can be operated in a manner different than that typically associated with an internal combustion engine operating as a propulsive power source, in order to produce compressed air. FIG. 14A illustrates cylinder pressure as a function of crankshaft rotation angle during a representative compression and expansion cycle. During the compression portion of the cycle 1090, air in the cylinder is compressed and during the expansion portion of the cycle 1091, the air is expanded and released from the cylinder.

Figure 14B:
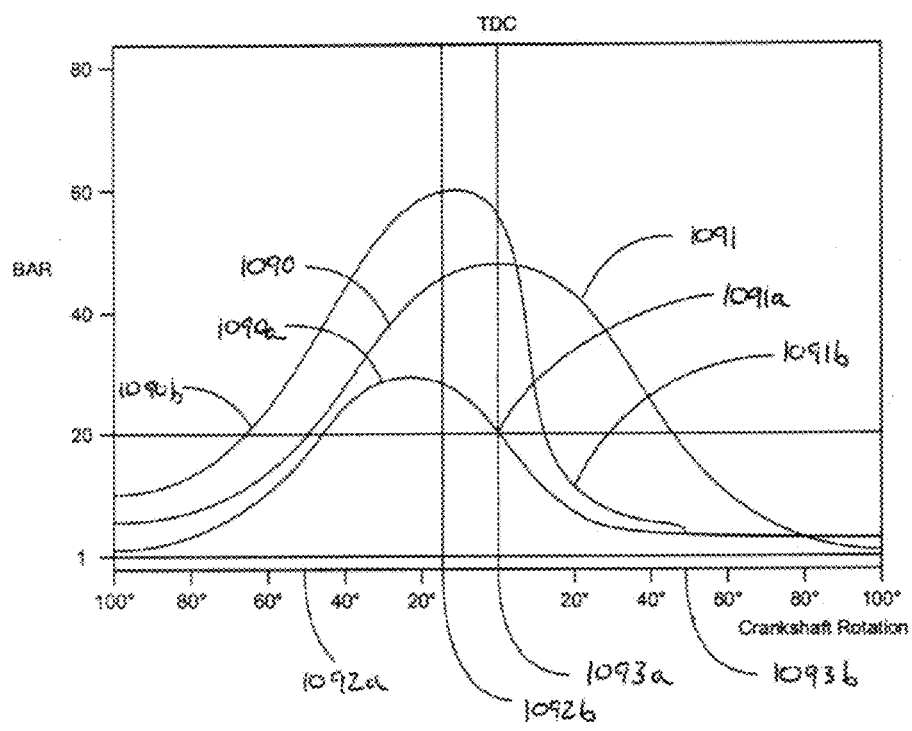

FIG. 14B illustrates the standard compression and expansion cycle portions 1090, 1091 along with two additional cycles used to compress air in accordance with embodiments of the present technology. A first cycle illustrated by a first compression portion 1090a and a first expansion portion 1091a are produced when the cylinder exhaust valve is opened early (as indicated by a first open crank angle 1092a), and closed early (as indicated by a first close crank angle 1093a). In another embodiment, illustrated by a second compression portion 1090b and a second expansion portion 1091b, the open and close crank angles are shifted to the right as indicated by a second open crank angle 1092b and a second close crank angle 1093b, in a manner that also produces highly compressed air (e.g., air compressed to 20 bars).

In particular embodiments described above with reference to FIGS. 14A and 14B, air alone is compressed in the cylinder to produce a back force (braking force) on the vehicle and to provide a source of compressed air. For multi-cylinder vehicles, some cylinders can perform an air compression function while others provide a propulsion function. The number of cylinders providing compressed air can depend upon the need for compressed air, the need for propulsion (e.g., in response to an acceleration command), and the need for braking (e.g., in response to a braking command), with the determination computed by an on-board controller or computer 1056 (shown in FIG. 12C). in still further embodiments, the compressed air obtained during a braking operation can be reintroduced to the cylinder during a power cycle (e.g., after top dead center) to provide further power in a regenerative manner.

In other embodiments, a cylinder performing a braking function can do so while combusting fuel, to increase the back force provided by the piston. In such embodiments, fuel can be injected into the cylinder after bottom dead center (e.g. to produce a stratified pattern), and can be combusted quickly, with a sufficient supply of oxygen to provide for not only combustion, but also insulation within the cylinder. The foregoing operation can be conducted with or without inlet air throttling. Inlet air throttling can produce additional backwork (e.g., braking) to further slow the vehicle. In still further embodiments, the inlet air can be drawn from the internal volume of the fairings discussed above, or other deployable and collapsible elements. For example, as the piston moves downwardly during an intake stroke, it can withdraw air from the inflatable element to quickly stow the element, while proving a braking function and/or re-storing the air as compressed air.

In a particular embodiment, an engine that is capable of producing 500 horsepower can be controlled by the flow director valve(s) for each combustion chamber, and one or more pneumatic loads to produce more than 500 horsepower of braking power if needed by developing a high pressure potential energy and/or work by converting the kinetic energy of the engine's flywheel and other drive train components, along with the kinetic energy of the vehicle. This energy can be stored in the compressed air storage tank described above to recapture much of the energy used during a braking operation if the compressed air in the braking cylinders is combusted, the heat energy produced by the combustion can also be stored in the compressed air tank. The compressed air or other gas can be used to actuate devices such as the fairings described above, or can be converted to other forms of energy. For example, the compressed gas can be directed through a turbo-alternator 1055 (shown in FIG. 12C) to produce electricity for various on-board applications that use electric power. Other applications include air conditioning (e.g., heating or cooling), defrosting, among others.

Existing transportation engines can also be retrofitted with suitable drives (e.g., gears, chains, or belts) that provide for more than doubling the torque applied to slow an engine by exiting and/or loading an existing or larger capacity electricity generator, such as an alternator. Such alternators can produce a much higher back-load on the vehicle and can provide a much higher voltage and/or current for relatively short periods of time between longer cooling periods. Such embodiments can be implemented by retrofitting the vehicle with an additional, high capacity alternator.

4. Further Representative Reactors

The following sections describe representative reactors and associated systems that may be used alone or in any of a variety of suitable combinations for carrying out one or more of the foregoing processes described above with reference to FIGS. 2-10E. In particular, any suitable component of the systems described in the following sections may replace or supplement a suitable component described in the foregoing sections.

In some embodiments, the reactants may be obtained on a local scale, the reactions may be conducted on a local scale, and the products may be used on a local scale to produce a localized result. In other embodiments, the reactants, reactions, products and overall effect of the process can have a much larger effect. For example, the technology can have continental and/or extra-continental scope. In particular embodiments, the technology can be deployed to preserve vast regions of permafrost, on a continental scale, and or preserve ecosystems located offshore from the preserved areas. In other embodiments, the technology can be deployed offshore to produce effects over large tracts of ocean waters. In still further, embodiments, the technology can be deployed on mobile systems that convey the benefits of the technology to a wide range of areas around the globe.

In general, the disclosed reactors dissociate, reform and/or respeciate a donor material (reactant) into multiple constituents (e.g., a first constituent and a second constituent). Particular aspects of the representative reactors described below are described in the context of specific reactants and products, e.g., a hydrogen and carbon bearing donor, a hydrogen-bearing product or constituent, and a carbon-bearing product or constituent. In certain other embodiments of the disclosed technology, the same or similar reactors may be used to process other reactants and/or form other products. For example, non-hydrogen feedstock materials (reactants) are used in at least some embodiments. In particular examples, sulfur dioxide can be processed in a non-combustion thermal reactor to produce sulfur and oxygen, and/or carbon dioxide can be processed to produce carbon and oxygen. In many of these embodiments, the resulting dissociation products can include a structural building block and/or a hydrogen-based fuel or other dissociated constituent. The structural building block includes compositions that may be further processed to produce architectural constructs. For example, the structural building blocks can include compounds or molecules resulting from the dissociation process and can include carbon, various organics (e.g. methyl, ethyl, or butyl groups or various alkenes), boron, nitrogen, oxygen, silicon, sulfur, halogens, and/or transition metals. In many applications the building block element does not include hydrogen. In a specific example, methane is dissociated to form hydrogen (or another hydrogen-bearing constituent) and carbon and/or carbon dioxide and/or carbon monoxide (structural building blocks). The carbon and/or carbon dioxide and/or carbon monoxide can be further processed to form polymers, graphene, carbon fiber, and/or another architectural construct. The architectural construct can include a self-organized structure (e.g., a crystal) formed from any of a variety of suitable elements, including the elements described above (carbon, nitrogen, boron, silicon, sulfur, and/or transition metals). In any of these embodiments, the architectural construct can form durable goods, e.g., graphene or carbon composites, and/or other structures.

Many embodiments are described in the context of hydrocarbons, e.g., methane. In other embodiments, suitable hydrogen-bearing feedstocks (e.g., reactants) include boranes (e.g., diborane), silanes (e.g., monosilane), nitrogen-containing compounds (e.g., ammonia), sulfides (e.g., hydrogen sulfide), alcohols (e.g., methanol), alkyl halides (e.g., carbon tetrachloride), aryl halides (e.g., chlorobenzene), and hydrogen halides (e.g., hydrochloric acid), among others. For example, silane can be thermally decomposed to form hydrogen as a gaseous product and silicon as a non-gaseous product. When the non-gaseous product includes silicon, the silicon can be reacted with nitrogen (e.g., from air) or with a halogen gas (e.g., recycled from a separate industrial process) to form useful materials, such as silicon nitride (e.g., as a structural material) or a silicon halide (e.g., as a non-structural material). In other embodiments, the feedstock material can be reacted to form only gaseous products or only non-gaseous products. For example, suitable hydrogen halides can be thermally decomposed to form a combination of hydrogen and halogen gas as the gaseous product with no accompanying non-gaseous product. In some embodiments, the gaseous product can include a gaseous fuel (e.g., hydrogen) and/or the non-gaseous product can include an elemental material (e.g., carbon or silicon). In some embodiments, the system can be configured for use in close proximity to a suitable source of the feedstock material. For example, the system can be configured for use near landfills and for processing methane that would otherwise be flared or released into the atmosphere. In other embodiments, the system can be configured for processing stranded well gas at oil fields, methane hydrates from the ocean floors or permafrost sources, and/or other feedstock materials 180 that would otherwise be wasted.

In some embodiments, the non-gaseous product can be further processed in a reactor. For example, the non-gaseous product can be a structural building block that can be further processed in the reactor to produce a structural material, e.g., a ceramic, a carbon structure, a polymeric structure, a film, a fiber (e.g., a carbon fiber or a silicon fiber), or a filter. Highly pure forms of the non-gaseous product can be especially well suited for forming semiconductor devices, photo-optical sensors, and filaments for optical transmission, among other products. The non-gaseous product can also be used without further processing and/or can be reacted to form materials useful for non-structural applications.

In other embodiments, the carbon can be used as a structural material or used as a reactant for producing a structural material. For example, the carbon can be a reactant for extracting silicon from silica as shown in Equations R1 and/or R2 below.

$$C + SiO_2 \rightarrow CO_2 + Si \qquad \text{Equation R1}$$

$$2C + SiO_2 \rightarrow 2CO + Si \qquad \text{Equation R2}$$

Silicon from the reactions shown in Equations R1 and R2 or as the non-gaseous product may be formed, for example, in a granular (e.g., powder) form, which can include controlled amounts of amorphous and/or crystalline material. For example, the operating temperature of the reactor can be programmed or otherwise controlled to control when, where, and/or whether the silicon is deposited in amorphous or crystalline form.

In some embodiments, silicon from the system can be reacted to form halogenated silanes or silicon halides, e.g., SiBrH$_3$, SiBrFH$_2$, SiBrH$_3$, SiBr$_3$H, SiCl$_2$H$_2$, SiBr$_4$, or SiCl$_4$, among others. Furthermore, silicon from the system may be made into various useful products and materials, such as products that are produced from or based on specialized forms of silicon (e.g., fumed silica), silicon-containing organic intermediates, and silicon-containing polymers, among others. Such products can be formed, for example, using suitable processes disclosed in U.S. Pat. Nos. 4,814,155, 4,414,364, 4,243,779, and 4,458,087, which are incorporated herein by reference. Silicon from the system 100 can also be used in the production of various substances, such as silicon carbide or silicon nitride, e.g., as shown in Equation R3.

$$3Si + 2N_2 \rightarrow Si_3N_4 \qquad \text{Equation R3}$$

Silicon nitride articles can be formed, for example, using silicon powders that are slip cast, pressure compacted, or injection molded and then converted into silicon nitride. The resulting articles can have density, fatigue, endurance, dielectric, and/or other properties well suited for a variety of high-performance applications. Silicon-nitride-based durable goods can be used, for example, in thermally and electrically insulating components that have lower densities and can operate at higher operating temperatures than metal alloys typically used in rocket engines, gas turbines, and positive-displacement combustion engines. Replacing such metal alloys, which typically consume critical supplies of cobalt, nickel, refractory metals, and rare earths with silicon nitride and/or carbon components, can enable far more cost-effective production of engines, fuel cells, and other equipment.

In addition to forming inorganic materials, the system can form a variety of useful organic materials. For example, the feedstock material can include propane or propylene, which can be reacted with ammonia in the first mode according to the reactions shown in Equations R4 and R5 to form acrylonitrile and hydrogen as the gaseous products or electrolytically disassociated in the second mode to generate electricity.

$$C_3H_8 + NH_3 \rightarrow CH_2=CH-C\equiv N + 4H_2 \qquad \text{Equation R4}$$

$$CH_3-CH=CH_2 + NH_3 \rightarrow CH_2=CH-C\equiv N + 3H_2 \qquad \text{Equation R5}$$

Subsequent processing of the gaseous products including acrylonitrile can include reacting the acrylonitrile to form polymers, rubbers, carbon fiber, and/or other materials well suited for use in durable goods (e.g., equipment to harness solar, wind, moving water, or geothermal energy). Accordingly, the overall energetics of processing propane or propylene using the system can be significantly more favorable than simple combustion. Furthermore, in some cases, processing propane or propylene using the system can produce little or no harmful pollution (e.g., environmentally released carbon dioxide, oxides of nitrogen, or particulates) or significantly less harmful pollution relative to simple combustion.

In some embodiments, one or more chemical reaction products from operation of the system can be used to form dielectric materials for use in durable goods. For example, the reaction products can be used to form polymers (e.g., polyimides, polyetherimides, parylenes, or fluoropolymers) and/or inorganic dielectrics (e.g., silicon dioxide or silicon nitride) that can incorporated into polymer-based nanodielectrics. Composites of inorganic and organic materials (one or both of which can be produced by operation of the system) can provide relatively high dielectric and mechanical strengths along with flexibility. Such materials can be well suited for use at a wide range of temperatures, such as temperatures ranging from cryogenic temperatures (e.g., about −200° C.) to heat-engine exhaust temperatures (e.g., about 500° C.). In other embodiments, the reaction products can be used to form thin films of inorganic amorphous carbon, silicon oxynitride, aluminum oxynitride, or other suitable materials. In some embodiments, the system can have dual-beam deposition and/or web-handling capabilities useful for processing suitable chemical reaction products (e.g., to form amorphous or crystalline carbon films).

In at least some embodiments, nitrogen can be obtained as a product or an exhaust stream. The nitrogen can be combined with hydrogen to produce ammonia and/or can be otherwise processed to form other useful materials such as Si$_3$N$_4$, AlN, BN, TiN, ZrN, TiCSi$_3$N$_4$, and/or suitable sialons.

While any one or more of the following representative reactors and associated components, devices and methodologies may be used in conjunction with the systems described above, certain reactors may have particularly synergistic and/or otherwise beneficial effects in such embodiments. For example, one or more induction reactors described below under heading 4.6 may be used to dissociate a hydrogen donor into a hydrogen-bearing constituent and a structural building block or precursor. Engine heat generated by the propulsion system carried by the truck or other transport platform may be used to dissociate a hydrogen donor generally in the manner described below under heading 4.7. Certain transport platforms (e.g., ocean-going platforms) can include solar concentrators to provide heat to one or more reactor(s) in the manner described below under heading 4.5. One or more of the foregoing solar concentrators may be used to perform both endothermic and exothermic reactions in the manner described below under heading 4.8. In cases for which the transport platform collects or otherwise obtains solid reactants, that may be dissociated into hydrogen or a hydrogen compound, a solar conveyor of the type described below under heading 4.4 may be used.

4.1 Representative Reactors with Transmissive Surfaces

Figure 15A:
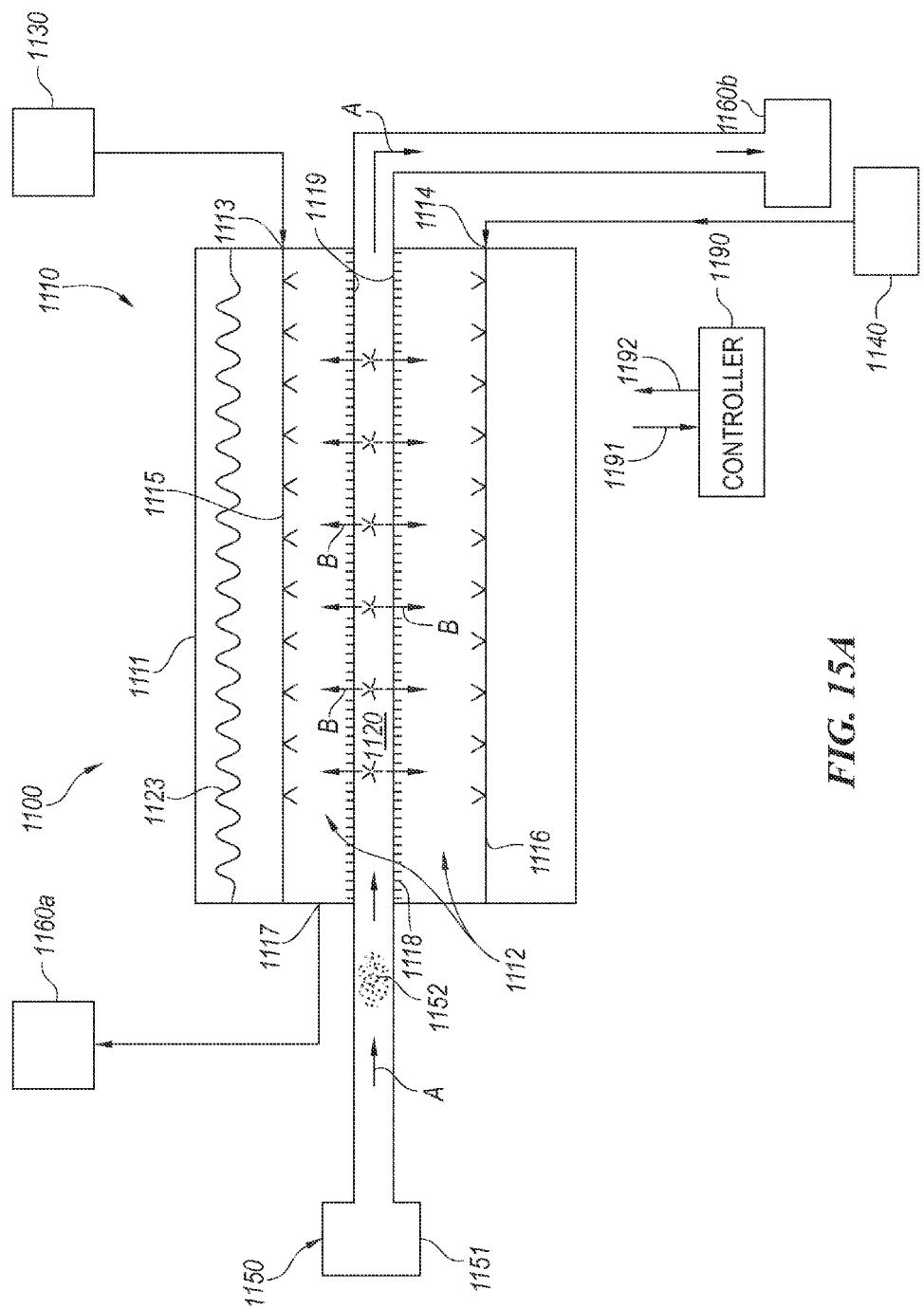
FIG. 15A is a partially schematic, partially cross-sectional illustration of a system having a reactor with transmissive surfaces in accordance with an embodiment of the disclosed technology.

FIG. 15A is a partially schematic illustration of a system 1100 that includes a reactor 1110. The reactor 1110 further includes a reactor vessel 1111 that encloses or partially encloses a reaction zone 1112. The reactor vessel 1111 has one or more transmissive surfaces positioned to facilitate the chemical reaction taking place within the reaction zone 1112. In a representative example, the reactor vessel 1111 receives a hydrogen donor provided by a donor source 1130 to a donor entry port 1113. For example, the hydrogen donor can include a nitrogenous compound such as ammonia or a compound containing carbon and hydrogen such as methane or another hydrocarbon. The hydrogen donor can be suitably filtered before entering the reaction zone 1112 to remove contaminants, e.g., sulfur. A donor distributor or manifold 1115 within the reactor vessel 1111 disperses or distributes the hydrogen donor into the reaction zone 1112. The reactor vessel 1111 also receives an oxygen donor such as an alcohol or steam from a steam/water source 1140 via a steam entry port 1114. A steam distributor 1116 in the reactor vessel 1111 distributes the steam into the reaction zone 1112. The reactor vessel 1111 can further include a heater 1123 that supplies heat to the reaction zone 1112 to facilitate endothermic reactions. Such reactions can include dissociating a compound such as a nitrogenous compound, or a compound containing hydrogen and carbon such as methane or another hydrocarbon into hydrogen or a hydrogen compound, and carbon or a carbon compound. The products of the reaction exit the reactor vessel 1111 via an exit port 1117 and are collected at a reaction product collector 1160a.

The system 1100 can further include a source 1150 of radiant energy and/or additional reactants, which provides constituents to a passage 1118 within the reactor vessel 1111.

For example, the radiant energy/reactant source 1150 can include a combustion chamber 1151 that provides hot combustion products 1152 to the passage 1118, as indicated by arrow A. A combustion products collector 1160b collects combustion products exiting the reactor vessel 1111 for recycling and/or other uses. In a particular embodiment, the combustion products 1152 can include carbon dioxide, carbon monoxide, water vapor, and other constituents. One or more transmissive surfaces 1119 are positioned between the reaction zone 1112 (which can be disposed annularly around the passage 1118) and an interior region 1120 of the passage 1118. The transmissive surface 1119 can accordingly allow radiant energy and/or a chemical constituent to pass radially outwardly from the passage 1118 into the reaction zone 1112, as indicated by arrows B. By delivering the radiant energy and/or chemical constituent(s) provided by the flow of combustion products 1152, the system 1100 can enhance the reaction taking place in the reaction zone 1112, for example, by increasing the reaction zone temperature and/or pressure, and therefore the reaction rate, and/or the thermodynamic efficiency of the reaction. Similarly, a chemical constituent such as water or steam can be recycled or otherwise added from the passage 1118 to replace water or steam that is consumed in the reaction zone 1112. In a particular aspect of this embodiment, the combustion products and/or other constituents provided by the source 1150 can be waste products from another chemical process (e.g., an internal combustion process). Accordingly, the foregoing process can recycle or reuse energy and/or constituents that would otherwise be wasted, in addition to facilitating the reaction at the reaction zone 1112.

The composition and structure of the transmissive surface 1119 can be selected to allow radiant energy to readily pass from the interior region 1120 of the passage 1118 to the reaction zone 1112. For example, the transmissive surface 1119 can include glass or another material that is transparent or at least partially transparent to infrared energy and/or radiant energy at other wavelengths that are useful for facilitating the reaction in the reaction zone 1112. In many cases, the radiant energy is present in the combustion product 1152 as an inherent result of the combustion process. In other embodiments, an operator can introduce additives into the stream of combustion products 1152 to increase the amount of energy extracted from the stream and delivered to the reaction zone 1112 in the form of radiant energy. For example, the combustion products 1152 can be seeded with sodium, potassium, and/or magnesium, which can absorb energy from the combustion products 1152 and radiate the energy outwardly through the transmissive surface 1119. In particular embodiments, the walls of the reaction zone 1112 can be dark and/or can have other treatments that facilitate drawing radiant energy into the reaction zone 1112. However, it is also generally desirable to avoid forming particulates and/or tars, which may be more likely to form on dark surfaces. Accordingly, the temperature on the reaction zone 1112 and the level of darkness can be controlled/selected to produce or to prevent tar/particulate formation.

In particular embodiments, the process performed at the reaction zone includes a conditioning process to produce darkened radiation receiver zones, for example, by initially providing heat to particular regions of the reaction zone 1112. After these zones have been heated sufficiently to cause dissociation, a small amount of a hydrogen donor containing carbon is introduced to cause carbon deposition or deposition of carbon-rich material. Such operations may be repeated as needed to restore darkened zones as desired.

In another particular aspect of this embodiment, the process can further includes preventing undesirable solids or liquids, such as particles and/or tars produced by dissociation of carbon donors, from forming at certain areas and/or blocking passageways including the entry port 1113 and the distributor 1115. This can be accomplished by supplying heat from the heater 1123 and/or the transmissive surface 1119 to an oxygen donor (such as steam) to heat the oxygen donor. When the oxygen donor is heated sufficiently, it can supply the required endothermic heat and react with the carbon donor without allowing particles or tar to be formed. For example, a carbon donor such as methane or another compound containing carbon and hydrogen receives heat from steam to form carbon monoxide and hydrogen and thus avoids forming of undesirable particles and/or tar.

As noted above, the combustion products 1152 can include steam and/or other constituents that may serve as reactants in the reaction zone 1112. Accordingly, the transmissive surface 1119 can be manufactured to selectively allow such constituents into the reaction zone 1112, in addition to or in lieu of admitting radiant energy into the reaction zone 1112. In a particular embodiment, the transmissive surface 1119 can be formed from a carbon crystal structure, for example, a layered graphene structure. The carbon-based crystal structure can include spacings (e.g., between parallel layers oriented transverse to the flow direction A) that are deliberately selected to allow water molecules to pass through. At the same time, the spacings can be selected to prevent useful reaction products produced in the reaction zone 1112 from passing out of the reaction zone. Suitable structures and associated methods are further disclosed in pending U.S. patent application Ser. No. 12/857,228 titled "ARCHITECTURAL CONSTRUCT HAVING FOR EXAMPLE A PLURALITY OF ARCHITECTURAL CRYSTALS" filed Feb. 14, 2011 and incorporated herein by reference. The structure used to form the transmissive surface 1119 can be carbon-based, as discussed above, and/or can be based on other elements capable of forming a self-organized structures, or constituents capable of modifying the surface of 1119 to pass or re-radiate particular radiation frequencies, and/or block or pass selected molecules. Such elements can include transition metals, boron, nitrogen, silicon, and sulfur, among others. In particular embodiments, the transmissive surface 1119 can include re-radiating materials selected to re-radiate energy at a wavelength that is particularly likely to be absorbed by one or more reactants in the reaction zone 1112. The walls of the reaction zone 1112 can include such material treatments in addition to or in lieu of providing such treatments to the transmissive surface 1119. Further details of such structures, materials and treatments are disclosed below in Section 4.2.

The system 1100 can further include a controller 1190 that receives input signals 1191 (e.g., from sensors) and provides output signals 1192 (e.g., control instructions) based at least in part on the inputs 1191. Accordingly, the controller 1190 can include suitable processor, memory and I/O capabilities. The controller 1190 can receive signals corresponding to measured or sensed pressures, temperatures, flow rates, chemical concentrations and/or other suitable parameters, and can issue instructions controlling reactant delivery rates, pressures and temperatures, heater activation, valve settings and/or other suitable actively controllable parameters. An operator can provide additional inputs to modify, adjust and/or override the instructions carried out autonomously by the controller 1190.

One feature of forming the transmissive surface 1119 from graphene or other crystal structures is that it can allow both radiant energy and useful constituents (e.g., water) to pass into the reaction zone 1112. In a particular embodiment, the spacing between graphene layers can be selected to "squeeze" or otherwise orient water molecules in a manner that tends to present the oxygen atom preferentially at the reaction zone 1112. Accordingly, those portions of the reaction that use the oxygen (e.g., oxidation or oxygenation steps) can proceed more readily than they otherwise would. As a result, this mechanism can provide a further avenue for facilitating the process of dissociating elements or compounds from the hydrogen donor and water, (and/or other reactants) and reforming suitable end products.

Figure 15B:
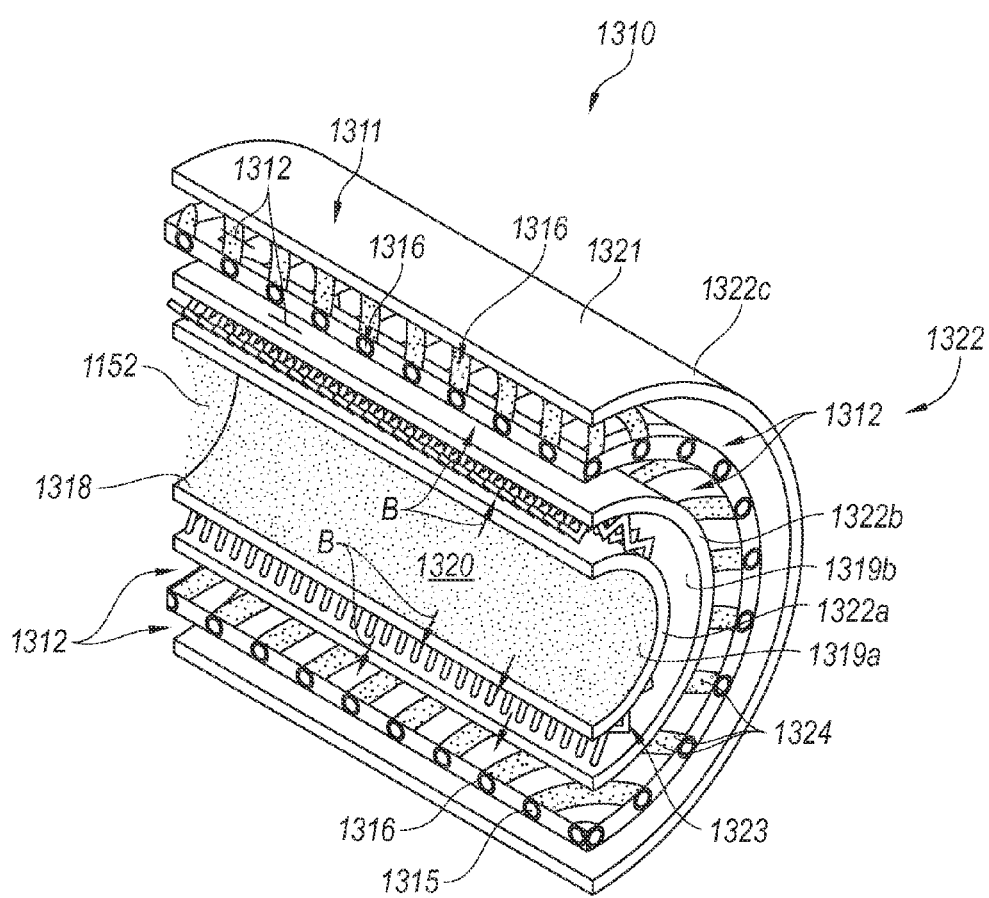
FIG. 15B is a partially schematic, cut-away illustration of a portion of a reactor having transmissive surfaces positioned annularly in accordance with an embodiment of the disclosed technology.

FIG. 15B is a partially schematic, partially cut-away illustration of a reactor 1310 that includes a vessel 1311 formed from three annularly (e.g., concentrically) positioned conduits 1322. Accordingly, the reactor 1310 can operate in a continuous flow manner. As used herein, "continuous flow" refers generally to a process in which reactants and products can be provided to and removed from the reactor vessel continuously without halting the reaction to reload the reaction zone with reactants. In other embodiments, the reactor 1310 can operate in a batch manner during which reactants are intermittently supplied to the reaction zone and products are intermittently removed from the reaction zone. The three conduits 1322 include a first or inner conduit 1322a, a second or intermediate conduit 1322b, and a third or outer conduit 1322c. The first conduit 1322a bounds a combustion products passage 1318 and accordingly has an interior region 1320 through which the combustion products 1152 pass. The first conduit 1322a has a first transmissive surface 1319a through which radiant energy passes in a radially outward direction, as indicated by arrows B. In a particular aspect of this embodiment, the annular region between the first conduit 1322a and the second conduit 1322b houses a heater 1323, and the annular region between the second conduit 1322b and the third conduit 1322c houses a reaction zone 1312. The heater 1323 together with the radiant heat from the combustion products 1152 provides heat to the reaction zone 1312. Accordingly, the second conduit 1322b can include a second transmissive surface 1319b that allows radiant energy from both the combustion products 1152 and the heater 1323 to pass radially outwardly into the reaction zone 1312. In a particular aspect of this embodiment, the first transmissive surface 1319a and the second transmissive surface 1319b are not transmissible to chemical constituents of the combustion products 1152, in order to avoid contact (e.g., corrosive or other damaging contact) between the combustion products 1152 and the heater 1323. In another embodiment, the heater 1323 can be manufactured (e.g., with appropriate coatings, treatments, or other features) in a manner that protects it from chemical constituents passing through the first and second transmissive surfaces 1319a, 1319b. In still another embodiment, the heater 1323 can be positioned outwardly from the reaction zone 1312. In any of these embodiments, the heater 1323 can include an electrical resistance heater, an induction heater or another suitable device. In at least some instances, the heater 1323 is powered by combusting a portion of the hydrogen produced in the reaction zone 1312. In other embodiments, combustion is performed in the reactor itself, for example, with the second conduit 1322b serving as a gas mantle for radiating energy at frequencies selected to accelerate the desired reactions in reaction zone 1312.

In any of the forgoing embodiments, the reaction zone 1312 can house one or more steam distributors 1316 and one or more hydrogen donor distributors 1315. Each of the distributors 1315, 1316 can include pores 1324 and/or other apertures, openings or passages that allow chemical reactants to enter the reaction zone 1312. The donor distributors 1315, 1316 can include one or more spiral conduits, including, e.g., conduits arranged in a braided fashion to distribute reactants into the reaction zone uniformly in the axial, radial and circumferential directions. The reaction zone 1312 is bounded by the third conduit 1322c which can have an insulated reactor outer surface 1321 to conserve heat within the reaction zone 1312. During operation, the reaction taking place in the reaction zone 1312 can be controlled by adjusting the rate at which steam and the hydrogen donor enter the reaction zone 1312, the rate at which heat enters the reaction zone 1312 (via the combustion product passage 1318 and/or the heater 1323) and other variables, including the pressure at the reaction zone 1312. Appropriate sensors and control feedback loops carry out these processes autonomously, with optional controller intervention, as described above with reference to FIG. 15A.

Still further embodiments of suitable reactors with transmissive surfaces are disclosed in pending U.S. application Ser. No. 13/026,996, filed Feb. 14, 2011, and incorporated herein by reference.

4.2 Representative Reactors with Re-Radiative Components

Figure 16A:
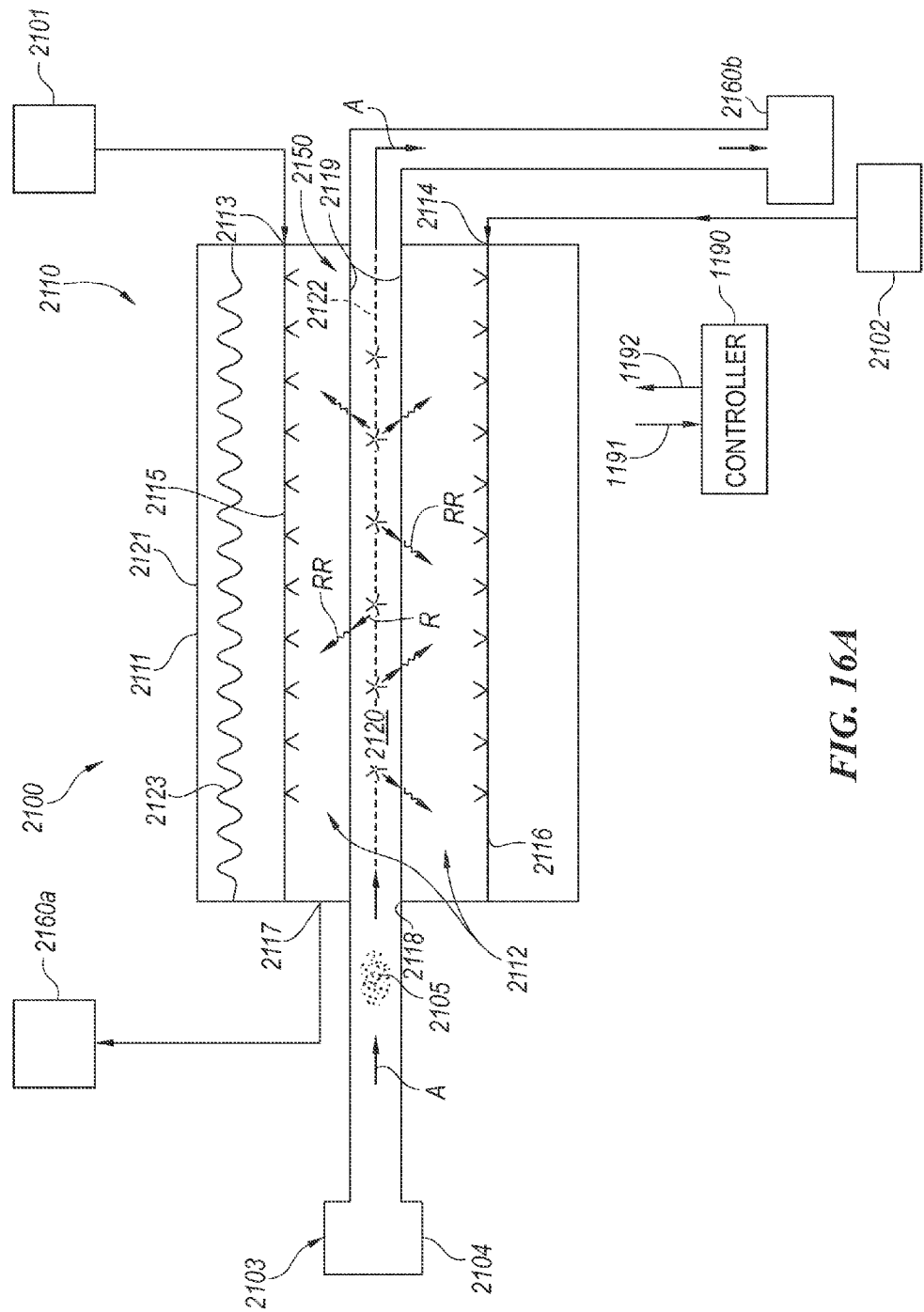
FIG. 16A is a partially schematic, partially cross-sectional illustration of a system having a reactor with a re-radiation component in accordance with an embodiment of the presently disclosed technology.

FIG. 16A is a partially schematic illustration of a system 2100 that includes a reactor 2110 having one or more selective (e.g., re-radiative) surfaces in accordance with embodiments of the disclosure. The reactor 2110 further includes a reactor vessel 2111 having an outer surface 2121 that encloses or partially encloses a reaction zone 2112. In a representative example, the reactor vessel 2111 receives a hydrogen donor provided by a donor source 2101 to a donor entry port 2113. For example, the hydrogen donor can include methane or another hydrocarbon. A donor distributor or manifold 2115 within the reactor vessel 2111 disperses or distributes the hydrogen donor into the reaction zone 2112. The reactor vessel 2111 also receives steam from a steam/water source 2102 via a steam entry port 2114. A steam distributor 2116 in the reactor vessel 2111 distributes the steam into the reaction zone 2112. The reactor vessel 2111 can still further include a heater 2123 that supplies heat to the reaction zone 2112 to facilitate endothermic reactions. Such reactions can include dissociating methane or another hydrocarbon into hydrogen or a hydrogen compound, and carbon or a carbon compound. The products of the reaction (e.g., carbon and hydrogen) exit the reactor vessel 2111 via an exit port 2117 and are collected at a reaction product collector 2160a.

The system 2100 can further include a source 2103 of radiant energy and/or additional reactants, which provides constituents to a passage 2118 within the reactor vessel 2111. For example, the radiant energy/reactant source 2103 can include a combustion chamber 2104 that provides hot combustion products 2105 to the passage 2118, as indicated by arrow A. In a particular embodiment, the passage 2118 is concentric relative to a passage centerline 2122. In other embodiments, the passage 2118 can have other geometries. A combustion products collector 2160b collects combustion products exiting the reactor vessel 2111 for recycling and/or other uses. In a particular embodiment, the combustion products 2105 can include carbon monoxide, water vapor, and other constituents.

One or more re-radiation components 2150 are positioned between the reaction zone 2112 (which can be disposed annularly around the passage 2118) and an interior region 2120 of the passage 2118. The re-radiation component 2150 can accordingly absorb incident radiation R from the passage 2118 and direct re-radiated energy RR into the reaction zone 2112. The re-radiated energy RR can have a wavelength spectrum or distribution that more closely matches, approaches, overlaps and/or corresponds to the absorption spectrum of at least one of the reactants and/or at least one of the resulting products. By delivering the radiant energy at a favorably shifted wavelength, the system 2100 can enhance the reaction taking place in the reaction zone 2112, for example, by increasing the efficiency with which energy is absorbed by the reactants, thus increasing the reaction zone temperature and/or pressure, and therefore the reaction rate, and/or the thermodynamic efficiency of the reaction. In a particular aspect of this embodiment, the combustion products 2105 and/or other constituents provided by the source 2103 can be waste products from another chemical process (e.g., an internal combustion process). Accordingly, the foregoing process can recycle or reuse energy and/or constituents that would otherwise be wasted, in addition to facilitating the reaction at the reaction zone 2112.

In at least some embodiments, the re-radiation component 2150 can be used in conjunction with, and/or integrated with, a transmissive surface 2119 that allows chemical constituents (e.g., reactants) to readily pass from the interior region 2120 of the passage 2118 to the reaction zone 2112. Further details of representative transmissive surfaces were discussed above under heading 4.1. In other embodiments, the reactor 2110 can include one or more re-radiation components 2150 without also including a transmissive surface 2119. In any of these embodiments, the radiant energy present in the combustion product 2105 may be present as an inherent result of the combustion process. In other embodiments, an operator can introduce additives into the stream of combustion products 2105 (and/or the fuel that produces the combustion products) to increase the amount of energy extracted from the stream and delivered to the reaction zone 2112 in the form of radiant energy. For example, the combustion products 2105 (and/or fuel) can be seeded with sources of sodium, potassium, and/or magnesium, which can absorb energy from the combustion products 2105 and radiate the energy outwardly into the reaction zone 2112 at desirable frequencies. These illuminant additives can be used in addition to the re-radiation component 2150.

Figure 16B:
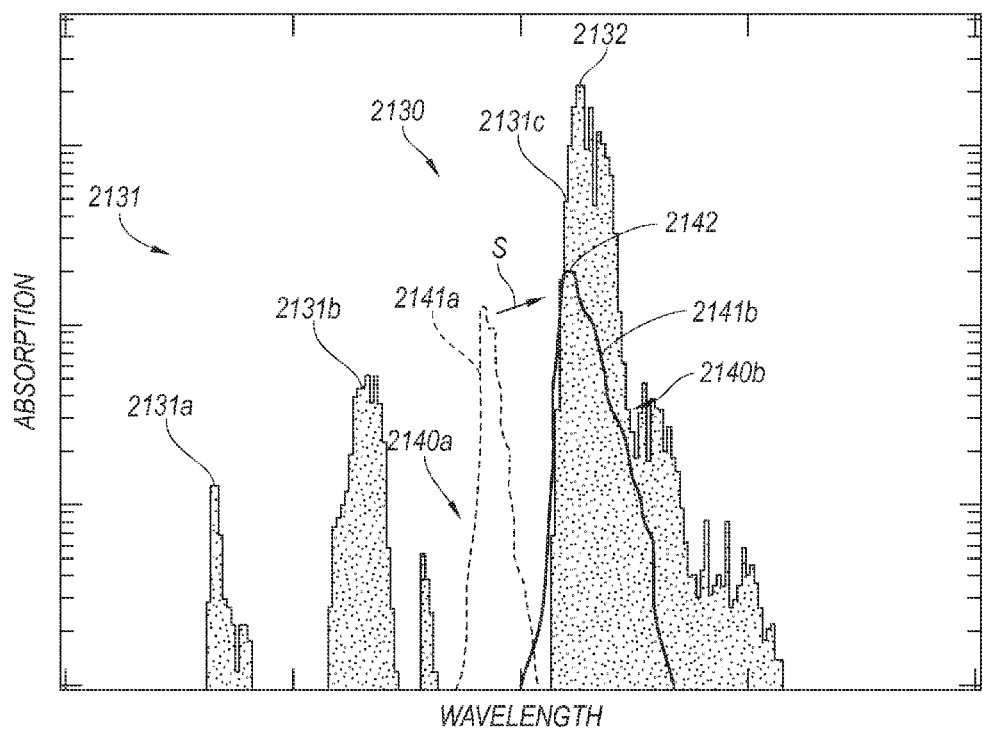
FIG. 16B illustrates absorption characteristics as a function of wavelength for a representative reactant and re-radiation material, in accordance with an embodiment of the presently disclosed technology.

FIG. 16B is a graph presenting absorption as a function of wavelength for a representative reactant (e.g., methane) and a representative re-radiation component. FIG. 16B illustrates a reactant absorption spectrum 2130 that includes multiple reactant peak absorption ranges 2131, three of which are highlighted in FIG. 16B as first, second and third peak absorption ranges 2131a, 2131b, 2131c. The peak absorption ranges 2131 represent wavelengths for which the reactant absorbs more energy than at other portions of the spectrum 2130. The spectrum 2130 can include a peak absorption wavelength 2132 within a particular range, e.g., the third peak absorption range 2131c.

FIG. 16B also illustrates a first radiant energy spectrum 2140a having a first peak wavelength range 2141a. For example, the first radiant energy spectrum 2140a can be representative of the emission from the combustion products 2105 described above with reference to FIG. 16A. After the radiant energy has been absorbed and re-emitted by the re-radiation component 2150 described above, it can produce a second radiant energy spectrum 2140b having a second peak wavelength range 2141b, which in turn includes a re-radiation peak value 2142. In general terms, the function of the re-radiation component 2150 is to shift the spectrum of the radiant energy from the first radiant energy spectrum 2140a and peak wavelength range 2141a to the second radiant energy spectrum 2140b and peak wavelength range 2141b, as indicated by arrow S. As a result of the shift, the second peak wavelength range 2141b is closer to the third peak absorption range 2131c of the reactant than is the first peak wavelength range 2141a. For example, the second peak wavelength range 2141b can overlap with the third peak absorption range 2131c and in a particular embodiment, the re-radiation peak value 2142 can be at, or approximately at the same wavelength as the reactant peak absorption wavelength 2132. In this manner, the re-radiation component more closely aligns the spectrum of the radiant energy with the peaks at which the reactant efficiently absorbs energy. Representative structures for performing this function are described in further detail below with reference to FIG. 16C.

Figure 16C:
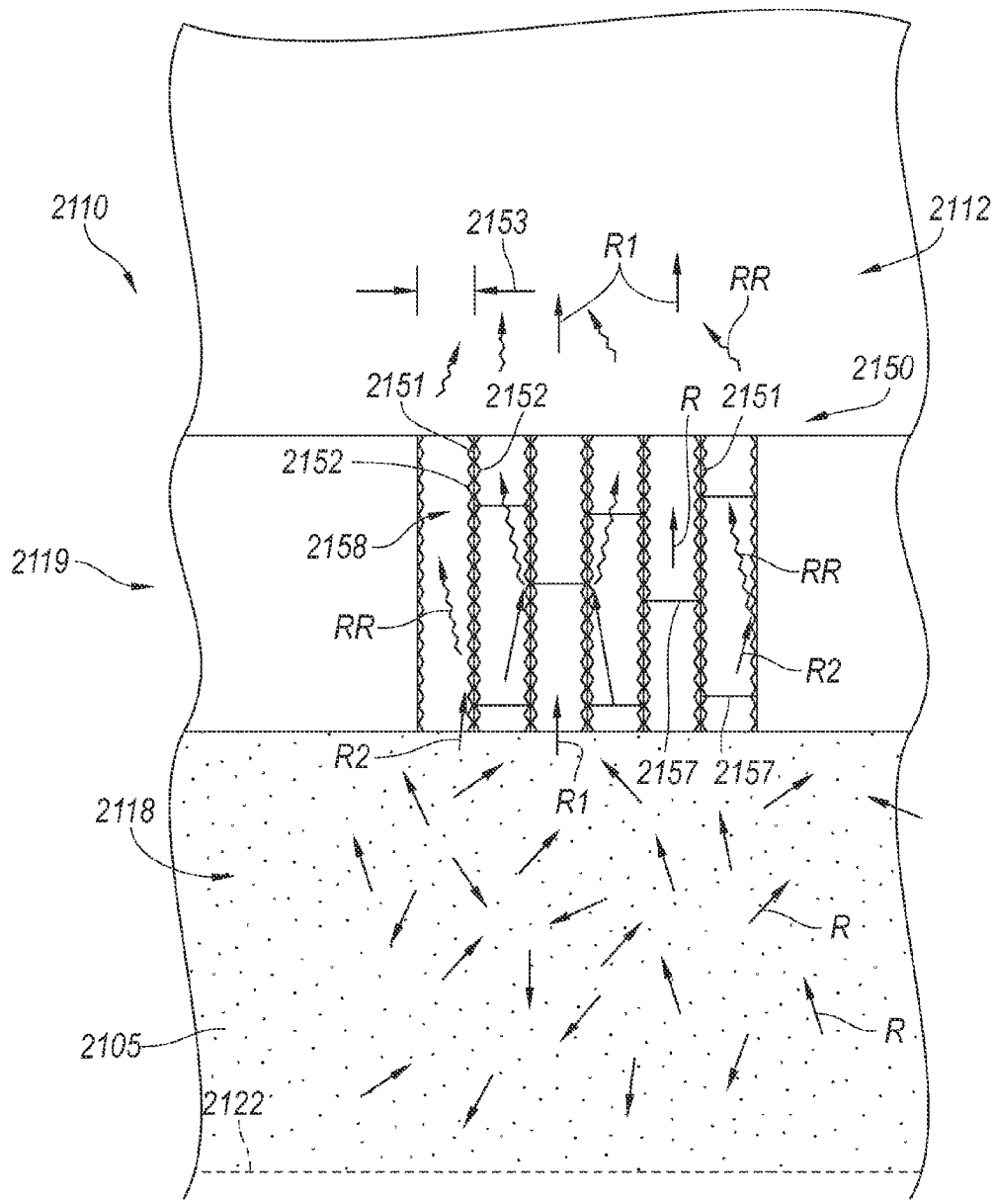
FIG. 16C is an enlarged, partially schematic illustration of a portion of the reactor shown in FIG. 16A having a re-radiation component configured in accordance with a particular embodiment of the presently disclosed technology.

FIG. 16C is a partially schematic, enlarged cross-sectional illustration of a portion of the reactor 2110 described above with reference to FIG. 16A, having a re-radiation component 2150 configured in accordance with a particular embodiment of the technology. The re-radiation component 2150 is positioned between the passage 2118 (and the radiation energy R in the passage 2118), and the reaction zone 2112. The re-radiation component 2150 can include layers 2151 of material that form spaced-apart structures 2158, which in turn carry a re-radiative material 2152. For example, the layers 2151 can include graphene layers or other crystal or self-orienting layers made from suitable building block elements such as carbon, boron, nitrogen, silicon, transition metals, and/or sulfur. Carbon is a particularly suitable constituent because it is relatively inexpensive and readily available. In fact, it is a target output product of reactions that can be completed in the reaction zone 2112. Further details of suitable structures are disclosed in co-pending U.S. application Ser. No. 12/857,228 previously incorporated herein by reference. Each structure 2158 can be separated from its neighbor by a gap 2153. The gap 2153 can be maintained by spacers 2157 extending between neighboring structures 2158. In particular embodiments, the gaps 2153 between the structures 2158 can be from about 2.5 microns to about 25 microns wide. In other embodiments, the gap 2153 can have other values, depending, for example, on the wavelength of the incident radiative energy R. The spacers 2157 are positioned at spaced-apart locations both within and perpendicular to the plane of FIG. 16C so as not to block the passage of radiation and/or chemical constituents through the component 2150.

The radiative energy R can include a first portion R1 that is generally aligned parallel with the spaced-apart layered structures 2158 and accordingly passes entirely through the re-radiation component 2150 via the gaps 2153 and enters the reaction zone 2112 without contacting the re-radiative material 2152. The radiative energy R can also include a second portion R2 that impinges upon the re-radiative material 2152 and is accordingly re-radiated as a re-radiated portion RR into the reaction zone 2112. The reaction zone 2112 can accordingly include radiation having different energy spectra and/or different peak wavelength ranges, depending upon whether the incident radiation R impinged upon the re-radiative material 2152 or not. This combination of energies in the reaction zone 2112 can be beneficial for at least some reactions. For example, the shorter wavelength, higher frequency (higher energy) portion of the radiative energy can facilitate the basic reaction taking place in the reaction zone 2112, e.g., disassociating methane in the presence of steam to form carbon monoxide and hydrogen. The longer wavelength, lower frequency (lower energy) portion can prevent the reaction products from adhering to surfaces of the reactor 2110, and/or can separate such products from the reactor surfaces. In particular embodiments, the radiative energy can be absorbed by methane in the reaction zone 2112, and in other embodiments, the radiative energy can be absorbed by other reactants, for example, the steam in the reaction zone 2112, or the products. In at least some cases, it is preferable to absorb the radiative energy with the steam. In this manner, the steam receives sufficient energy to be hot enough to complete the endothermic reaction within the reaction zone 2112, without unnecessarily heating the carbon atoms, which may potentially create particulates or tar if they are not quickly oxygenated after dissociation.

The re-radiative material 2152 can include a variety of suitable constituents, including iron carbide, tungsten carbide, titanium carbide, boron carbide, and/or boron nitride. These materials, as well as the materials forming the spaced-apart structures 2158, can be selected on the basis of several properties including corrosion resistance and/or compressive loading. For example, loading a carbon structure with any of the foregoing carbides or nitrides can produce a compressive structure. An advantage of a compressive structure is that it is less subject to corrosion than is a structure that is under tensile forces. In addition, the inherent corrosion resistance of the constituents of the structure (e.g., the foregoing carbides and nitrides) can be enhanced because, under compression, the structure is less permeable to corrosive agents, including steam which may well be present as a reactant in the reaction zone 2112 and as a constituent of the combustion products 2105 in the passage 2118. The foregoing constituents can be used alone or in combination with phosphorus, calcium fluoride and/or another phosphorescent material so that the energy re-radiated by the re-radiative material 2152 may be delayed. This feature can smooth out at least some irregularities or intermittencies with which the radiant energy is supplied to the reaction zone 2112.

Another suitable re-radiative material 2152 includes spinel or another composite of magnesium and/or aluminum oxides. Spinel can provide the compressive stresses described above and can shift absorbed radiation to the infrared so as to facilitate heating the reaction zone 2112. For example, sodium or potassium can emit visible radiation (e.g., red/orange/yellow radiation) that can be shifted by spinel or another alumina-bearing material to the IR band. If both magnesium and aluminum oxides, including compositions with colorant additives such as magnesium, aluminum, titanium, chromium, nickel, copper and/or vanadium, are present in the re-radiative material 2152, the re-radiative material 2152 can emit radiation having multiple peaks, which can in turn allow multiple constituents within the reaction zone 2112 to absorb the radiative energy.

The particular structure of the re-radiation component 2150 shown in FIG. 16C includes gaps 2153 that can allow not only radiation to pass through, but can also allow constituents to pass through. Accordingly, the re-radiation component 2150 can also form the transmissive surface 2119, which, as described above with reference to FIG. 16A, can further facilitate the reaction in the reaction zone 2112 by admitting reactants.

Still further embodiments of suitable reactors with re-radiative components are disclosed in pending U.S. application Ser. No. 13/027,015, filed Feb. 14, 2011, and incorporated herein by reference.

4.3 Representative Reactors with Heat Pipes and Heat Pumps

Figure 17A:
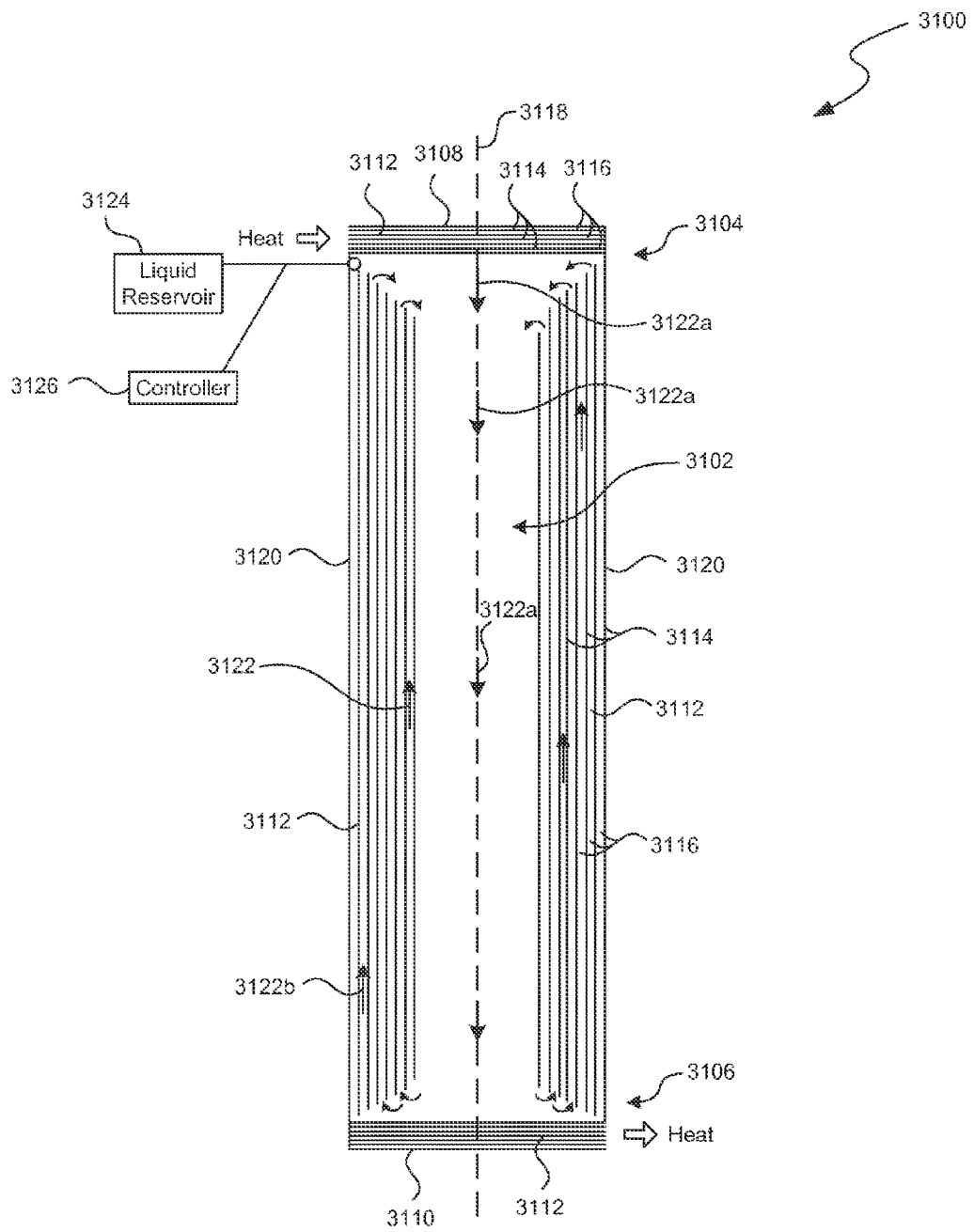
FIG. 17A is a schematic cross-sectional view of a thermal transfer device configured in accordance with an embodiment of the present technology.

FIG. 17A is a schematic cross-sectional view of a thermal transfer device 3100 ("device 3100") configured in accordance with an embodiment of the present technology. As shown in FIG. 17A, the device 3100 can include a conduit 3102 that has an input portion 3104, an output portion 3106 opposite the input portion 3104, and a sidewall 3120 between the input and output portions 3104 and 3106. The device 3100 can further include a first end cap 3108 at the input portion 3104 and a second end cap 3110 at the output portion 3106. The device 3100 can enclose a working fluid 3122 (illustrated by arrows) that changes between a vapor phase 3122a and a liquid phase 3122b during a vaporization-condensation cycle.

In selected embodiments, the device 3100 can also include one or more architectural constructs 3112. Architectural constructs 3112 are synthetic matrix characterizations of crystals that are primarily comprised of graphene, graphite, boron nitride, and/or another suitable crystal. The configuration and the treatment of these crystals heavily influence the properties that the architectural construct 3112 will exhibit when it experiences certain conditions. For example, as explained in further detail below, the device 3100 can utilize architectural constructs 3112 for their thermal properties, capillary properties, sorptive properties, catalytic properties, and electromagnetic, optical, and acoustic properties. As shown in FIG. 17A, the architectural construct 3112 can be arranged as a plurality of substantially parallel layers 3114 spaced apart from one another by a gap 3116. In various embodiments, the layers 3114 can be as thin as one atom. In other embodiments, the thickness of the individual layers 3114 can be greater and/or less than one atom and the width of the gaps 3116 between the layers 3114 can vary. Methods of fabricating and configuring architectural constructs, such as the architectural constructs 3112 shown in FIG. 17A, are described in U.S. patent application Ser. No. 12/857,228 previously incorporated herein by reference.

As shown in FIG. 17A, the first end cap 3108 can be installed proximate to a heat source (not shown) such that the first end cap 3108 serves as a hot interface that vaporizes the working fluid 3122. Accordingly, the first end cap 3108 can include a material with a high thermal conductivity and/or transmissivity to absorb or deliver heat from the heat source. In the embodiment illustrated in FIG. 17A, for example, the first end cap 3108 includes the architectural construct 3112 made from a thermally conductive crystal (e.g., graphene). The architectural construct 3112 can be arranged to increase its thermal conductively by configuring the layers 3114 to have a high concentration of thermally conductive pathways (e.g., formed by the layers 3114) substantially parallel to the influx of heat. For example, in the illustrated embodiment, the layers 3114 generally align with the incoming heat flow such that heat enters the architectural construct 3112 between the layers 3114. This configuration exposes the greatest surface area of the layers 3114 to the heat and thereby increases the heat absorbed by the architectural construct 3112. Advantageously, despite having a much lower density than metal, the architectural construct 3112 can conductively and/or radiatively transfer a greater amount of heat per unit area than solid silver, raw graphite, copper, or aluminum.

As further shown in FIG. 17A, the second end cap 3110 can expel heat from the device 3100 to a heat sink (not shown) such that the second end cap 3110 serves as a cold interface that condenses the working fluid 3122. The second end cap 3110, like the first end cap 3108, can include a material with a high thermal conductivity (e.g., copper, aluminum) and/or transmissivity to absorb and/or transmit latent heat from the working fluid 3122. Accordingly, like the first end cap 3108, the second end cap 3110 can include the architectural construct 3112. However, rather than bringing heat into the device 3100 like the first end cap 3108, the second end cap 3110 can convey latent heat out of the device 3100. In various embodiments, the architectural constructs 3112 of the first and second end caps 3108 and 3110 can be made from the similar materials and/or arranged to have substantially similar thermal conductivities. In other embodiments, the architectural constructs 3112 can include different materials, can be arranged in differing directions, and/or otherwise configured to provide differing thermal conveyance capabilities including desired conductivities and transmissivities. In further embodiments, neither the first end cap 3108 nor the second end cap 3110 includes the architectural construct 3112.

In selected embodiments, the first end cap 3108 and/or the second end cap 3110 can include portions with varying thermal conductivities. For example, a portion of the first end cap 3108 proximate to the conduit 3102 can include a highly thermally conductive material (e.g., the architectural construct 3112 configured to promote thermal conductivity, copper, etc.) such that it absorbs heat from the heat source and vaporizes the working fluid 3122. Another portion of the first end cap 3108 spaced apart from the conduit 3102 can include a less thermally conductive material to insulate the high conductivity portion. In certain embodiments, for example, the insulative portion can include ceramic fibers, sealed dead air space, and/or other materials or structures with high radiant absorptivities and/or low thermal conductivities. In other embodiments, the insulative portion of the first end cap 3108 can include the architectural construct 3112 arranged to include a low concentration of thermally conductive pathways (e.g., the layers 3114 are spaced apart by large gaps 3116) such that it has a low availability for conductively transferring heat.

In other embodiments, the configurations of the architectural constructs 3112 may vary from those shown in FIG. 17A based on the dimensions of the device 3100, the temperature differential between the heat source and the heat sink, the desired heat transfer, the working fluid 3122, and/or other suitable thermal transfer characteristics. For example, architectural constructs 3112 having smaller surface areas may be suited for microscopic applications of the device 3100 and/or high temperature differentials, whereas architectural constructs 3112 having higher surface areas may be better suited for macroscopic applications of the device 3100 and/or higher rates of heat transfer. The thermal conductivities of the architectural constructs 3112 can also be altered by coating the layers 3114 with dark colored coatings to increase heat absorption and with light colored coatings to reflect heat away and thereby decrease heat absorption.

Referring still to FIG. 17A, the device 3100 can return the liquid phase 3122b of the working fluid 3122 to the input portion 3104 by capillary action. The sidewall 3120 of the conduit 3102 can thus include a wick structure that exerts a capillary pressure on the liquid phase 3122b to drive it toward a desired location (e.g., the input portion 3104). For example, the sidewall 3120 can include cellulose, ceramic wicking materials, sintered or glued metal powder, nanofibers, and/or other suitable wick structures or materials that provide capillary action.

In the embodiment shown in FIG. 17A, the architectural construct 3112 is aligned with the longitudinal axis 3118 of the conduit 3102 and configured to exert the necessary capillary pressure to direct the liquid phase 3122b of the working fluid 3122 to the input portion 3104. The composition, dopants, spacing, and/or thicknesses of the layers 3114 can be selected based on the surface tension required to provide capillary action for the working fluid 3122. Advantageously, the architectural construct 3112 can apply sufficient capillary pressure on the liquid phase 3122b to drive the working fluid 3122 short and long distances (e.g., millimeters to kilometers). Additionally, in selected embodiments, the surface tension of the layers 3114 can be manipulated such that the architectural construct 3112 rejects a preselected fluid. For example, the architectural construct 3112 can be configured to have a surface tension that rejects any liquid other than the liquid phase 3122b of the working fluid 3122. In such an embodiment, the architectural construct 3112 can function as a filter that prevents any fluid other than the working fluid 3122 (e.g., fluids tainted by impurities that diffused into the conduit 3102) from interfering with the vaporization-condensation cycle.

In other embodiments, the selective capillary action of the architectural construct 3112 separates substances at far lower temperatures than conventional distillation technologies. The faster separation of substances by the architectural construct 3112 can reduce or eliminates substance degradation caused if the substance reaches higher temperatures within the device 3100. For example, a potentially harmful substance can be removed from the working fluid 3122 by the selective capillary action of the architectural construct 3112 before the working fluid 3122 reaches the higher temperatures proximate to the input portion 3104.

The conduit 3102 and the first and second end caps 3108 and 3110 can be sealed together using suitable fasteners able to withstand the temperature differentials of the device 3100. In other embodiments, the device 3100 is formed integrally. For example, the device 3100 can be molded using one or more materials. A vacuum can be used to remove any air within the conduit 3102, and then the conduit 3102 can be filled with a small volume of the working fluid 3122 chosen to match the operating temperatures.

In operation, the device 3100 utilizes a vaporization-condensation cycle of the working fluid 3122 to transfer heat. More specifically, the first end cap 3108 can absorb heat from the heat source, and the working fluid 3122 can in turn absorb the heat from the first end cap 3108 to produce the vapor phase 3122a. The pressure differential caused by the phase change of the working fluid 3122 can drive the vapor phase 3122a of the working fluid 3122 to fill the space available and thus deliver the working fluid 3122 through the conduit 3102 to the output portion 3104. At the output portion 3104, the second end cap 3110 can absorb heat from the working fluid 3122 to change the working fluid 3122 to the liquid phase 3122b. The latent heat from the condensation of the working fluid 3122 can be transferred out of the device 3100 via the second end cap 3110. In general, the heat influx to the first end cap 3108 substantially equals the heat removed by the second end cap 3110. As further shown in FIG. 17A, capillary action provided by the architectural construct 3112 or other wick structure can return the liquid phase 3122b of the working fluid 3122 to the input portion 3104. In selected embodiments, the termini of the layers 3114 can be staggered or angled toward the conduit 3102 to facilitate entry of the liquid phase 3122b between the layers 3114 and/or to facilitate conversion of the liquid phase 3122b to the vapor phase 3122b at the input portion 3104. At the input portion 3104, the working fluid 3122 can again vaporize and continue to circulate through the conduit 3102 by means of the vaporization-condensation cycle.

The device 3100 can also operate the vaporization-condensation cycle described above in the reverse direction. For example, when the heat source and heat sink are reversed, the first end cap 3108 can serve as the cold interface and the second end cap 3110 can serve as the hot interface. Accordingly, the input and output portions 3104 and 3106 are inverted such that the working fluid 3122 vaporizes proximate to the second end cap 3110, condenses proximate to the first end cap 3108, and returns to the second end cap 3110 using the capillary action provided by the sidewall 3120. The reversibility of the device 3100 allows the device 3100 to be installed irrespective of the positions of the heat source and heat sink. Additionally, the device 3100 can accommodate environments in which the locations of the heat source and the heat sink may reverse. For example, as described further below, the device 3100 can operate in one direction during the summer to utilize solar energy and the device 3100 can reverse direction during the winter to utilize heat stored during the previous summer.

Embodiments of the device 3100 including the architectural construct 3112 at the first end cap 3108 and/or second end cap 3110 have higher thermal conductivity per unit area than conventional conductors. This increased thermal conductivity can increase process rate and the temperature differential between the first and second end caps 3108 and 3110 to produce greater and more efficient heat transfer. Additionally, embodiments including the architectural construct 3112 at the first and/or second end caps 3108 and 3110 require less surface area to absorb the heat necessary to effectuate the vaporization-condensation cycle. Thus, the device 3100 can be more compact than a conventional heat pipe that transfers an equivalent amount of heat and provide considerable cost reduction.

Referring still to FIG. 17A, in various embodiments, the device 3100 can further include a liquid reservoir 3124 in fluid communication with the conduit 3102 such that the liquid reservoir 3124 can collect and store at least a portion of the working fluid 3122. As shown in FIG. 17A, the liquid reservoir 3124 can be coupled to the input portion 3104 of the conduit 3102 via a pipe or other suitable tubular shaped structure. The liquid phase 3122b can thus flow from the sidewall 3102 (e.g., the architectural construct 3112, wick structure, etc.) into the liquid reservoir 3124. In other embodiments, the liquid reservoir 3124 is in fluid communication with another portion of the conduit 3102 (e.g., the output portion 3106) such that the liquid reservoir 3124 collects the working fluid 3122 in the vapor phase 3122a or in mixed phases.

The liquid reservoir 3124 allows the device 3100 to operate in at least two modes: a heat accumulation mode and a heat transfer mode. During the heat accumulation mode, the vaporization-condensation cycle of the working fluid 3122 can be slowed or halted by funneling the working fluid 3122 from the conduit 3102 to the liquid reservoir 3124. The first end cap 3108 can then function as a thermal accumulator that absorbs heat without the vaporization-condensation cycle dissipating the accumulated heat. After the first end cap 3108 accumulates a desired amount of heat and/or the heat source (e.g., the sun) no longer supplies heat, the device 3100 can change to the heat transfer mode by funneling the working fluid 3122 into the conduit 3102. The heat stored in first end cap 3108 can vaporize the incoming working fluid 3122 and the pressure differential can drive the vapor phase 3122a toward the output portion 3106 of the conduit 3102 to restart the vaporization-condensation cycle described above. In certain embodiments, the restart of the vaporization-condensation cycle can be monitored to analyze characteristics (e.g., composition, vapor pressure, latent heat, efficiency) of the working fluid 3122.

As shown in FIG. 17A, a controller 3126 can be operably coupled to the liquid reservoir 3124 to modulate the rate at which the working fluid 3122 enters the conduit 3102 and/or adjust the volume of the working fluid 3122 flowing into or out of the conduit 3102. The controller 3126 can thereby change the pressure within the conduit 3102 such that the device 3100 can operate at varying temperature differentials between the heat source and sink. Thus, the device 3100 can provide a constant heat flux despite a degrading heat source (e.g., first end cap 3108) or intermittent vaporization-condensation cycles.

FIGS. 17B and 17C are schematic cross-sectional views of thermal transfer devices 3200a, 3200b ("devices 3200") in accordance with other embodiments of the present technology. Several features of the devices 3200 are generally similar to the features of the device 3100 shown in FIG. 17A. For example, each device 3200 can include the conduit 3102, the sidewall 3120, and the first and second end caps 3108 and 3110. The device 3200 also transfers heat from a heat source to a heat sink utilizing a vaporization-condensation cycle of the working fluid 3122 generally similar to that described with reference to FIG. 17A. Additionally, as shown in FIGS. 17B and 17C, the device 3200 can further include the liquid reservoir 3124 and the controller 3126 such that the device 3200 can operate in the heat accumulation mode and the heat transfer mode.

The devices 3200 shown in FIGS. 17B and 17C can utilize gravity, rather than the capillary action described in FIG. 17A, to return the liquid phase 3122b of the working fluid 3122 to the input portion 3104. Thus, as shown in FIGS. 17B and 17C, the heat inflow is below the heat output such that gravity can drive the liquid phase 3122b down the sidewall 3120 to the input portion 3104. Thus, as shown in FIG. 17B, the sidewall 3120 need only include an impermeable membrane 3228, rather than a wick structure necessary for capillary action, to seal the working fluid 3122 within the conduit 3102. The impermeable membrane 3228 can be made from a polymer such as polyethylene, a metal or metal alloy such as copper and stainless steel, and/or other suitable impermeable materials. In other embodiments, the devices 3200 can utilize other sources of acceleration (e.g., centrifugal force, capillary action) to return the liquid phase 3122b to the input portion 3104 such that the positions of the input and output portions 3104 and 3106 are not gravitationally dependent.

As shown in FIG. 17C, in other embodiments, the sidewall 3120 can further include the architectural construct 3112. For example, the architectural construct 3112 can be arranged such that the layers 3114 are oriented orthogonal to the longitudinal axis 3118 of the conduit 3102 to form thermally conductive passageways that transfer heat away from the conduit 3102. Thus, as the liquid phase 3122b flows along the sidewall 3120, the architectural construct 3112 can draw heat from the liquid phase 3122b, along the layers 3114, and away from the sidewall 3120 of the device 3200. This can increase the temperature differential between the input and output portions 3104 and 3106 to increase the rate of heat transfer and/or facilitate the vaporization-condensation cycle when the temperature gradient would otherwise be insufficient. In other embodiments, the layers 3114 can be oriented at a different angle with respect to the longitudinal axis 3118 to transfer heat in a different direction. In certain embodiments, the architectural construct 3112 can be positioned radially outward of the impermeable membrane 3228. In other embodiments, the impermeable membrane 3228 can be radially outward of architectural construct 3112 or the architectural construct 3112 itself can provide a sufficiently impervious wall to seal the working fluid 3122 within the conduit 3102.

The first and second end caps 3108 and 3110 shown in FIGS. 17B and 17C can also include the architectural construct 3112. As shown in FIGS. 17B and 17C, the layers 3114 of the architectural constructs 3112 are generally aligned with the direction heat input and heat output to provide thermally conductive passageways that efficiently transfer heat. Additionally, the architectural constructs 3112 of the first and/or second end caps 3108 and 3110 can be configured to apply a capillary pressure for a particular substance entering or exiting the conduit. For example, the composition, spacing, dopants, and/or thicknesses of the layers 3114 of the architectural constructs 3112 can be modulated to selectively draw a particular substance between the layers 3114. In selected embodiments, the architectural construct 3112 can include a first zone of layers 3114 that are configured for a first substance and a second zone of layers 3114 that are configured for a second substance to selectively remove and/or add two or more desired substances from the conduit 3102.

In further embodiments, the second end cap 3110 can utilize the sorbtive properties of the architectural constructs 3112 to selectively load a desired constituent of the working fluid 3122 between the layers 3114. The construction of the architectural construct 3112 can be manipulated to obtain the requisite surface tension to load almost any element or soluble. For example, the layers 3114 can be preloaded with predetermined dopants or materials to adjust the surface tension of adsorption along these surfaces. In certain embodiments, the layers 3114 can be preloaded with $CO_2$ such that the architectural construct 3112 can selectively mine $CO_2$ from the working fluid 3122 as heat releases through the second end cap 3110. In other embodiments, the layers 3114 can be spaced apart from one another by a predetermined distance, include a certain coating, and/or otherwise be arranged to selectively load the desired constituent. In some embodiments, the desired constituent adsorbs onto the surfaces of individual layers 3114, while in other embodiments the desired constituent absorbs into zones between the layers 3114. In further embodiments, substances can be purposefully fed into the conduit 3102 from the input portion 3104 (e.g., through the first end cap 3108) such that the added substance can combine or react with the working fluid 3122 to produce the desired constituent. Thus, the architectural construct 3112 at the second end cap 3110 can facilitate selective mining of constituents. Additionally, the architectural construct 3112 can remove impurities and/or other undesirable solubles that may have entered the conduit 3102 and potentially interfere with the efficiency of the device 3200.

Similarly, in selected embodiments, the architectural construct 3112 at the first end cap 3110 can also selectively load desired compounds and/or elements to prevent them from ever entering the conduit 3102. For example, the architectural construct 3112 can filter out paraffins that can impede or otherwise interfere with the heat transfer of the device 3200. In other embodiments, the devices 3200 can include other filters that may be used to prevent certain materials from entering the conduit 3102.

Moreover, similar to selective loading of compounds and elements, the architectural construct 3112 at the first and second end caps 3108 and 3110 may also be configured to absorb radiant energy of a desired wavelength. For example, the layers 3114 can have a certain thickness, composition, spacing to absorb a particular wavelength of radiant energy. In selected embodiments, the architectural construct 3112 absorbs radiant energy of a first wavelength and converts it into radiant energy of a second wavelength, retransmitting at least some of the absorbed energy. For example, the layers 3114 may be configured to absorb ultraviolet radiation and convert the ultraviolet radiation into infrared radiation.

Additionally, the layers 3114 can also catalyze a reaction by transferring heat to a zone where the reaction is to occur. In other implementations, the layers 3114 catalyze a reaction by transferring heat away from a zone where a reaction is to occur. For example, heat may be conductively transferred into the layers 3114 (e.g., as discussed in U.S. patent application Ser. No. 12/857,515, filed Aug. 16, 2010, entitled "APPARATUSES AND METHODS FOR STORING AND/OR FILTERING A SUBSTANCE" which is incorporated by reference herein in its entirety) to supply heat to an endothermic reaction within a support tube of the layers 3114. In some implementations, the layers 3114 catalyze a reaction by removing a product of the reaction from the zone where the reaction is to occur. For example, the layers 3114 may absorb alcohol from a biochemical reaction within a central support tube in which alcohol is a byproduct, thereby expelling the alcohol on outer edges of the layers 3114, and prolonging the life of a microbe involved in the biochemical reaction.

Figure 17D:
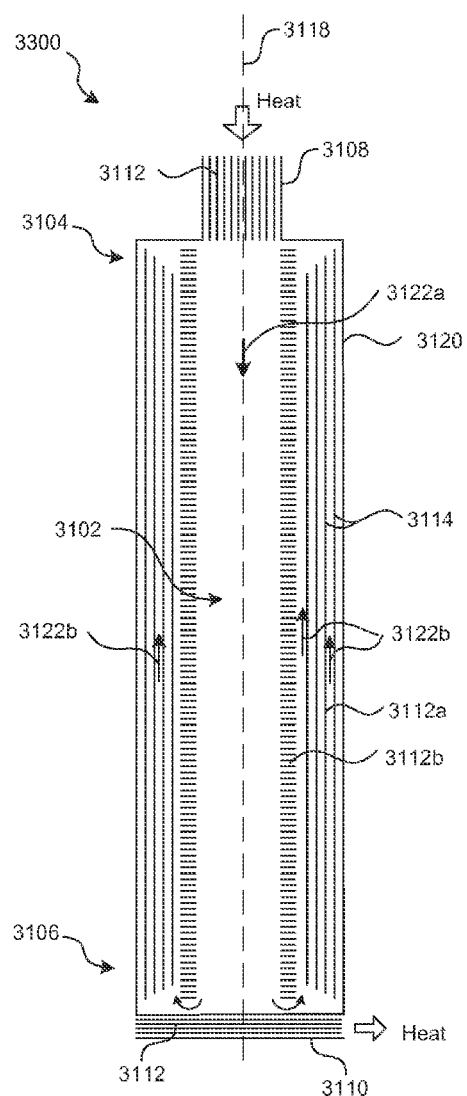
FIG. 17D is a schematic cross-sectional view of a thermal transfer device operating in a first direction in accordance with a further embodiment of the present technology.
Figure 17E:
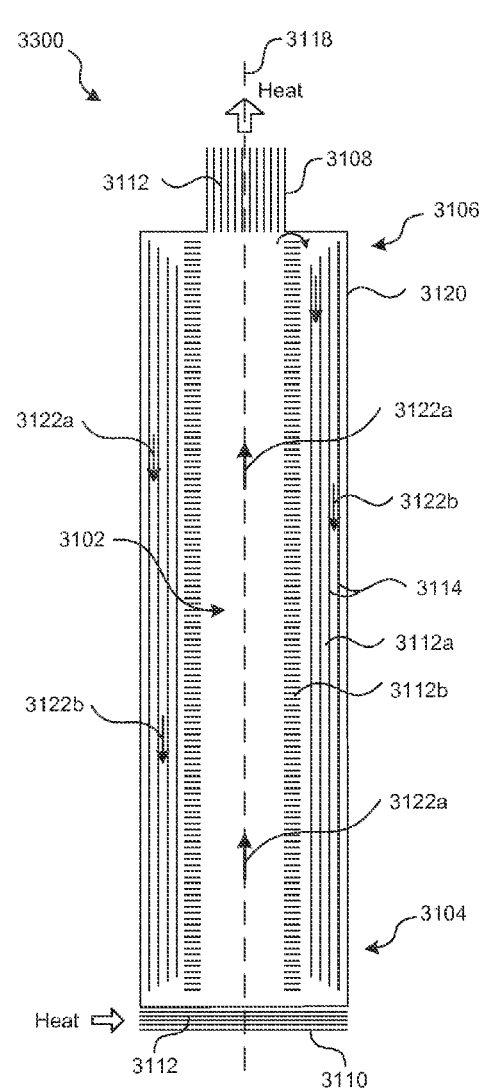
FIG. 17E is a schematic cross-sectional view of the thermal transfer device of FIG. 17D operating in a second direction opposite the first direction.

FIG. 17D is schematic cross-sectional view of a thermal transfer device 3300 ("device 3300") operating in a first direction in accordance with a further embodiment of the present technology, and FIG. 17E is a schematic cross-sectional view of the device 3300 of FIG. 17D operating in a second direction opposite the first direction. Several features of the device 3300 are generally similar to the features of the devices 3100 and 3200 shown in FIGS. 17A-17C. For example, the device 3300 can include the conduit 3102, the first and second end caps 3108 and 3110, and the architectural construct 3112. As shown in FIGS. 17D and R3-3B, the sidewall 3120 of the device 3300 can include two architectural constructs 3112: a first architectural construct 3112a having layers 3114 oriented parallel to the longitudinal axis 3118 of the conduit 3102 and a second architectural construct 3112b radially inward from the first architectural construct 3112a and having layers 3114 oriented perpendicular to the longitudinal axis 3118. The layers 3114 of the first architectural construct 3112a can perform a capillary action, and the layers 3114 of the second architectural construct 3112b can form thermally conductive passageways that transfer heat away from the side of the conduit 3102 and thereby increase the temperature differential between the input and output portions 3104 and 3106.

Similar to the device 3100 shown in FIG. 17A, the device 3300 can also operate when the direction of heat flow changes and the input and output portions 3104 and 3106 are inverted. As shown in FIG. 17D, for example, the device 3300 can absorb heat at the first end cap 3108 to vaporize the working fluid 3122 at the input portion 3104, transfer the heat via the vapor phase 3122a of the working fluid 3122 through the conduit 3102, and expel heat from the second end cap 3110 to condense the working fluid 3122 at the output portion 3106. As further shown in FIG. 17D, the liquid phase 3122b of the working fluid 3122 can move between the layers 3114 of the first architectural construct 3112b by capillary action as described above with reference to FIG. 17A. In other embodiments, the sidewall 3120 can include a different capillary structure (e.g., cellulose) that can drive the liquid phase 3122b from the output portion 3106 to the input portion 3104. As shown in FIG. R3-3B, the conditions can be reversed such that heat enters the device 3300 proximate to the second end cap 3110 and exits the device 3300 proximate to the first end cap 3108. Advantageously, as discussed above, the dual-direction vapor-condensation cycle of the working fluid 3122 accommodates environments in which the locations of the heat source and the heat sink reverse.

Figure 17F:
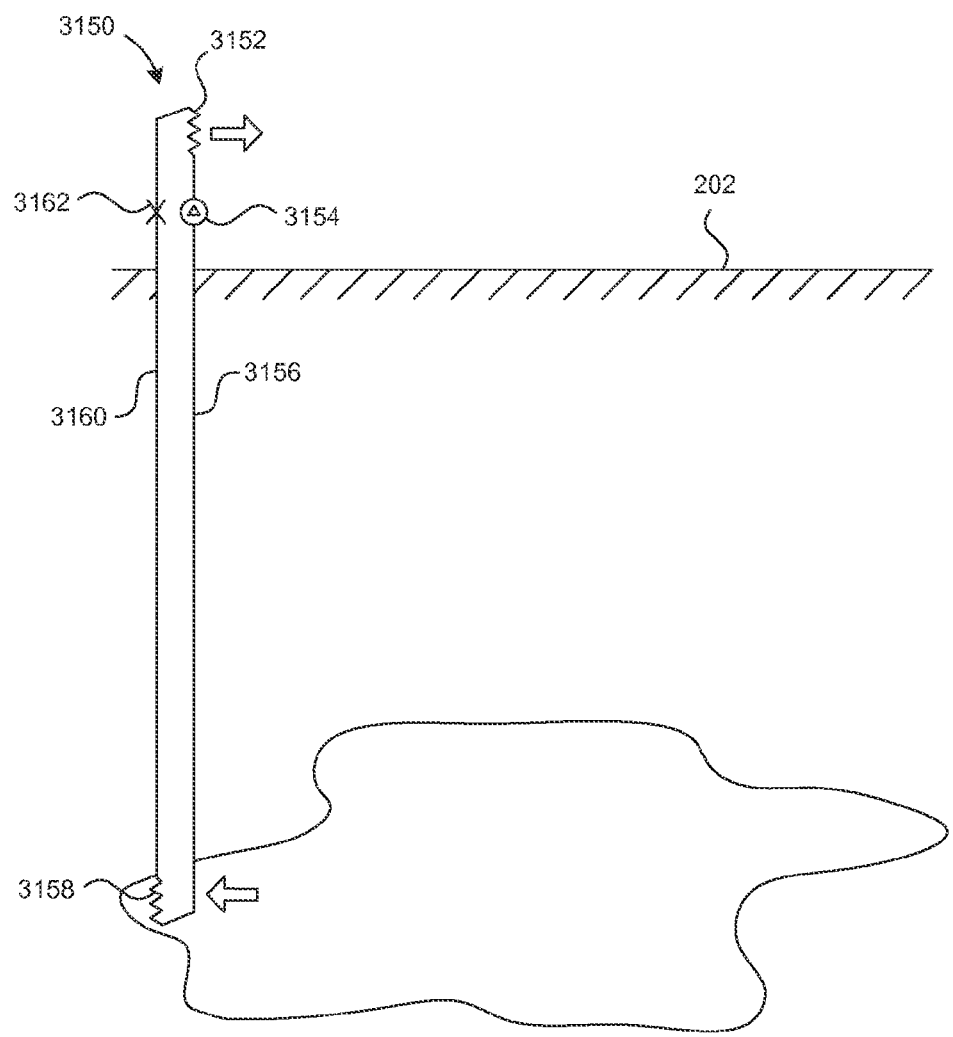
FIG. 17F is a partially schematic illustration of a heat pump suitable for transferring heat in accordance with an embodiment of the present technology.

In at least some embodiments, a heat pump can be used to transfer heat, in addition to or in lieu of a heat pipe, and the transferred heat can be used to enhance the efficiency and/or performance of a reactor to which the heat pump is coupled. In particular embodiments, the heat is extracted from a permafrost, geothermal, ocean and/or other source. FIG. 17F is a partially schematic illustration of a reversible heat pump 3150 positioned to receive heat from a source 3200 (e.g., a geothermal source), as indicated by arrow H1, and deliver the heat at a higher temperature than that of the source, as indicated by arrow H2. The heat pump 3150 transfers heat via a working fluid that can operate in a closed loop refrigeration cycle. Accordingly, the heat pump 3150 can include a compressor 3154, an expansion valve 3162, supply and return conduits 3156, 3160, and first and second heat exchangers 3152, 3158. In operation, the working fluid receives heat from the source 3200 via the second heat exchanger 3158. The working fluid passes through the supply conduit 3156 to the compressor 3154 where it is compressed, and delivers heat (e.g., to a non-combustion reactor) at the first heat exchanger 3152. The working fluid then expands through the expansion valve 3162 and returns to the second heat exchanger 3158 via the return conduit 3160.

The working fluid can be selected based at least in part on the temperature of the source 3200 and the required delivery temperature. For example, the working fluid can be a relatively inert fluid such as Freon, ammonia, or carbon dioxide. Such fluids are compatible with various polymer and metal components. These components can include tube liner polymers such as fluorinated ethylene-propylene, perfluoroalkoxy, polyvinylidene fluoride, tetrafluoroethylene, an ethylene-propylene dimer, and/or many other materials that may be reinforced with fibers such as graphite, E-glass, S-glass, glass-ceramic or various organic filaments to form the conduits 3156, 3160. The heat exchangers 3158 can be made from metal alloys, e.g., Type 304 or other "300" series austenitic stainless steels, aluminum alloys, brass or bronze selections. The compressor 3154 can be a positive displacement or turbine type compressor depending upon factors that include the scale of the application. The expansion valve 3162 can be selected to meet the pressure drop and flow requirements of a particular application.

In a representative embodiment for which the source 3200 is at a moderate temperature (e.g., 125° F. (52° C.)), the working fluid can include carbon dioxide that is expanded through the valve 3162 to a reduced temperature (e.g., 115° F. (46° C.)). The working fluid receives heat at the source 3200 to achieve a representative temperature of 120° F. (49° C.). At the compressor 3154, the temperature of the working fluid is elevated to a representative value of 325° F. (163° C.) or higher. In particular embodiments, one or more additional heat pump cycles (not shown) can be used to further elevate the delivery temperature. It can be particularly advantageous to use heat pump cycles to deliver heat at a higher temperature than the source 3200 because such cycles typically deliver two to ten times more heat energy compared to the energy required for operation of the compressor 3154.

In a generally similar manner, it can be advantageous to use one or more heat pump cycles in reverse to cool a working fluid to a temperature below the ambient temperature and thus "refrigerate" the substance being cooled. For example, permafrost or methane hydrates in lake bottoms or ocean deposits can be cooled to a temperature far below the ambient temperature of the air or surrounding water in such applications.

Still further embodiments of suitable reactors with transmissive surfaces are disclosed in pending U.S. application Ser. No. 13/027,244, filed Feb. 14, 2011, and incorporated herein by reference.

4.4 Representative Reactors with Solar Conveyors

Figure 18A:
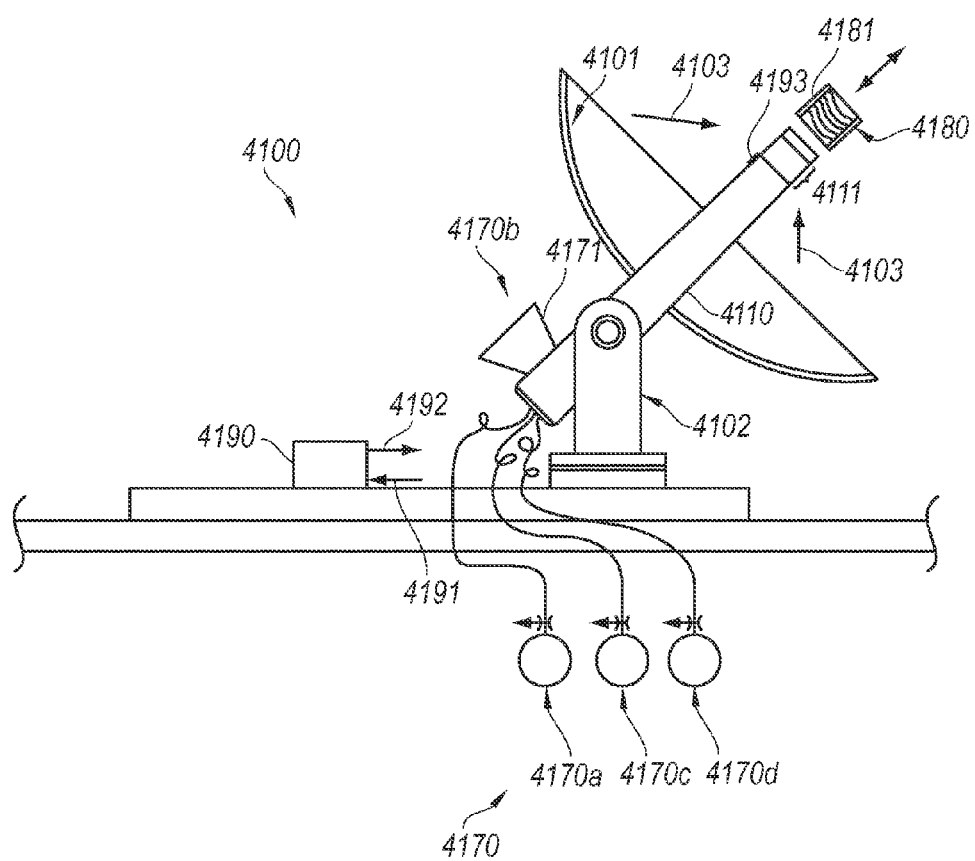
FIG. 18A is a partially schematic illustration of a system having a solar concentrator that directs heat to a reactor vessel in accordance with an embodiment of the disclosed technology.

FIG. 18A is a partially schematic illustration of a system 4100 including a reactor vessel 4110 having a reaction zone 4111. The system 4100 further includes a solar collector 4101 that directs solar energy 4103 to the reaction zone 4111. The solar collector 4103 can include a dish, trough, heliostat arrangement, fresnel lens and/or other radiation-focusing element. The reactor vessel 4110 and the solar collector 4101 can be mounted to a pedestal 4102 that allows the solar collector 4101 to rotate about at least two orthogonal axes in order to continue efficiently focusing the solar energy 4103 as the earth rotates. The system 4100 can further include multiple reactant/product vessels 4170, including first and second reactant vessels 4170a, 4170b, and first and second product vessels, 4170c, 4170d. In particular embodiments, the first reactant vessel 4170a can provide a reactant that contains hydrogen and carbon, such as methane, which is processed at the reaction zone 4111 in an endothermic reaction to produce hydrogen and carbon which is provided to the first and second product vessels 4170c, 4170d, respectively. In other embodiments, other reactants, for example, municipal solid waste streams, biomass reactants, and/or other waste streams can be provided at a hopper 4171 forming a portion of the second reactant vessel 4170b. In any of these embodiments, an internal reactant delivery system and product removal system provide the reactants to the reaction zone 4111 and remove the products from the reaction zone 4111, as will be described in further detail later with reference to FIG. 18C.

The system 4100 can further include a supplemental heat source 4180 that provides heat to the reaction zone 4111 when the available solar energy 4103 is insufficient to sustain the endothermic reaction at the reaction zone 4111. In a particular embodiment, the supplemental heat source 4180 can include an inductive heater 4181 that is positioned away from the reaction zone 4111 during the day to allow the concentrated solar energy 4103 to enter the reaction zone 4111, and can slide over the reaction zone 4111 at night to provide heat to the reaction zone 4111. The inductive heater 4181 can be powered by a renewable clean energy source, for example, hydrogen produced by the reactor vessel 4110 during the day, or falling water, geothermal energy, wind energy, or other suitable sources.

In any of the foregoing embodiments, the system 4100 can further include a controller 4190 that receives input signals 4191 and directs the operation of the devices making up the system 4100 via control signals or other outputs 4192. For example, the controller 4190 can receive a signal from a radiation sensor 4193 indicating when the incident solar radiation is insufficient to sustain the reaction at the reaction zone 4111. In response, the controller 4190 can issue a command to activate the supplemental heat source 4180. The controller 4190 can also direct the reactant delivery and product removal systems, described further below with reference to FIG. 18C.

Figure 18B:
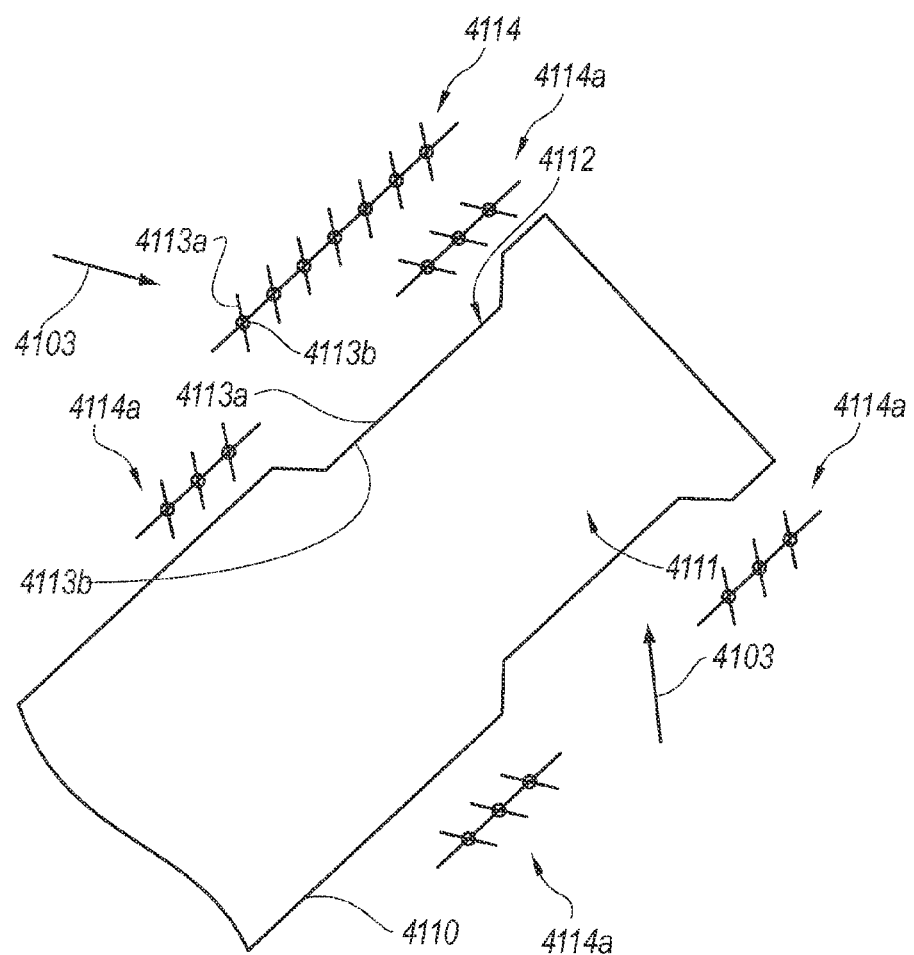
FIG. 18B is a partially schematic, enlarged illustration of a portion of a reactor vessel, including additional features for controlling the delivery of solar energy to the reaction zone in accordance with an embodiment of the disclosed technology.

FIG. 18B is a partially schematic illustration of an embodiment of the reactor vessel 4110 shown in FIG. 18A, illustrating a transmissive component 4112 positioned to allow the incident solar energy 4103 to enter the reaction zone 4111. In a particular embodiment, the transmissive component 4112 can include a glass or other suitably transparent, high temperature material that is easily transmissible to solar radiation, and configured to withstand the high temperatures in the reaction zone 4111. For example, temperatures at the reaction zone 4111 are in some embodiments expected to reach 44000° F., and can be higher for the reactants and/or products.

In other embodiments, the transmissive component 4112 can include one or more elements that absorb radiation at one wavelength and re-radiate it at another. For example, the transmissive component 4112 can include a first surface 4113a that receives incident solar energy at one wavelength and a second surface 4113b that re-radiates the energy at another wavelength into the reaction zone 4111. In this manner, the energy provided to the reaction zone 4111 can be specifically tailored to match or approximate the absorption characteristics of the reactants and/or products placed within the reaction zone 4111. Further details of representative re-radiation devices were described above in Section 4.2.

In other embodiments, the reactor vessel 4110 can include other structures that perform related functions. For example, the reactor vessel 4110 can include a Venetian blind arrangement 4114 having first and second surfaces 4113a, 4113b that can be pivoted to present one surface or the other depending upon external conditions, e.g., the level of incident solar energy 4103. In a particular aspect of this embodiment, the first surface 4113a can have a relatively high absorptivity and a relatively low emissivity. This surface can accordingly readily absorb radiation during the day. The second surface 4113b can have a relatively low absorptivity and a relatively high emissivity and can accordingly operate to cool the reaction zone 4111 (or another component of the reactor 4110), e.g., at night. A representative application of this arrangement is a reactor that conducts both endothermic and exothermic reactions, as is described further in Section 4.8 below. Further details of other arrangements for operating the solar collector 4101 (FIG. 18A) in a cooling mode are described in Section 4.5 below.

In still further embodiments, the reactor 4110 can include features that redirect radiation that "spills" (e.g., is not precisely focused on the transmissive component 4112) due to collector surface aberrations, environmental defects, non-parallel radiation, wind and/or other disturbances or distortions. These features can include additional Venetian blinds 4114a that can be positioned and/or adjusted to redirect radiation (with or without wavelength shifting) into the reaction zone 4111.

Figure 18C:
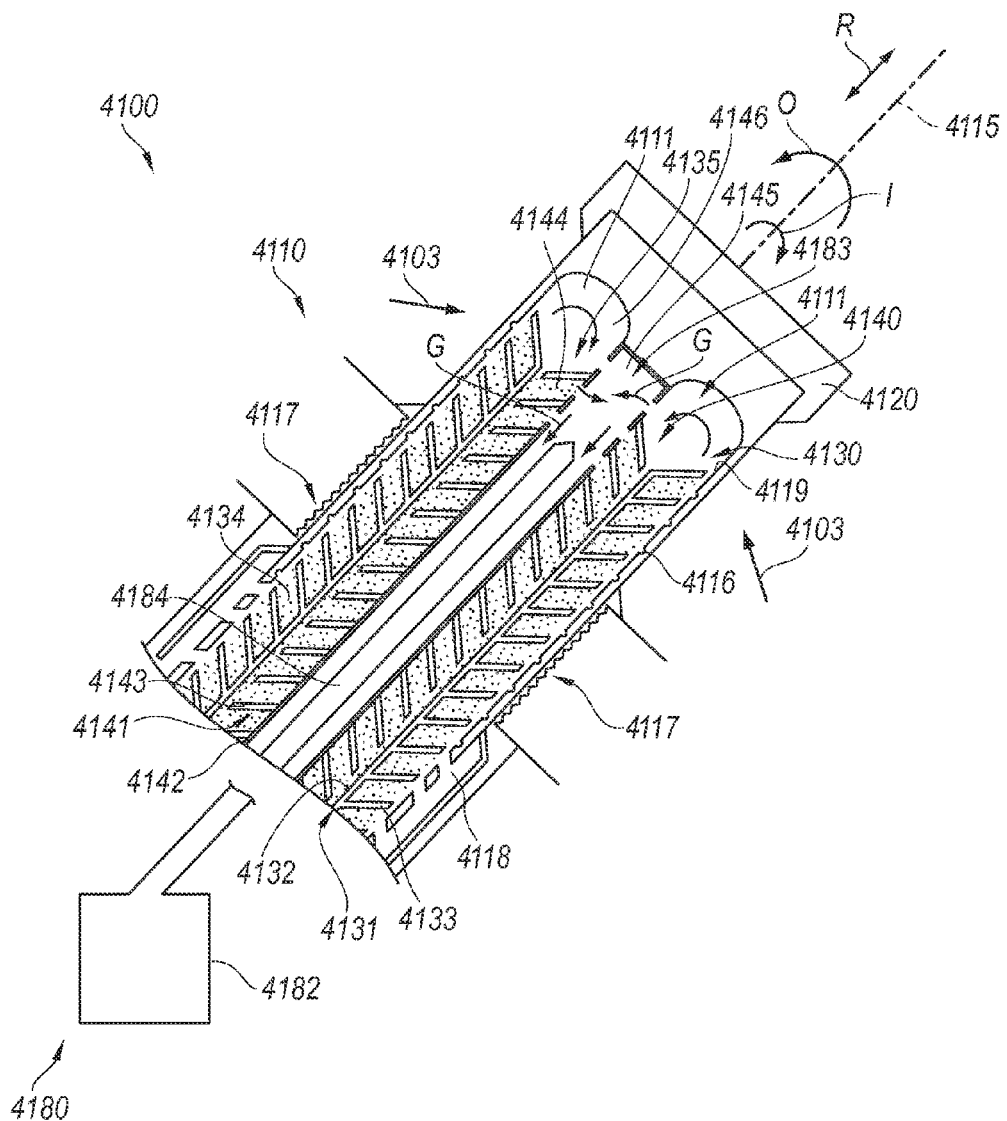
FIG. 18C is a partially schematic, cross-sectional illustration of an embodiment of a reactor vessel having annularly positioned product removal and reactant delivery systems in accordance with an embodiment of the disclosure.

FIG. 18C is a partially schematic, cross-sectional illustration of a portion of a reactor vessel 4110 configured in accordance with an embodiment of the present disclosure. In one aspect of this embodiment, the reactor 4110 includes a reactant delivery system 4130 that is positioned within a generally cylindrical, barrel-shaped reactor vessel 4110, and a product removal system 4140 positioned annularly inwardly from the reactant delivery system 4130. For example, the reactant delivery system 4130 can include an outer screw 4131, which in turn includes an outer screw shaft 4132 and outwardly extending outer screw threads 4133. The outer screw 4131 has an axially extending first axial opening 4135 in which the product removal system 4140 is positioned. The outer screw 4131 rotates about a central rotation axis 4115, as indicated by arrow O. As it does so, it carries at least one reactant 4134 (e.g., a gaseous, liquid, and/or solid reactant) upwardly and to the right as shown in FIG. 18C, toward the reaction zone 4111. As the reactant 4134 is carried within the outer screw threads 4133, it is also compacted, potentially releasing gases and/or liquids, which can escape through louvers and/or other openings 4118 located annularly outwardly from the outer screw 4131. As the reactant 4134 becomes compacted in the outer screw threads 4133, it forms a seal against an inner wall 4119 of the vessel 4110. This arrangement can prevent losing the reactant 4134, and can instead force the reactant 4134 to move toward the reaction zone 4111. The reactant delivery system 4130 can include other features, in addition to the outer screw threads 4133, to force the reactant 4134 toward the reaction zone 4111. For example, the inner wall 4119 of the reactor vessel 4110 can include one or more spiral rifle grooves 4116 that tend to force the reactant 4134 axially as the outer screw 4131 rotates. In addition to, or in lieu of this feature, the entire outer screw 4131 can reciprocate back and forth, as indicated by arrow R to prevent the reactant 4134 from sticking to the inner wall 4119, and/or to release reactant 4134 that may stick to the inner wall 4119. A barrel heater 4117 placed near the inner wall 4119 can also reduce reactant sticking, in addition to or in lieu of the foregoing features. In a least some embodiments, it is expected that the reactant 4134 will be less likely to stick when warm.

The reactant 4134 can include a variety of suitable compositions, e.g., compositions that provide a hydrogen donor to the reaction zone 4111. In representative embodiments, the reactant 4134 can include biomass constituents, e.g., municipal solid waste, commercial waste, forest product waste or slash, cellulose, lignocellulose, hydrocarbon waste (e.g., tires), and/or others. After being compacted, these waste products can be highly subdivided, meaning that they can readily absorb incident radiation due to rough surface features and/or surface features that re-reflect and ultimately absorb incident radiation. This property can further improve the efficiency with which the reactant 4134 heats up in the reaction zone 4111.

Once the reactant 4134 has been delivered to the reaction zone 4111, it receives heat from the incident solar energy 4103 or another source, and undergoes an endothermic reaction. The reaction zone 4111 can have an annular shape and can include insulation 4120 to prevent heat from escaping from the vessel 4110. In one embodiment, the endothermic reaction taking place at the reaction zone 4111 includes dissociating methane, and reforming the carbon and hydrogen constituents into elemental carbon and diatomic hydrogen, or other carbon compounds (e.g., oxygenated carbon in the form of carbon monoxide or carbon dioxide) and hydrogen compounds. The resulting product 4146 can include gaseous portions (indicated by arrow G), which passed annularly inwardly from the reaction zone 4111 to be collected by the product removal system 4140. Solid portions 4144 (e.g., ash and/or other byproducts) of the product 4146 are also collected by the product removal system 4140.

The product removal system 4140 can include an inner screw 4141 positioned in the first axial opening 4135 within the outer screw 4131. The inner screw 4141 can include an inner screw shaft 4142 and inner screw threads 4143. The inner screw 4141 can also rotate about the rotation axis 4115, as indicated by arrow I, in the same direction as the outer screw 4131 or in the opposite direction. The inner screw 4141 includes a second axial passage 4145 having openings that allow the gaseous product G to enter. The gaseous product G travels down the second axial opening 4145 to be collected and, in at least some instances, further processed (e.g., to isolate the carbon produced in the reaction from the hydrogen produced in the reaction). In particular embodiments, the gaseous product G can exchange additional heat with the incoming reactant 4134 via an additional heat exchanger (not shown in FIG. 18C) to cool the product G and heat the reactant 4134. In other embodiments, the gaseous product G can be cooled by driving a Stirling engine or other device to generate mechanical and/or electric power. As the inner screw 4141 rotates, it carries the solid portions 4144 of the product 4146 downwardly and to the left as shown in FIG. 18C. The solid products 4144 (and the gaseous product G) can convey heat via conduction to the outer screw 4130 to heat the incoming reactant 4134, after which the solid portions 4144 can be removed for use. For example, nitrogenous and/or sulfurous products from the reaction performed at the reaction zone 4111 can be used in agricultural or industrial processes. The products and therefore the chemical and physical composition of the solid portions can depend on the characteristics of the incoming reactants, which can vary widely, e.g., from municipal solid waste to industrial waste to biomass.

As discussed above with reference to FIGS. 18A and 18B, the system 4100 can include features that direct energy (e.g., heat) into the reaction zone 4111 even when the available solar energy is insufficient to sustain the reaction. In an embodiment shown in FIG. 18C, the supplemental heat source 4180 can include combustion reactants 4182 (e.g., an oxidizer and/or a hydrogen-containing combustible material) that is directed through a delivery tube 4184 positioned in the second axial opening 4145 to a combustor or combustor zone 4183 that is in thermal communication with the reaction zone 4111. During the night or other periods of time when the incident solar energy is low, the supplemental heat source 4180 can provide additional heat to the reaction zone 4111 to sustain the endothermic reaction taking place therein.

One feature of an embodiment described above with reference to FIG. 18C is that the incoming reactant 4134 can be in close or intimate thermal communication with the solid product 4144 leaving the reaction zone. In particular, the outer screw shaft 4132 and outer screw threads 4133 can be formed from a highly thermally conductive material, so as to receive heat from the solid product 4144 carried by the inner screw 4141, and deliver the heat to the incoming reactant 4134. An advantage of this arrangement is that it is thermally efficient because it removes heat from products that would otherwise be cooled in a manner that wastes the heat, and at the same time heats the incoming reactants 4134, thus reducing the amount of heat that must be produced by the solar concentrator 4101 (FIG. 18A) and/or the supplemental heat source 4180. By improving the efficiency with which hydrogen and/or carbon or other building blocks are produced in the reactor vessel 4110, the reactor system 4100 can increase the commercial viability of the renewable reactants and energy sources used to produce the products.

Still further embodiments of suitable reactors with solar conveyors are disclosed in issued U.S. Pat. No. 8,187,549, incorporated herein by reference.

4.5 Representative Reactors with Solar Concentrators

Figure 19A:
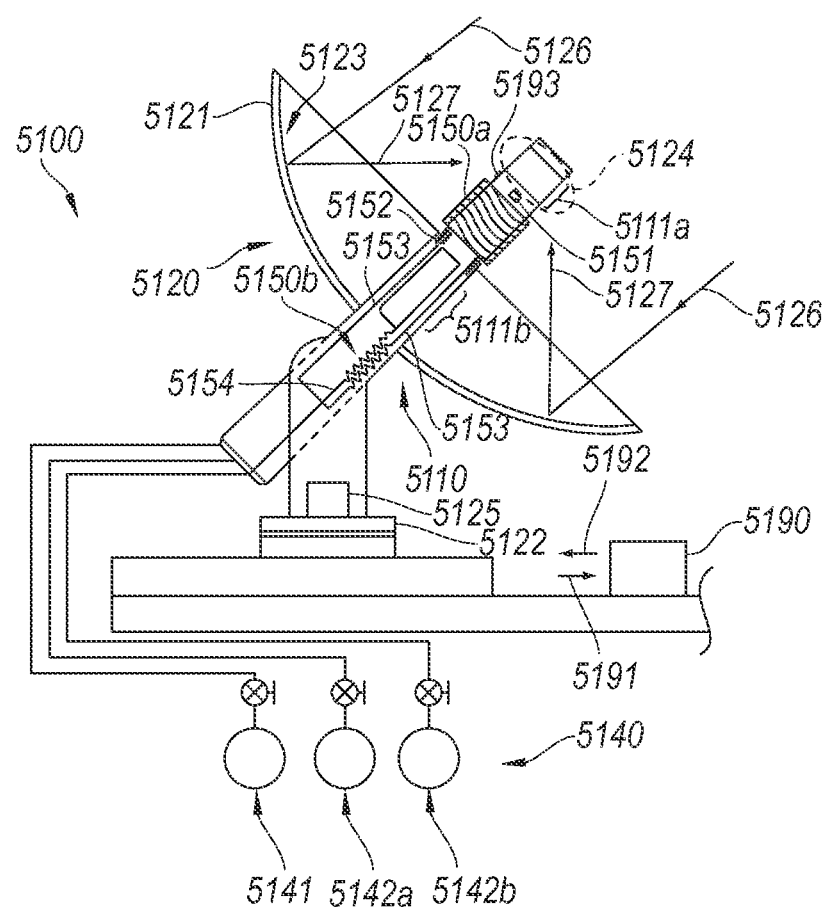
FIG. 19A is a partially schematic, partial cross-sectional illustration of a system having a solar concentrator configured in accordance with an embodiment of the present technology.

FIG. 19A is a partially schematic, partial cross-sectional illustration of a system 5100 having a reactor 5110 coupled to a solar concentrator 5120 in accordance with the particular embodiment of the technology. In one aspect of this embodiment, the solar concentrator 5120 includes a dish 5121 mounted to pedestal 5122. The dish 5121 can include a concentrator surface 5123 that receives incident solar energy 5126, and directs the solar energy as focused solar energy 5127 toward a focal area 5124. The dish 5121 can be coupled to a concentrator actuator 5125 that moves the dish 5121 about at least two orthogonal axes in order to efficiently focus the solar energy 5126 as the earth rotates. As will be described in further detail below, the concentrator actuator 5125 can also be configured to deliberately position the dish 5121 to face away from the sun during a cooling operation.

The reactor 5110 can include one or more reaction zones 5111, shown in FIG. 19A as a first reaction zone 5111a and second reaction zone 5111b. In a particular embodiment, the first reaction zone 5111a is positioned at the focal area 5124 to receive the focused solar energy 5127 and facilitate a dissociation reaction or other endothermic reaction. Accordingly, the system 5100 can further include a distribution/collection system 5140 that provides reactants to the reactor 5110 and collects products received from the reactor 5110. In one aspect of this embodiment, the distribution/collection system 5140 includes a reactant source 5141 that directs a reactant to the first reaction zone 5111a, and one or more product collectors 5142 (two are shown in FIG. 19A as a first product collector 5142a and a second product collector 5142b) that collect products from the reactor 5110. When the reactor 5110 includes a single reaction zone (e.g. the first reaction zone 5111a) the product collectors 5142a, 5142b can collect products directly from the first reaction zone 5111a. In another embodiment, intermediate products produced at the first reaction zone 5111a are directed to the second reaction zone 5111b. At the second reaction zone 5111b, the intermediate products can undergo an exothermic reaction, and the resulting products are then delivered to the product collectors 5142a, 5142b along a product flow path 5154. For example, in a representative embodiment, the reactant source 5141 can include methane and carbon dioxide, which are provided (e.g., in an individually controlled manner) to the first reaction zone 5111a and heated to produce carbon monoxide and hydrogen. The carbon monoxide and hydrogen are then provided to the second reaction zone 5111b to produce methanol in an exothermic reaction. Further details of this arrangement and associated heat transfer processes between the first reaction zone 5111a and second reaction zone 5111b are described in more detail below in Section 4.8.

In at least some instances, it is desirable to provide cooling to the reactor 5110, in addition to the solar heating described above. For example, cooling can be used to remove heat produced by the exothermic reaction being conducted at the second reaction zone 5111b and thus allow the reaction to continue. When the product produced at the second reaction zone 5111b includes methanol, it may desirable to further cool the methanol to a liquid to provide for convenient storage and transportation. Accordingly, the system 5100 can include features that facilitate using the concentrator surface 5123 to cool components or constituents at the reactor 5110. In a particular embodiment, the system 5100 includes a first heat exchanger 5150a operatively coupled to a heat exchanger actuator 5151b that moves the first heat exchanger 5150a relative to the focal area 5124. The first heat exchanger 5150a can include a heat exchanger fluid that communicates thermally with the constituents in the reactor 5110, but is in fluid isolation from these constituents to avoid contaminating the constituents and/or interfering with the reactions taking place in the reactor 5110. The heat exchanger fluid travels around a heat exchanger fluid flow path 5153 in a circuit from the first heat exchanger 5150a to a second heat exchanger 5150b and back. At the second heat exchanger 5150b, the heat exchanger fluid receives heat from the product (e.g. methanol) produced by the reactor 5110 as the product proceeds from the second reaction zone 5111b to the distribution/collection system 5140. The heat exchanger fluid flow path 5153 delivers the heated heat exchanger fluid back to the first heat exchanger 5150a for cooling. One or more strain relief features 5152 in the heat exchanger fluid flow path 5153 (e.g., coiled conduits) facilitate the movement of the first heat exchanger 5150a. The system 5100 can also include a controller 5190 that receives input signals 5191 from any of a variety of sensors, transducers, and/or other elements of the system 5100, and, in response to information received from these elements, delivers control signals 5192 to adjust operational parameters of the system 5100.

Figure 19B:
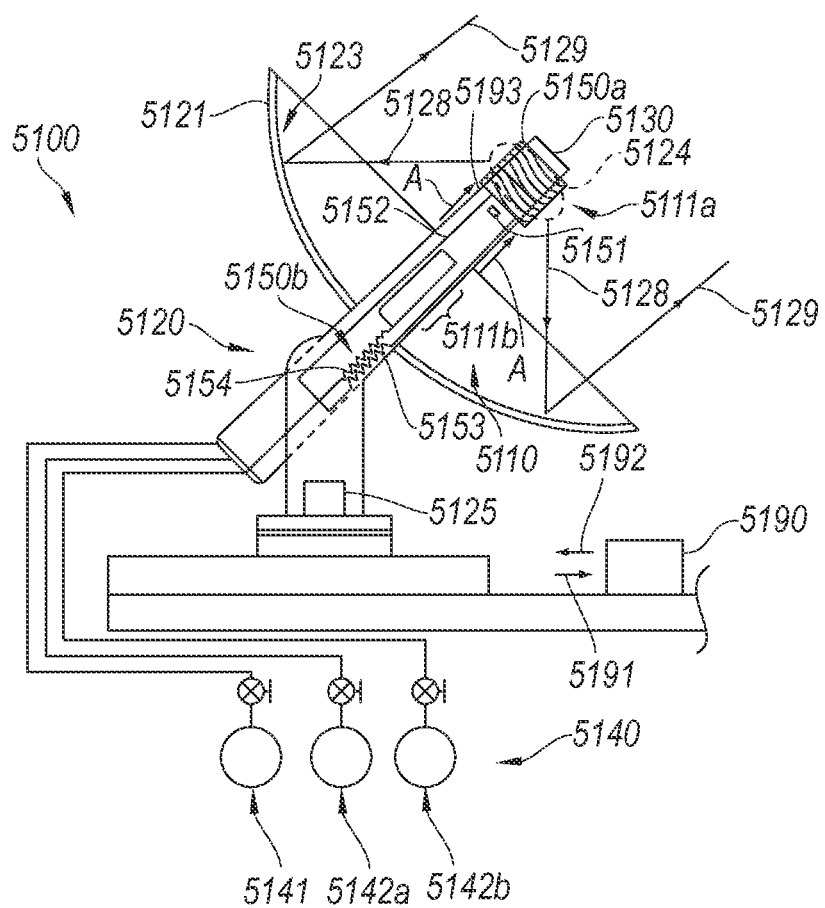
FIG. 19B is a partially schematic, partial cross-sectional illustration of an embodiment of the system shown in FIG. 1 with the solar concentrator configured to emit energy in a cooling process, in accordance with an embodiment of the disclosure.

FIG. 19B illustrates one mechanism by which the heat exchanger fluid provided to the first heat exchanger 5150a is cooled. In this embodiment, the controller 5190 directs the heat exchanger actuator 5151 to drive the first heat exchanger 5150a from the position shown in FIG. 19A to the focal area 5124, as indicated by arrows A. In addition, the controller 5190 can direct the concentrator actuator 5125 to position the dish 5121 so that the concentrator surface 5123 points away from the sun and to an area of the sky having very little radiant energy. In general, this process can be completed at night, when it is easier to avoid the radiant energy of the sun and the local environment, but in at least some embodiments, this process can be conducted during the daytime as well. A radiant energy sensor 5193 coupled to the controller 5190 can detect when the incoming solar radiation passes below a threshold level, indicating a suitable time for positioning the first heat exchanger 5150a in the location shown in FIG. 19B.

With the first heat exchanger 5150a in the position shown in FIG. 19B, the hot heat transfer fluid in the heat exchanger 5150a radiates emitted energy 5128 that is collected by the dish 5121 at the concentrator surface 5123 and redirected outwardly as directed emitted energy 5129. An insulator 5130 positioned adjacent to the focal area 5124 can prevent the radiant energy from being emitted in direction other than toward the concentrator surface 5123. By positioning the concentrator surface 5123 to point to a region in space having very little radiative energy, the region in space can operate as a heat sink, and can accordingly receive the directed emitted energy 5129 rejected by the first heat exchanger 5150a. The heat exchanger fluid, after being cooled at the first heat exchanger 5150a returns to the second heat exchanger 5150b to absorb more heat from the product flowing along the product flow path 5154. Accordingly, the concentrator surface 5123 can be used to cool as well as to heat elements of the reactor 5110.

In a particular embodiment, the first heat exchanger 5150a is positioned as shown in FIG. 19A during the day, and as positioned as shown in FIG. 19B during the night. In other embodiments, multiple systems 5100 can be coupled together, some with the corresponding first heat exchanger 5150a positioned as shown in FIG. 19A, and others with the first heat exchanger 5150a positioned as shown in FIG. 19B, to provide simultaneous heating and cooling. In any of these embodiments, the cooling process can be used to liquefy methanol, and/or provide other functions. Such functions can include liquefying or solidifying other substances, e.g., carbon dioxide, ethanol, butanol or hydrogen.

In particular embodiments, the reactants delivered to the reactor 5110 are selected to include hydrogen, which is dissociated from the other elements of the reactant (e.g. carbon, nitrogen, boron, silicon, a transition metal, and/or sulfur) to produce a hydrogen-based fuel (e.g. diatomic hydrogen) and a structural building block that can be further processed to produce durable goods. Such durable goods include graphite, graphene, and/or polymers, which may be produced from carbon structural building blocks, and other suitable compounds formed from hydrogenous or other structural building blocks. Further details of suitable processes and products are disclosed in the following co-pending U.S. patent application Ser. No. 13/027,208 titled "CHEMICAL PROCESSES AND REACTORS FOR EFFICIENTLY PRODUCING HYDROGEN FUELS AND STRUCTURAL MATERIALS, AND ASSOCIATED SYSTEMS AND METHODS"; Ser. No. 13/027,214 titled "ARCHITECTURAL CONSTRUCT HAVING FOR EXAMPLE A PLURALITY OF ARCHITECTURAL CRYSTALS"; and Ser. No. 12/027,068 titled "CARBON-BASED DURABLE GOODS AND RENEWABLE FUEL FROM BIOMASS WASTE DISSOCIATION", all of which were filed Feb. 14, 2011 and are incorporated herein by reference.

Figure 19C:
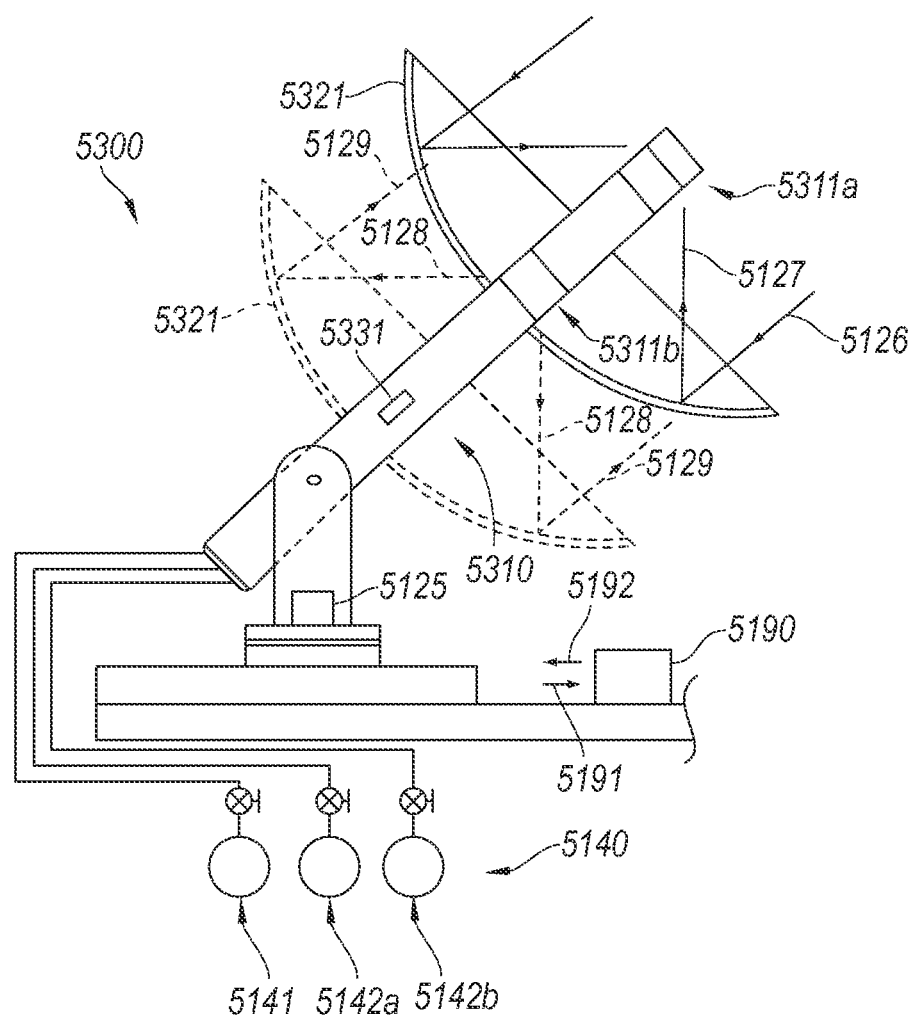
FIG. 19C is a partially schematic, partial cross-sectional illustration of a system having a movable solar concentrator dish in accordance with an embodiment of the disclosure.

FIG. 19C illustrates a system 5300 having a reactor 5310 with a movable dish 5321 configured in accordance another embodiment of the disclosed technology. In a particular aspect of this embodiment, the reactor 5310 includes a first reaction zone 5311a and a second reaction zone 5311b, with the first reaction zone 5311a receiving focused solar energy 5127 when the dish 5321 has a first position, shown in solid lines in FIG. 19C. The dish 5321 is coupled to a dish actuator 5331 that moves the dish 5321 relative to the reaction zones 5311a, 5311b. Accordingly, during a second phase of operation, the controller 5190 directs the dish actuator 5331 to move the dish 5321 to the second position shown in dashed lines in FIG. 19C. In one embodiment, this arrangement can be used to provide heat to the second reaction zone 5311b when the dish 5321 is in the second position. In another embodiment, this arrangement can be used to cool the second reaction zone 5311b. Accordingly, the controller 5190 can direct the concentrator actuator 5125 to point the dish 5321 to a position in the sky having little or no radiant energy, thus allowing the second reaction zone 5311b to reject heat to the dish 5321 and ultimately to space, in a manner generally similar to that described above with reference to FIGS. 19A and 19B.

Still further embodiments of suitable reactors with solar concentrators are disclosed in issued U.S. Pat. No. 8,187,550, incorporated herein by reference.

4.6 Representative Reactors with Induction Heating

Figure 20:
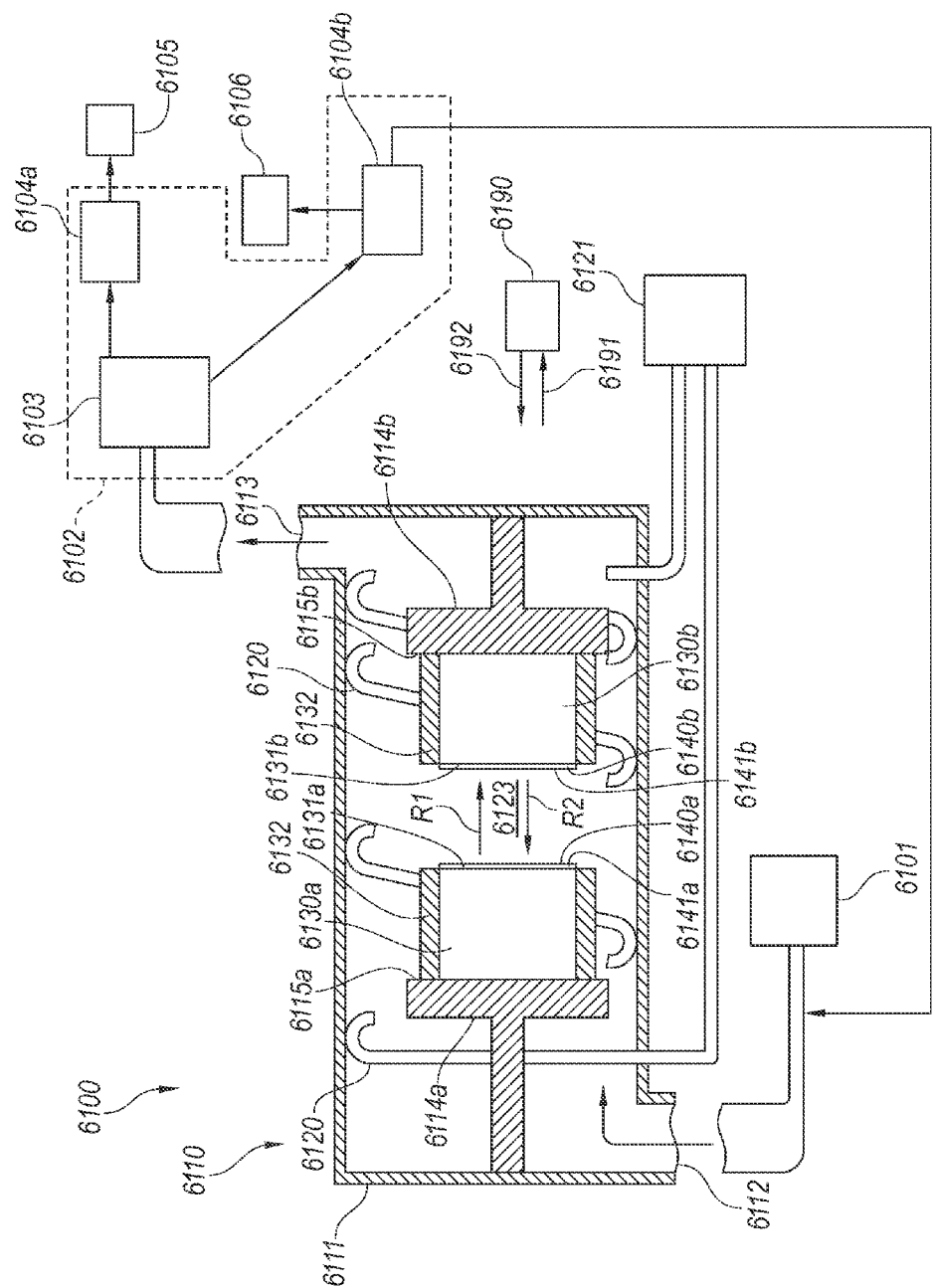
FIG. 20 is a partially schematic illustration of a system having a reactor with facing substrates for operation in a batch mode in accordance with an embodiment of the presently disclosed technology.

FIG. 20 is a partially schematic, partial cross-sectional illustration of a system 6100 having a reactor 6110 configured in accordance with an embodiment of the presently disclosed technology. In one aspect of this embodiment, the reactor 6110 includes a reactor vessel 6111 having a reaction or induction zone 6123 which is heated by an induction coil 6120. The induction coil 6120 can be a liquid-cooled, high frequency alternating current coil coupled to a suitable electrical power source 6121. The reactor vessel 6111 can further include an entrance port 6112 coupled to a precursor gas source 6101 to receive a suitable precursor gas, and an exit port 6113 positioned to remove spent gas and/or other constituents from the vessel 6111. In a particular embodiment, the precursor gas source 6101 carries a hydrocarbon gas (e.g., methane), which is dissociated into carbon and hydrogen at the induction zone 6123. The carbon is then deposited on a substrate to form a product, as is described further below, and the hydrogen and/or other constituents are removed for further processing, as is also described further below.

The reaction vessel 6111 houses a first support 6114a having a first support surface 6115a, and a second support 6114b having a second support surface 6115b facing toward the first support surface 6115a. Each support 6114a, 6114b can carry a substrate upon which one or more constituents of the precursor gas are deposited. For example, the first support 6114a can carry a first substrate 6130a and the second support 6114b can carry a second substrate 6130b. In a representative embodiment in which the precursor gas is selected to deposit carbon, the first and second substances 6130a, 6130b can also include carbon, e.g., in the form of graphite or a constituent of steel. When the precursor gas includes a different deposition element (e.g., nitrogen and/or boron), the composition of the first and second substrates 6130a, 6130b can be different. Each of the substrates 6130a, 6130b can have an initially exposed surface facing the other. Accordingly, the first substrate 6130a can have an exposed first surface 6131a facing toward a second exposed surface 6131b of the second substrate 6130b. The remaining surfaces of each substrate 6130a, 6130b can be insulated to prevent or significantly restrict radiation losses from these surfaces. The supports 6114a, 6114b can insulate at least one surface of each of the substrates 6130a, 6130b. The other surfaces (other than the exposed first and second substrates 6131a, 6131b) can be protected by a corresponding insulator 6132. The insulator 6132 can be formed from a suitable high temperature ceramic or other material.

The system 6100 can further include a controller 6190 that receives input signals 6191 from any of a variety of sensors, transducers, and/or other elements of the system 6100, and in response to information received from these elements, delivers control signals 6192 to adjust operational parameters of the system 6100. These parameters can include the pressures and flow rates with which the gaseous constituents are provided to and/or removed from the reactor vessel 6111, the operation of the induction coil 6120 and associated power source 6121, and the operation of a separator 6103 (described below), among others.

In operation, the precursor gas source 6101 supplies gas to the induction zone 6123, the induction coil 6120 is activated, and the precursor gas dissociates into at least one constituent (e.g., carbon) that is deposited onto the first and second substrates 6130a, 6130b. The constituent can be deposited in an epitaxial process that preserves the crystal grain orientation of the corresponding substrate 6130a, 6130b. Accordingly, the deposited constituent can also have a crystal and/or other self-organized structure. As the constituent is deposited, it forms a first formed structure or product 6140a at the first substrate 6130a, and a second formed structure or product 6140b at the second substrate 6130b. The first and second formed structures 6140a, 6140b each have a corresponding exposed surface 6141a, 6141b facing toward the other. The structures 6140a, 6140b can have the same or different cross-sectional shapes and/or areas, and/or can have non-crystalline, single crystal or multicrystal organizations, depending upon the selected embodiment. Radiation emitted by the first exposed surface 6131a of the first substrate 6130a, and/or by the first exposed surface 6141a of the first formed structure 6140a (collectively identified by arrow R1) is received at the second exposed surface 6141b of the second formed structure 6140b, and/or the second exposed surface 6131b of the second substrate 6130b. Similarly, radiation emitted by the second exposed surface 6141b of the second formed structure 6140b and/or the second exposed surface 6131b of the second substrate 6130b (collectively identified by arrow R2) is received at the first formed structure 6140a and/or the first substrate 6130a.

As the formed structures 6140a, 6140b grow, the exit port 6113 provides an opening through which residual constituents from the dissociated precursor gas and/or non-dissociated quantities of the precursor gas can pass. These constituents are directed to a collection system 6102, which can include a separator 6103 configured to separate the constituents into two or more flow streams. For example, the separator 6103 can direct one stream of constituents to a first product collector 6104a, and a second stream of constituents to a second product collector 6104b. In a particular embodiment, the first product collector 6104a can collect pure or substantially pure hydrogen, which can be delivered to a hydrogen-based fuel cell 6105 or other device that requires hydrogen at a relatively high level of purity. The second stream of constituents directed to the second product collector 6104b can include hydrogen mixed with other elements or compounds. Such elements or compounds can include methane or another undissociated precursor gas, and/or carbon (or another element or compound targeted for deposition) that was not deposited on the first substrate 6130a or the second substrate 6130b. These constituents can be directed to an engine 6106, for example, a turbine engine or another type of internal combustion engine that can burn a mixture of hydrogen and the other constituents. The engine 6106 and/or the fuel cell 6105 can provide power for any number of devices, including the electrical power source 6121 for the inductive coil 6120. In another aspect of this embodiment, at least some of the constituents (e.g., undissociated precursor gas) received at the second collector 6104b can be directed back into the reactor 6110 via the entrance port 6112.

An advantage of the foregoing arrangement is that the radiation losses typically encountered in a chemical vapor deposition apparatus can be avoided by positioning multiple substrates in a manner that allows radiation emitted from one surface to be received by another surface that is also targeted for deposition. In a particular embodiment shown in FIG. 20, two substrates are shown, each having a single exposed surface facing the other. In other embodiments, additional substrates can be positioned (e.g., in a plane extending inwardly and/or outwardly transverse to the plane of FIG. 20) to allow additional exposed surfaces of a formed product to radiate heat to corresponding surfaces of other formed products.

Another advantage of the foregoing arrangement is that it can be used to produce a structural building block and/or an architectural construct, as well as clean burning hydrogen fuel from a hydrogen donor. When the precursor gas includes a hydrocarbon, the architectural construct can include graphene and/or another carbon-bearing material, for example, a material that can be further processed to form a carbon-based composite or a carbon-based polymer. In other embodiments, the precursor gas can include other elements (e.g., boron, nitrogen, sulfur, silicon, and/or a transition metal) than can also be used to form structural building blocks that contain the element, and/or architectural constructs formed from the building blocks. Suitable processes and representative architectural constructs are further described in the following co-pending U.S. Patent Applications, all of which were filed on Feb. 14, 2011 and are incorporated herein by reference: application Ser. No. 13/027,208; application Ser. No. 13/027,214; and application Ser. No. 13/027,068.

One feature of an embodiment described above with reference to FIG. 20 is that it may be conducted in a batch process. For example, each of the first and second formed structures 6140a, 6140b can be grown by a particular amount and then removed from the reaction vessel 6111. In other embodiments, the products can be formed in a continuous manner, without the need for halting the reaction to remove the product.

Still further embodiments of suitable reactors with induction heating are disclosed in pending U.S. application Ser. No. 13/027,215, filed Feb. 14, 2011, and incorporated herein by reference.

4.7 Representative Reactors Using Engine Heat

Figure 21:
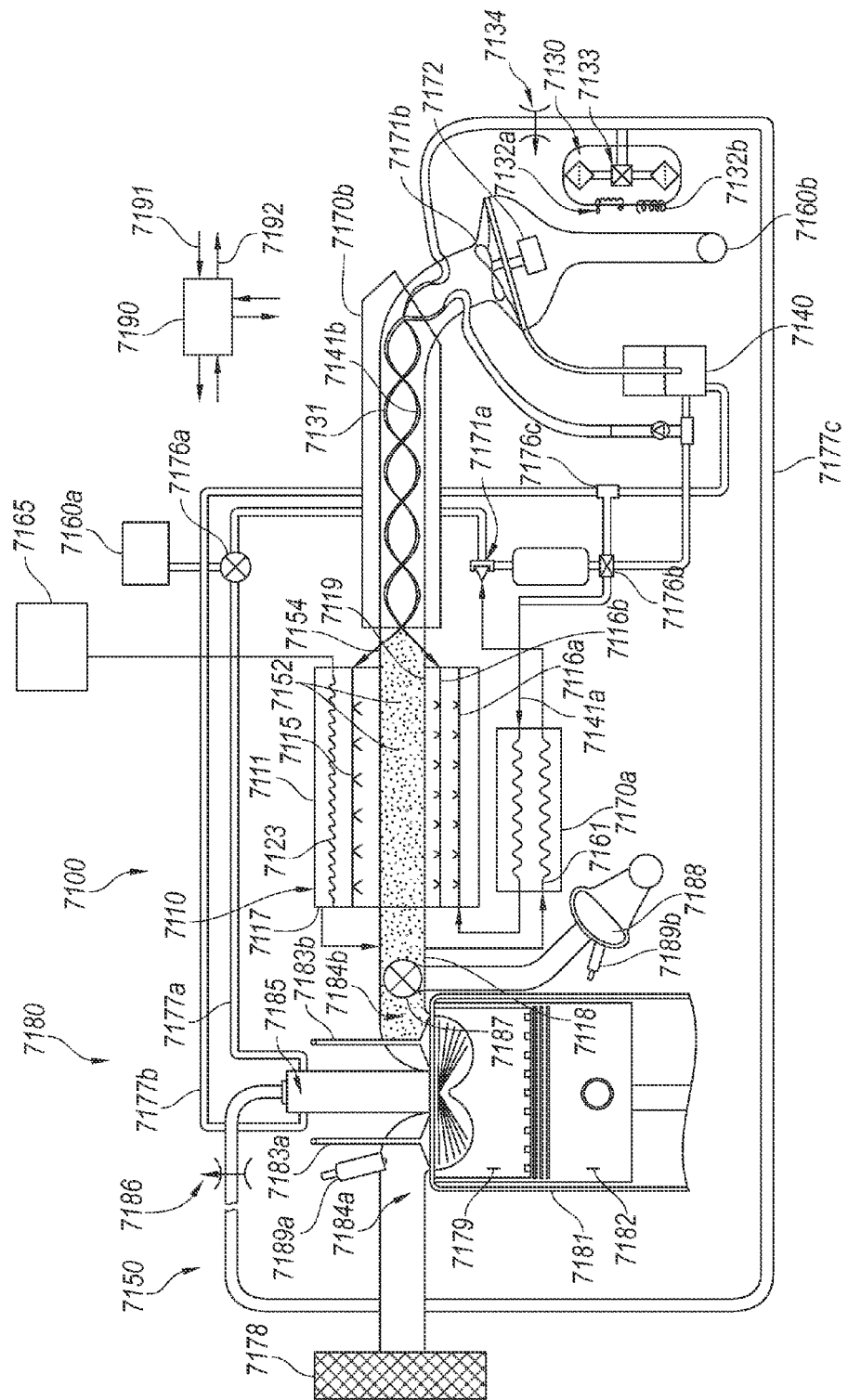
FIG. 21 is a partially schematic, partially cross-sectional illustration of a reactor system that receives energy from a combustion engine and returns reaction products to the engine in accordance with an embodiment of the presently disclosed technology.

FIG. 21 is a partially schematic illustration of system 7100 that includes a reactor 7110 in combination with a radiant energy/reactant source 7150 in accordance with another embodiment of the technology. In this embodiment, the radiant energy/reactant source 7150 includes an engine 7180, e.g., an internal combustion engine having a piston 7182 that reciprocates within a cylinder 7181. In other embodiments, the engine 7180 can have other configurations, for example, an external combustion configuration. In an embodiment shown in FIG. 21, the engine 7180 includes an intake port 7184a that is opened and closed by an intake valve 7183a to control air entering the cylinder 7181 through an air filter 7178. The air flow can be unthrottled in an embodiment shown in FIG. 21, and can be throttled in other embodiments. A fuel injector 7185 directs fuel into the combustion zone 7179 where it mixes with the air and ignites to produce the combustion products 7152. Additional fuel can be introduced by an injection valve 7189a. The combustion products 7152 exit the cylinder 7181 via an exhaust port 7184b controlled by an exhaust valve 7183b. Further details of representative engines and ignition systems are disclosed in co-pending U.S. application Ser. No. 12/653,085 filed on Dec. 7, 2010, and incorporated herein by reference.

The engine 7180 can include features specifically designed to integrate the operation of the engine with the operation of the reactor 7110. For example, the engine 7180 and the reactor 7110 can share fuel from a common fuel source 7130 which is described in further detail below. The fuel is provided to the fuel injector 7185 via a regulator 7186. The engine 7180 can also receive end products from the reactor 7110 via a first conduit or passage 7177a, and water (e.g., liquid or steam) from the reactor 7110 via a second conduit or passage 7177b. Further aspects of these features are described in greater detail below, following a description of the other features of the overall system 7100.

The system 7100 shown in FIG. 21 also includes heat exchangers and separators configured to transfer heat and segregate reaction products in accordance with the disclosed technology. In a particular aspect of this embodiment, the system 7100 includes a steam/water source 7140 that provides steam to the reactor vessel 7111 to facilitate product formation. Steam from the steam/water source 7140 can be provided to the reactor 7110 via at least two channels. The first channel includes a first water path 7141a that passes through a first heat exchanger 7170a and into the reactor vessel 7111 via a first steam distributor 7116a. Products removed from the reactor vessel 7111 pass through a reactor product exit port 7117 and along a products path 7161. The products path 7161 passes through the first heat exchanger 7170a in a counter-flow or counter-current manner to cool the products and heat the steam entering the reactor vessel 7111. The products continue to a reaction product separator 7171a that segregates useful end products (e.g., hydrogen and carbon or carbon compounds). At least some of the products are then directed back to the engine 7180, and other products are then collected at a products collector 7160a. A first valve 7176a regulates the product flow. Water remaining in the products path 7161 can be separated at the reaction product separator 7171a and returned to the steam/water source 7140.

The second channel via which the steam/water source 7140 provides steam to the reactor 7110 includes a second water path 7141b that passes through a second heat exchanger 7170b. Water proceeding along the second water path 7141b enters the reactor 7110 in the form of steam via a second stream distributor 7116b. This water is heated by combustion products that have exited the combustion zone 7179 and passed through the transfer passage 7118 (which can include a transmissive surface 7119) along a combustion products path 7154. The spent combustion products 7152 are collected at a combustion products collector 7160b and can include nitrogen compounds, phosphates, re-used illuminant additives (e.g., sources of sodium, magnesium and/or potassium), and/or other compositions that may be recycled or used for other purposes (e.g., agricultural purposes). The illuminant additives can be added to the combustion products 7152 (and/or the fuel used by the engine 7180) upstream of the reactor 7110 to increase the amount of radiant energy available for transmission into the reaction zone 7112.

In addition to heating water along the second water path 7141b and cooling the combustion products along the combustion products path 7154, the second heat exchanger 7170b can heat the hydrogen donor passing along a donor path 7131 to a donor distributor 7115 located within the reactor vessel 7111. The donor vessel 7130 houses a hydrogen donor, e.g., a hydrocarbon such as methane, or a nitrogenous donor such as ammonia. The donor vessel 7130 can include one or more heaters 7132 (shown as first heater 7132a and a second heater 7132b) to vaporize and/or pressurize the hydrogen donor within. A three-way valve 7133 and a regulator 7134 control the amount of fluid and/or vapor that exits the donor vessel 7130 and passes along the donor path 7131 through the second heat exchanger 7170b and into the reactor vessel 7111. As discussed above, the hydrogen donor can also serve as a fuel for the engine 7180, in at least some embodiments, and can be delivered to the engine 7180 via a third conduit or passage 7177c.

In the reactor vessel 7111, the combustion products 7152 pass through the combustion products passage 7118 while delivering radiant energy and/or reactants through the transmissive surface 7119 into the reaction zone 7112. After passing through the second heat exchanger 7170b, the combustion products 7152 can enter a combustion products separator 7171b that separates water from the combustion products. The water returns to the steam/water source 7140 and the remaining combustion products are collected at the combustion products collector 7160b. In a particular embodiment, the separator 7171b can include a centrifugal separator that is driven by the kinetic energy of the combustion product stream. If the kinetic energy of the combustion product stream is insufficient to separate the water by centrifugal force, a motor/generator 7172 can add energy to the separator 7171b to provide the necessary centrifugal force. If the kinetic energy of the combustion product stream is greater than is necessary to separate water, the motor/generator 7172 can produce energy, e.g., to be used by other components of the system 7100. The controller 7190 receives inputs from the various elements of the system 7100 and controls flow rates, pressures, temperatures, and/or other parameters.

The controller 7190 can also control the return of reactor products to the engine 7180. For example, the controller can direct reaction products and/or recaptured water back to the engine 7180 via a series of valves. In a particular embodiment, the controller 7190 can direct the operation of the first valve 7176a which directs hydrogen and carbon monoxide obtained from the first separator 7171a to the engine 7180 via the first conduit 7177a. These constituents can be burned in the combustion zone 7179 to provide additional power from the engine 7180. In some instances, it may be desirable to cool the combustion zone 7179 and/or other elements of the engine 7180 as shown. In such instances, the controller 7190 can control a flow of water or steam to the engine 7180 via second and third valves 7176b, 7176c and the corresponding second conduit 7177b.

In some instances, it may be desirable to balance the energy provided to the reactor 7110 with energy extracted from the engine 7180 used for other proposes. According, the system 7100 can included a proportioning valve 7187 in the combustion products stream that can direct some combustion products 7152 to a power extraction device 7188, for example, a turbo-alternator, turbocharger or a supercharger. When the power extraction device 7188 includes a supercharger, it operates to compress air entering the engine cylinder 7181 via the intake port 7184a. When the extraction device 7188 includes a turbocharger, it can include an additional fuel injection valve 7189b that directs fuel into the mixture of combustion products for further combustion to produce additional power. This power can supplement the power provided by the engine 7180, or it can be provided separately, e.g., via a separate electrical generator.

As is evident from the forgoing discussion, one feature of the system 7100 is that it is specifically configured to conserve and reuse energy from the combustion products 7152. Accordingly, the system 7100 can include additional features that are designed to reduce energy losses from the combustion products 7152. Such features can include insulation positioned around the cylinder 7181, at the head of the piston 7182, and/or at the ends of the valves 7183a, 7183b. Accordingly, the insulation prevents or at least restricts heat from being conveyed away from the engine 7180 via any thermal channel other than the passage 7118.

One feature of at least some of the foregoing embodiments is that the reactor system can include a reactor and an engine linked in an interdependent manner. In particular, the engine can provide waste heat that facilitates a dissociation process conducted at the reactor to produce a hydrogen-based fuel and a non-hydrogen based structural building block. The building block can include a molecule containing carbon, boron, nitrogen, silicon and/or sulfur, and can be used to form an architectural construct. Representative examples of architectural constructs, in addition to the polymers and composites described above are described in further detail in co-pending U.S. application Ser. No. 12/027,214, previously incorporated herein by reference. An advantage of this arrangement is that it can provide a synergy between the engine and the reactor. For example, the energy inputs normally required by the reactor to conduct the dissociation processes described above can be reduced by virtue of the additional energy provided by the combustion product. The efficiency of the engine can be improved by adding clean-burning hydrogen to the combustion chamber, and/or by providing water (e.g., in steam or liquid form) for cooling the engine. Although both the steam and the hydrogen-based fuel are produced by the reactor, they can be delivered to the engine at different rates and/or can vary in accordance with different schedules and/or otherwise in different manners.

Still further embodiments of suitable reactors with using engine heat are disclosed in pending U.S. application Ser. No. 13/027,198, filed Feb. 14, 2011, and incorporated herein by reference.

4.8 Representative Exothermic/Endothermic Reactors

Figure 22:
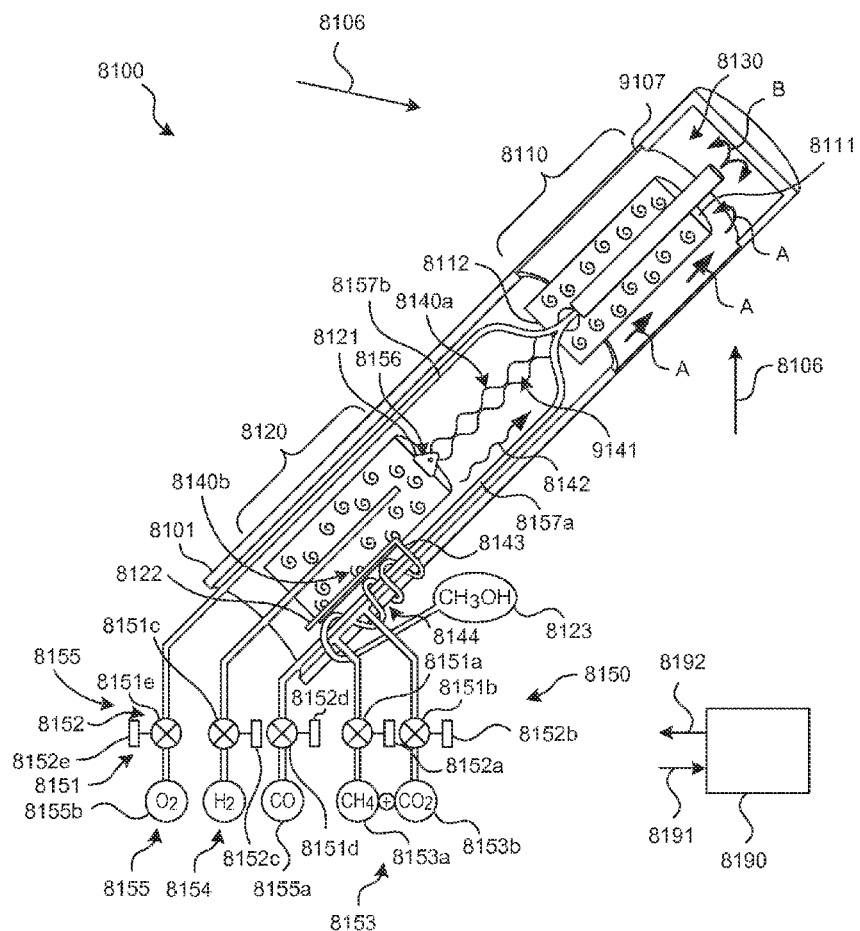
FIG. 22 is a partially schematic, cross-sectional illustration of a reactor having interacting endothermic and exothermic reaction zones in accordance with an embodiment of the disclosure.

FIG. 22 is a partially schematic, cross-sectional illustration of particular components of the system 8100, including the reactor vessel 8101. The reactor vessel 8101 includes the first reaction zone 8110 positioned toward the upper left of FIG. R8-2 (e.g., at a first reactor portion) to receive incident solar radiation 8106, e.g., through a solar transmissive surface 8107. The second reaction zone 8120 is also positioned within the reactor vessel 8101, e.g., at a second reactor portion, to receive products from the first reaction zone 8110 and to produce an end product, for example, methanol. Reactant sources 8153 provide reactants to the reactor vessel 8101, and a product collector 8123 collects the resulting end product. A regulation system 8150, which can include valves 8151 or other regulators and corresponding actuators 8152, is coupled to the reactant sources 8153 to control the delivery of reactants to the first reaction zone 8110 and to control other flows within the system 8100. In other embodiments, the valves can be replaced by or supplemented with other mechanisms, e.g., pumps.

In a particular embodiment, the reactant sources 8153 include a methane source 8153*a* and a carbon dioxide source 8153*b*. The methane source 8153*a* is coupled to a first reactant valve 8151*a* having a corresponding actuator 8152*a*, and the carbon dioxide source 8153*b* is coupled to a second reactant valve 8151*b* having a corresponding actuator 8152*b*. The reactants pass into the reaction vessel 8101 and are conducted upwardly around the second reaction zone 8120 and the first reaction zone 8110 as indicated by arrows A. As the reactants travel through the reactor vessel 8101, they can receive heat from the first and second reaction zones 8110, 8120 and from products passing from the first reaction zone 8110 to the second reaction zone 8120, as will be described in further detail later. The reactants enter the first reaction zone 8110 at a first reactant port 8111. At the first reaction zone 8110, the reactants can undergo the following reaction:

$$CH_4 + CO_2 + HEAT \rightarrow 2CO + 2H_2 \qquad \text{[Equation R8-1]}$$

In a particular embodiment, the foregoing endothermic reaction is conducted at about 900° C. and at pressures of up to about 1,500 psi. In other embodiments, reactions with other reactants can be conducted at other temperatures at the first reaction zone 8110. The first reaction zone 8110 can include any of a variety of suitable catalysts, for example, a nickel/aluminum oxide catalyst. In particular embodiments, the reactants and/or the first reaction zone 8110 can be subjected to acoustic pressure fluctuation (in addition to the overall pressure changes caused by introducing reactants, undergoing the reaction, and removing products from the first reaction zone 8110) to aid in delivering the reactants to the reaction sites of the catalyst. In any of these embodiments, the products produced at the first reaction zone 8110 (e.g. carbon monoxide and hydrogen) exit the first reaction zone 8110 at a first product port 8112 and enter a first heat exchanger 8140*a*. The first products travel through the first heat exchanger 8140*a* along a first flow path 8141 and transfer heat to the incoming reactants traveling along a second flow path 8142. Accordingly, the incoming reactants can be preheated at the first heat exchanger 8140*a*, and by virtue of passing along or around the outside of the first reaction zone 8110. In particular embodiments, one or more surfaces of the first heat exchanger 8140*a* can include elements or materials that absorb radiation at one frequency and re-radiate it at another. Further details of suitable materials and arrangements are disclosed in Section 4.2 above.

The first products enter the second reaction zone 8120 via a second reactant port 8121 and a check valve 8156 or other flow inhibitor. The check valve 8156 is configured to allow a one-way flow of the first products into the second reaction zone 8120 when the pressure of the first products exceeds the pressure in the second reaction zone 8120. In other embodiments, the check valve 8156 can be replaced with another mechanism, e.g., a piston or pump that conveys the first products to the second reaction zone 8120.

At the second reaction zone 8120, the first products from the first reaction zone 8110 undergo an exothermic reaction, for example:

$$2CO + 2H_2 + 2'H_2 \rightarrow CH_3OH + HEAT \qquad \text{[Equation R8-2]}$$

The foregoing exothermic reaction can be conducted at a temperature of approximately 250° C. and in many cases at a pressure higher than that of the endothermic reaction in the first reaction zone 8110. To increase the pressure at the second reaction zone 8120, the system 8100 can include an additional constituent source 8154 (e.g. a source of hydrogen) that is provided to the second reaction zone 8120 via a valve 8151*c* and corresponding actuator 8152*c*. The additional constituent (e.g. hydrogen, represented by 2'H$_2$ in Equation R8-2) can pressurize the second reaction zone with or without necessarily participating as a consumable in the reaction identified in Equation R8-2. In particular, the additional hydrogen may be produced at pressure levels beyond 1,500 psi, e.g., up to about 5,000 psi or more, to provide the increased pressure at the second reaction zone 8120. In a representative embodiment, the additional hydrogen may be provided in a separate dissociation reaction using methane or another reactant. For example, the hydrogen can be produced in a separate endothermic reaction, independent of the reactions at the first and second reaction zones 8110, 8120, as follows:

$$CH_4 + HEAT \rightarrow C + 2H_2 \qquad \text{[Equation R8-3]}$$

In addition to producing hydrogen for pressurizing the second reaction zone 8120, the foregoing reaction can produce carbon suitable to serve as a building block in the production of any of a variety of suitable end products, including polymers, self-organizing carbon-based structures such as graphene, carbon composites, and/or other materials. Further examples of suitable products are included in co-pending U.S. application Ser. No. 12/027,214 previously concurrently herewith and incorporated herein by reference.

The reaction at the second reaction zone 8120 can be facilitated with a suitable catalyst, for example, copper, zinc, aluminum and/or compounds including one or more of the foregoing elements. The product resulting from the reaction at the second reaction zone 8120 (e.g. methanol) is collected at the product collector 8123. Accordingly, the methanol exits the second reaction zone 8120 at a second product port 8122 and passes through a second heat exchanger 8140$b$. At the second heat exchanger 8140$b$, the methanol travels along a third flow path 8143 and transfers heat to the incoming constituents provided to the first reaction zone 8110 along a fourth flow path 8144. Accordingly, the two heat exchangers 8140$a$, 8140$b$ can increase the overall efficiency of the reactions taking place in the reactor vessel 8101 by conserving and recycling the heat generated at the first and second reaction zones.

In a particular embodiment, energy is provided to the first reaction zone 8110 via the solar concentrator 8103 described above with reference to FIG. R8-2. Accordingly, the energy provided to the first reaction zone 8110 by the solar collector 8103 will be intermittent. The system 8100 can include a supplemental energy source that allows the reactions to continue in the absence of sufficient solar energy. In particular, the system 8100 can include a supplemental heat source 8155. For example, the supplemental heat source 8155 can include a combustion reactant source 8155$a$ (e.g. providing carbon monoxide) and an oxidizer source 8155$b$ (e.g. providing oxygen). The flows from the reactant source 8155$a$ and oxidizer source 8155$b$ are controlled by corresponding valves 8151$d$, 8151$e$, and actuators 8152$d$, 8152$e$. In operation, the reactant and oxidizer are delivered to the reactor vessel 8101 via corresponding conduits 8157$a$, 8157$b$. The reactant and oxidizer can be preheated within the reactor vessel 8101, before reaching a combustion zone 8130, as indicated by arrow B. At the combustion zone 8130, the combustion reactant and oxidizer are combusted to provide heat to the first reaction zone 8110, thus supporting the endothermic reaction taking place within the first reaction zone 8110 in the absence of sufficient solar energy. The result of the combustion can also yield carbon dioxide, thus reducing the need for carbon dioxide from the carbon dioxide source 8153$b$. The controller 8190 can control when the secondary heat source 8155 is activated and deactivated, e.g., in response to a heat or light sensor.

In another embodiment, the oxygen provided by the oxidizer source 8155$b$ can react directly with the methane at the combustion zone 8130 to produce carbon dioxide and hydrogen. This in turn can also reduce the amount of carbon dioxide required at the first reaction zone 8110. Still further embodiments of suitable exothermic/endothermic reactors are disclosed in pending U.S. application Ser. No. 13/027,060, filed Feb. 14, 2011, and incorporated herein by reference.

The following U.S. non-provisional applications describe additional embodiments of thermochemical reactors and associated systems, are filed concurrently herewith, and are incorporated herein by reference:

U.S. Ser. No. 13/584,748, titled "FUEL-CELL SYSTEMS OPERABLE IN MULTIPLE MODES FOR VARIABLE PROCESSING OF FEEDSTOCK MATERIALS AND ASSOCIATED DEVICES, SYSTEMS, AND METHODS";

U.S. Ser. No. 13/584,741, titled "SYSTEM AND METHOD FOR COLLECTING AND PROCESSING PERMAFROST GASES, AND FOR COOLING PERMAFROST";

U.S. Ser. No. 13/584,688, titled "GEOTHERMAL ENERGIZATION OF A NON-COMBUSTION CHEMICAL REACTOR AND ASSOCIATED SYSTEMS AND METHODS";

U.S. Ser. No. 13/584,773, titled "SYSTEMS AND METHODS FOR PROVIDING SUPPLEMENTAL AQUEOUS THERMAL ENERGY";

U.S. Ser. No. 13/584,708, titled "SYSTEMS AND METHODS FOR EXTRACTING AND PROCESSING GASES FROM SUBMERGED SOURCES"; and U.S. Ser. No. 13/584,749, titled "MOBILE TRANSPORT PLATFORMS FOR PRODUCING HYDROGEN AND STRUCTURAL MATERIALS, AND ASSOCIATED SYSTEMS AND METHODS".

Systems in accordance with the foregoing embodiments can provide several advantages. For example, because many of the systems are powered at least in part by available kinetic energy from wind and/or braking, the conventional belt drives between the engine's crankshaft and radiator cooling fans, coolant pumps, alternators, heat pump compressors, power steering pumps, brake booster compressor/pumps and the like can be eliminated or provided as normally disengaged clutch drives. Heat normally rejected by forcing air through the radiator with a fan and turbocharger intercooling can be applied to the reactor for more productive use. In comparison with the large "radiator" requirements for frontal area and air pumping energy that must transfer the same amount of heat from the engine and/or transmission's cooling systems into air flowing through the radiator, far less frontal area, consequent wind resistance, and much less pumping energy are required to reject the waste heat from the engine's coolant to liquid fuels. In at least some embodiments, radiators (e.g., those at the fronts of tractor trailer combinations) can be eliminated entirely. Eliminating or reducing the size of the radiator can reduce the frontal area of the vehicle, thus reducing drag, in addition to the efficiency benefits gained by performing the dissociation and/or reformation reactions described above, and/or extracting energy from the flow that does impinge on the frontal area.

Another feature of at least some of the foregoing embodiments is that energy that is normally wasted and/or provides detrimental forces as the vehicle passes through an airstream, can instead be harnessed and used by on-board systems. This arrangement can increase the overall efficiency with which the vehicle operates. When the systems are coupled with a thermochemical reactor, the efficiency of the reactor can be increased.

The methods disclosed herein include and encompass, in addition to methods of making and using the disclosed devices and systems, methods of instructing others to make and use the disclosed devices and systems. For example, a method in accordance with a particular embodiment includes extracting energy from an airstream passing a moving transport platform and providing the energy to a thermochemical reactor carried by the transport platform. The method can further include, at the thermochemical reactor, receiving a donor substance and dissociating the donor substance into a first constituent and a second constituent in a non-combustion reaction. The method can still further include using at least one of the first and second constituents to preserve a cargo carried by the transport platform A method in accordance with another embodiment includes instructing such a method. Accordingly, any and all methods of use and manufacture disclosed herein also fully disclose and enable corresponding methods of instructing such methods of use and manufacture.

From the foregoing, it will be appreciated that specific embodiments of the presently disclosed technology have been described herein for purposes of illustration, but that various modifications may be made without deviating from the technology. For example, specific components shown in Figures at particular positions of the associated mobile transport platform can, in other embodiments, be located at other positions. In particular, the louvers, turbines, sensors, and/or gas flow system components can be located at other positions that are tailored to the particular geometry and/or expected use for the associated mobile transport platform. Particular embodiments for generating hydrogen were described above in the context of a high-temperature dissociation reactor. In other embodiments, electrolysis is used to dissociate a hydrogen donor into hydrogen or a hydrogen-bearing constituent. In still a further aspect of such embodiments, the electrical energy used to conduct the hydrolysis reaction can be obtained from the action of the shock absorbers and/or other reciprocating components of the transport platform.

Certain aspects of the technology described in the context of particular embodiments may be combined or eliminated in other embodiments. For example, as was discussed above, any of the energy extraction systems may be used singly or in combination with other energy extraction systems to provide power to any suitable on-board subsystem. Systems such as the evaporative refrigeration systems described above can be used alone or in combination with any of the other systems, for example, the aerodynamic regenerative braking system, the cross-wind control system, and/or the thermochemical process reactor. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the present disclosure and associated technology can encompass other embodiments not expressly shown or described herein.

I claim:

1. A chemical processing method, comprising:
   extracting energy from an airstream passing a moving transport platform;
   providing the energy to a thermochemical reactor carried by the transport platform;
   at the thermochemical reactor:
     receiving a donor substance; and
     dissociating the donor substance into a first constituent and a second constituent in a non-combustion reaction; and
   removing the first and second constituents from the thermochemical reactor and using at least one of the first and second constituents to preserve a cargo carried by the transport platform.

2. The method of claim 1 wherein preserving the cargo includes directing the at least one constituent to a refrigerator, and operating the refrigerator to cool the cargo.

3. The method of claim 2 wherein directing the at least one constituent to the refrigerator includes recharging a refrigerant carried by the refrigerator with the at least one constituent.

4. The method of claim 1 wherein preserving the cargo includes directing the at least one constituent into a payload volume of the transport platform to cool the payload volume.

5. The method of claim 1 wherein preserving the cargo includes at least discouraging pests by directing the at least one constituent into a payload volume of the transport platform.

6. The method of claim 1 wherein the at least one constituent includes carbon monoxide.

7. The method of claim 1 wherein the at least one constituent includes carbon monoxide, and wherein the cargo includes at least one of fish or meat.

8. The method of claim 1 wherein the at least one constituent includes carbon dioxide.

9. The method of claim 1 wherein the at least one constituent includes nitrogen.

10. The method of claim 1, further comprising:
    directing the first and second constituents removed from the thermochemical reactor to a manifold; and
    selectively using only one of the constituents to preserve the cargo carried by the transport platform by operating the manifold.

11. The method of claim 1, further comprising:
    braking the transport platform; and
    transferring energy resulting from braking the transport platform to the thermochemical reactor to facilitate the non-combustion reaction.

12. The method of claim 1 wherein the transport platform includes an over-the-road truck.

13. The method of claim 1, wherein at least one of the first and second constituents is a gas when removed from the thermochemical reactor and wherein the method further comprises cooling the gaseous constituent to form a liquid or a solid constituent and using the liquid or solid constituent to preserve the cargo carried by the transport platform.

* * * * *